United States Patent
Mets

(10) Patent No.: US 12,359,226 B2
(45) Date of Patent: *Jul. 15, 2025

(54) METHANOTHERMOBACTER THERMAUTOTROPHICUS STRAIN AND VARIANTS THEREOF

(71) Applicant: THE UNIVERSITY OF CHICAGO, Chicago, IL (US)

(72) Inventor: Laurens Mets, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/673,455

(22) Filed: Feb. 16, 2022

(65) Prior Publication Data

US 2022/0170050 A1 Jun. 2, 2022

Related U.S. Application Data

(60) Continuation of application No. 16/574,984, filed on Sep. 18, 2019, now abandoned, which is a division of application No. 15/216,616, filed on Jul. 21, 2016, now abandoned, which is a continuation of application No. 13/978,077, filed as application No. PCT/US2012/020386 on Jan. 5, 2012, now Pat. No. 9,428,745.

(60) Provisional application No. 61/430,071, filed on Jan. 5, 2011.

(51) Int. Cl.
| | |
|---|---|
| C12P 5/02 | (2006.01) |
| C12N 1/20 | (2006.01) |
| C12N 13/00 | (2006.01) |
| C12N 15/01 | (2006.01) |
| C12R 1/01 | (2006.01) |
| G01N 27/403 | (2006.01) |

(52) U.S. Cl.
CPC ............... C12P 5/023 (2013.01); C12N 1/20 (2013.01); C12N 1/205 (2021.05); C12N 13/00 (2013.01); C12N 15/01 (2013.01); C12R 2001/01 (2021.05); G01N 27/403 (2013.01); Y02E 50/30 (2013.01)

(58) Field of Classification Search
CPC ........ C12P 5/023; C12M 21/04; C12M 29/24; C12M 43/04; C12M 45/06; C12M 47/18; Y02E 50/30
See application file for complete search history.

(56) References Cited

U.S. PATENT DOCUMENTS

| | | |
|---|---|---|
| 1,940,944 A | 12/1933 | Franz et al. |
| 2,097,454 A | 11/1937 | Fischer |
| 3,640,846 A | 2/1972 | Johnson |
| 3,766,027 A | 10/1973 | Gregory |
| 3,852,180 A | 12/1974 | Gregory |
| 3,981,800 A | 9/1976 | Ort |
| 4,022,665 A | 5/1977 | Ghosh et al. |
| 4,430,176 A | 2/1984 | Davison |
| 4,540,666 A | 9/1985 | Nukina et al. |
| 4,608,132 A | 8/1986 | Sammells |
| 4,608,133 A | 8/1986 | Morduchowitz et al. |
| 4,609,440 A | 9/1986 | Frese, Jr. et al. |
| 4,620,928 A | 11/1986 | Gott |
| 4,673,473 A | 6/1987 | Ang et al. |
| 4,722,741 A | 2/1988 | Hayes et al. |
| 4,756,806 A | 7/1988 | Krist et al. |
| 4,883,753 A | 11/1989 | Belaich et al. |
| 4,921,799 A | 5/1990 | Kitaura et al. |
| 5,143,835 A | 9/1992 | Nakatsugawa et al. |

(Continued)

FOREIGN PATENT DOCUMENTS

| | | |
|---|---|---|
| DE | 10330375 A1 | 12/2004 |
| EP | 0253744 A1 | 1/1988 |

(Continued)

OTHER PUBLICATIONS

Labrou et al. Random Mutagenesis Methods for In Vitro Directed Enzyme Evolution. 2010, Current Protein and Peptide Science, v11(1), p. 91-100. (Year: 2010).*

(Continued)

*Primary Examiner* — Sean C. Barron
(74) *Attorney, Agent, or Firm* — MARSHALL, GERSTEIN & BORUN LLP

(57) ABSTRACT

Provided herein is an isolated *Methanothermobacter* microorganism that is (a) a microorganism of *Methanothermobacter thermautotrophicus* strain UC 120910, deposited on Dec. 21, 2010, with the American Type Culture Collection (ATCC) under ATCC® Patent Deposit Designation No. PTA-11561, (b) a variant of the microorganism of *Methanothermobacter thermautotrophicus* strain UC 120910, or (c) a progeny of the microorganism of *Methanothermobacter thermautotrophicus* strain UC 120910, wherein the variant or progeny retains the phenotypic characteristics of the microorganism of *Methanothermobacter thermautotrophicus* strain UC 120910. Also provided herein is a substantially pure culture or monoculture comprising the *Methanothermobacter* microorganism of the disclosure. A system for converting electric power into methane, comprising a biological reactor having at least a cathode, an anode, a presently disclosed *Methanothermobacter* microorganism, water, and carbon dioxide, and method of using the system for converting electricity into methane are further provided herein.

20 Claims, 25 Drawing Sheets

Specification includes a Sequence Listing.

(56) References Cited

U.S. PATENT DOCUMENTS

| | | | |
|---|---|---|---|
| 5,360,522 | A | 11/1994 | Kuroda et al. |
| 5,443,706 | A | 8/1995 | Kuroda et al. |
| 5,783,081 | A | 7/1998 | Gaddy |
| 5,922,204 | A | 7/1999 | Hunter et al. |
| 5,976,719 | A | 11/1999 | Kim et al. |
| 6,033,506 | A | 3/2000 | Klett |
| 6,270,649 | B1 | 8/2001 | Zeikus et al. |
| 6,284,399 | B1 | 9/2001 | Oko et al. |
| 6,340,581 | B1 | 1/2002 | Gaddy |
| 6,495,023 | B1 | 12/2002 | Zeikus et al. |
| 6,667,171 | B2 | 12/2003 | Bayless et al. |
| 6,699,654 | B1 | 3/2004 | McLeod et al. |
| 6,716,351 | B2 | 4/2004 | Fassbender |
| 6,802,974 | B2 | 10/2004 | Rebholz et al. |
| 7,033,822 | B2 | 4/2006 | Maston |
| 7,250,288 | B2 | 7/2007 | Zeikus et al. |
| 7,439,047 | B2 | 10/2008 | Rozendal et al. |
| 7,459,223 | B2 | 12/2008 | Zeikus et al. |
| 7,491,453 | B2 | 2/2009 | Logan et al. |
| 7,608,439 | B2 | 10/2009 | McTavish et al. |
| 9,428,745 | B2 * | 8/2016 | Mets ..................... C12N 15/01 |
| 2006/0011491 | A1 | 1/2006 | Logan et al. |
| 2006/0257985 | A1 | 11/2006 | Lovley et al. |
| 2007/0237993 | A1 | 10/2007 | Carlsson et al. |
| 2007/0259217 | A1 | 11/2007 | Logan |
| 2008/0286624 | A1 | 11/2008 | Lovley et al. |
| 2009/0130734 | A1 * | 5/2009 | Mets ..................... C12M 21/04 |
| | | | 435/167 |
| 2009/0317882 | A1 | 12/2009 | Cheng et al. |
| 2010/0143822 | A1 | 6/2010 | Zheng et al. |
| 2011/0165667 | A1 | 7/2011 | Mets |
| 2011/0281333 | A1 | 11/2011 | Brown et al. |
| 2011/0287504 | A1 | 11/2011 | Mets |
| 2014/0377830 | A1 | 12/2014 | Mets |
| 2016/0319305 | A1 | 11/2016 | Mets |
| 2018/0094283 | A1 | 4/2018 | Mets |
| 2018/0208884 | A1 | 7/2018 | Mets |

FOREIGN PATENT DOCUMENTS

| | | |
|---|---|---|
| EP | 0332134 A2 | 9/1989 |
| EP | 1574581 A2 | 9/2005 |
| JP | 62236489 A | 10/1987 |
| WO | WO-03/006713 A1 | 1/2003 |
| WO | WO-2007/073598 A1 | 7/2007 |
| WO | WO-2008/094282 A1 | 8/2008 |
| WO | WO-2009/155587 A2 | 12/2009 |
| WO | WO-2011/003081 A1 | 1/2011 |

OTHER PUBLICATIONS

Pennings et.al. Isolation and Characterization of Methanobacterium thermoautotrophicum [delta]H Mutants Unable to Grow under Hydrogen-Deprived Conditions. 1998, Journal of Bacteriology, v180(10), p. 2676-2681. (Year: 1998).*
Wasserfallen et al. Phylogenetic analysis of 18 thermophilic Methanobacterium isolates supports the proposals to create a new genus, *Methanothermobacter* gen. nov., an.2000, International Journal of System and Evolutionary Microbiology, v50, p. 43-53. (Year: 2000).*
Schill et al. Thermodynamic Analysis of Growth of Methanobacterium thermoautotrophicum. Biotechnology and Bioengineering (1996), 51(6), 645-658. (Year: 1996).*
2009 Hydrogen Program Annual Merit Review Meeting, PEM Electrolyzer Incorporating an Advanced Low Cost Membrane, presented by Monjid Hamdan of Giner Electrochemical systems, LLC (May 20, 2009) (20 pages).
Air Dispersion Modeling Conversion and Formula Reference (archived Jun. 10, 2004; website accessed at https://web.archive.org/web/20040610205839/http://www.air-dispersion.com/formulas/html).
Assembly Instructions, Multipurpose Cell MP-Cell, ElectroCell (8 pages).
Bae et al., Sulfonated Poly(arylene ether sulfone ketone) Multiblock Copolymers with Highly Sulfonated Block. Synthesis and Properties, *Macromolecules*, 43:2684-91 (2010).
Balch et al., New approach to the cultivation of methanogenic bacteria: 2-mercaptoethanesulfonic acid (HS-CoM)-dependent growth of Methanobacterium ruminantium in a pressureized atmosphere, Appl. Environ. Microbiol., 32(6):781-91 (1976).
Banchuen, Oxidation-Reduction (Redox) Reactions and Potentials, Master of Science Thesis Defense accessed by http://scholar.lib.vt.edu/theses/available/etd-01102003-162857/;2002).
Baughn et al., The strict anaerobe Bacteroides fragilis grows in and benefits from nanomolar concentrations of oxygen, Nature, 427(6973):441-4 (2004).
Brioukhanov et al., The catalase and superoxide dismutase genes are transcriptionally up-regulated upon oxidative stress in the strictly anaerobic archaeon Methanosarcina barkeri, Microbiology, 152(Pt. 6):1671-7 (2006).
Bryant et al., Methanobacillus Omelianskii, A Symbiotic Association of Two Species of Bacteria, *Arch. Mikrobiol.*, 59:20-31 (1967).
Butsch et al., The membrane potential in whole cells of Methanobacterium thermoautotrophicum, Arch. Microbiol., 138:293-8 (1984).
Camacho, The Geochemistry of Silica in Icelandic Geothermal Systems, Thesis, University of Iceland, Reykjavik (Sep. 2017).
Cheng et al., Direct Biological Conversion of Electrical Current into Methane by Electromethanogenesis, *Environ. Sci. Technol.*, 43:3953-8 (2009).
Chlor-alkali Electrolysis Plants, Superior Membrane Process Brochure, Uhde, Dortmund, Germany (2008) (24 pages).
DSM 3590, Methanothermobacter thermautotrophicus, Strain Hveragerdi (Nov. 12, 1985).
European Patent Application No. 16156757, Communication Pursuant to Article 94(3) EPC, dated Mar. 7, 2019.
European Patent Application No. 16156757, Summons to Attend Oral Proceedings Pursuant to Rule 115(1) EPC, dated Jan. 14, 2020.
European Patent Application No. 16156757.3, Communication Pursuant to Article 94(3) EPC, dated Mar. 22, 2018.
European patent application No. 16156757.3, Communication Pursuant to Article 94(3) EPC, dated May 9, 2017.
European Patent Application No. 16156757.3, Communication Pursuant to Rule 114(2) EPC (Third Party Observations), dated Feb. 6, 2018.
Extended European Search Report, European patent application. No. 16156757, dated Jul. 29, 2016.
Ferry et al., Microbiological principles of methane formation from biomass, Food Engineering News, 4 pp (1985).
Fetzer et al., Effect of redox potential on methanogenesis by Methanoscarcina barkeri, Arch. Microbiol., 160:108-13 (1993).
Fornero et al., Microbial Fuel Cell Performance with a Pressurized Cathode Chamber, *Environ. Sci. Tech.* 42(22):8578-84 (2008).
Frols et al., Response of the Hyperthermophilic Archaeon Sulfolobus Solfataricus to UV Damage, *J. Bacteriol.*, 189 (23):8708-18 (2007).
Frols et al., UV-inducible Cellular Aggregation of the Hyperthermophilic Archaeon Sulfolobus Solfataricus is Mediated by Pili Formation, *Mol. Microbiol.*, 70 (4):938-52 (2008).
Galhardo et al., Mutation as a stress response and the regulation of evolvability, Crit. Rev. Biochem. Mol. Biol., 42(5):399-435 (2007).
GreenShift Industrial Design Corporation: GreenShift Acquires Rights to Patented Carbon Dioxide Reduction Technology; New Strain of Thermophilic Cyanobacteria Converts Exhaust Carbon Dioxide into Pure Oxygen and Clean Water. Dec. 12, 2005 (2 pp.).
Gregory et al., "Graphite electrodes as electron donors for anaerobic respiration", Environmental Microbiology, 6(6), 596-604 (2004).
He et al., "An upflow microbial fuel cell with an interior cathode: Assessment of the internal resistance by impedance spectroscopy," Environ. Sci. Technol., 40: 5212-7 (2006).
He et al., "Application of Bacterial Biocathodes in Microbial Fuel Cells", Electroanalysis, 18 (19-20):2009-15 (Oct. 2006).
Hu et al., Highly Conductive Paper for Energy-storage Devices, *Proc. Natl. Acad. Sci. USA*, 106(51):21490-4 (2009).
Iijima, Helical Microtubules of Graphitic Carbon, *Nature*, 354:56-8 (1991).

(56) References Cited

OTHER PUBLICATIONS

International Search Report and Written Opinion, corresponding International Application No. PCT/US2012/020386, dated Jun. 19, 2012.

Ishii et al., "Methanogenesis versus Electrogenesis: Morphological and Phylogenetic Comparisons of Microbial Communities", Bioscience, Biotechnology, and Biochemistry, 72(2):286-94 (2008).

Jiang et al., Synthesis of Diode Molecules and Their Sequential Assembly to Control Electron Transport, *Angew. Chem., Int. Ed. Engl.*, 43:4471-5 (2004).

Jung et al., Supported Nafion Membrane for Direct Methanol Fuel Cell, *J. Fuel Cell Sci. Technol.*, 4:248-55 (2007).

Kato et al., Anaerobe tolerance to oxygen and the potentials of anaerobic and aerobic cocultures for wastewater treament, Braz. J. Chem. Eng., 14(4):1-19 (1997).

Kato et al., Comparative transcriptome analysis of responses of Methanothermobacter thermautotrophicus to different environmental stimuli, 10(4):893-905 (2008).

Kiener et al., Oxygen sensitivity of methanogenic bacteria, Syst. Appl. Microbiol., 4(3):305-12 (1983).

Labrou, Random mutagenesis methods for in vitro directed enzyme evolution, Curr. Protein Peptide Sci., 11:91-100 (2010).

Liu et al., "Electrochemically Assisted Microbial Production of Hydrogen from Acetate," Environ. Sci. Technol., 39:4317-20 (2005).

Luo et al., Differential Expression of Methanogenesis Genes of Methanothermobacter Thermoautotrophicus (Formerly Methanobacterium Thermoautorophicum) in Pure Culture and in Cocultures with Fatty Acid-oxidizing Synthrophs, *Appl. Env., Microbiol.*, 68 (3):1173-9 (2002).

Martin et al., A single-culture bioprocess of Methanothermobacter thermautotrophicus to upgrade digester biogas by $CO_2$-to-$CH_4$ conversion with $H_2$, Archaea, 2013:157529 (2013).

Mets, Development of a Solar Energy Storage System—A seed grant proposal to the Chicago Energy Initiative (Oct. 1, 2009; 6 pp.).

Moulthrop et al., Commercial Optimization of a 100kg/day PEM based Hydrogen Generator for Energy and Industrial Applications, WHEC 16, Jun. 13-16, 2006, Lyon, France (8 pages).

Mukhopadhyay et al., Reactor-scale cultivation of the hyperthermophilic methanarchaeon Methanococcus jannaschii to high cell densities, Appl. Environ. Microbiol., 65(11):5059-65 (1999).

Nester et al., "Dynamics of Prokaryotic Growth", Chapter 4 IN: Microbiology: A Human Perspective, 4th ed., McGraw Hill Higher Education (2004).

Nevin et al., "Microbial Electrosynthesis: Feeding Microbes Electricity to Convert Carbon Dioxide and Water to Multicarbon Extracellular Organic Compounds", mBio 1(2):e00103-10 (May 25, 2010).

Nishimura et al., Cultivation of thermophilic methanogen KN-15 on $H_2$—$CO_2$ under pressurized conditions, J. Fermentation and Bioengineering, 73(6):477-80 (1992).

Nölling et al., Phylogenetic analysis of *Thermophilic methanobacterium* sp.: evidence for a formate-utilizing ancestor, System. Appl. Microbiol., 16:208-15 (1993).

Park et al., Microbial Utilization of Electrically Reduced Neutral Red as the Sole Electron Donor for Growth and Metabolite Production, *Appl. Env. Microbiol.*, 65 (7):2912-7 (1999).

Pennings et al., Isolation and characterization of Methanobacterium thermoautotrophicum ΔH mutants unable to grow under hydrogen-deprived conditions, J. Bacteriol., 180(10):2676-81 (1998).

Reeve et al., Methanogenesis: genes, genomes, and who's on first, J. Bacteriol., 179(19):5975-86 (1997).

Rosenbaum et al., "Cathodes as electron donors for microbial metabolism: which extracellular electron transfer mechanisms are involved?", Bioresource Technol. 102(1):324-33 (Aug. 4, 2010).

Rozendal et al., "Hydrogen Production with a Microbial Biocathode", Environ. Sci. Technol., 42(2):629-34 (2008).

Schill et al., Continuous Cultures Limited by a Gaseous Substrate: Development of a Simple, Unstructured Mathematical Model and Experimental Verification with Methanobacterium Thermoautotrophicum, *Biotechnol. Bioeng.*, 51:645-58 (1996).

Seedorf et al., F420H2 oxidase (FprA) from methanobrevibacter arboriphilus, a conenzyme F420-dependent enzyme involved in O2 detoxification, Arch.Microbiol., 182:126-37 (2004).

Sehested et al., Methanation of CO over nickel: mechanism and kinetics at high H2/CO ratios, J. Phys. Chem. B, 109:2432-8 (2005).

Sipma et al., Microbial CO conversions with applications in synthesis gas purification and bio-desulfurization, Crit. Rev. Biotechnol., 26:41-65 (2006).

Sowers et al., Techniques for Anaerobic Growth, Protocol 1, pp. 15-47 in Archaea: A Laboratory Manual: Methanogens, Cold Spring Harbor Laboratory Press (1995).

Szabo et al., Flagellar motility and structure in the hyperthermoacidophilic archaeon Sulfolobus solfataricus, *J. Bacteriol.*, 189 (11):4305-9 (2007).

Thakker et al., An alkalophilic Methanosarcina isolated from Lonar crater, Current Science, 82(4):455-8 (2002).

Thauer et al., "Energy Conservation in Chemotrophic Anaerobic Bacteria", Bacteriological Reviews, 40(1):100-80 (Mar. 1977).

Villano et al., "Bioelectrochemical reduction of CO2 to CH4 via direct and indirect extracellular electron transfer by a hydrogenophilic methanogenic culture," Bioresource Technology, 101:3085-90 (2010).

Waldron et al., Salinity Constraints on Subsurface Archaeal Diversity and Methanogenesis in Sedimentary Rock Rich in Organic Matter, *Appl. Env. Microbiology*, 73 (13):4171-9 (2007).

Wang et al., "Source of methane and methods to control its formation in single chamber microbial electrolysis cells", Intl. J. Hydrogen Energy, 34:3653-58 (2009).

Wang et al., Solubilization of Carbon Nanotubes by Nafion Toward the Preparation of Amperometric Biosensors, *J. Am. Chem. Soc.*, 125:2408-9 (2003).

Wang et al., The Structure of an Archaeal Pilus, *J. Mol. Biol.*, 381 (12):456-66 (2008).

Wang et al., The Structure of F-pili, *J. Mol. Biol.*, 385 (1):22-9 (2008).

Wasserfallen et al., Phylogenetic analysis of 18 thermophilic Methanobacterium isolates supports the proposals to create a new genus, *Methanothermobacter* gen. nov., and to reclassify several isolates in three species, *Methanothermobacter thermautotrophicus* comb. nov., *Methanothermobacter wolfeii* comb. nov., and *Methanothermobacter marburgensis* sp. nov, Int. J. Syst. Evol. Microbiol., 50 Pt. 1:43-53 (2000).

Wise et al., Biomethanation: anaerobic fermentation of CO2, H2 and CO to methane, Biotech. Bioeng., xx:1153-72 (1978).

Woese et al., Towards a natural system of organisms: proposal for the domains Archaea, Bacteria, and Eucarya, Proc. Natl. Acad. Sci. USA, 87(12):4576-9 (1990).

Worakit et al., *Methanobacterium alcaliphilum* sp. nov., an H2-utilizing methanogen that grows at high pH values, Int. J. Systematic Bacteriol., 36(3):380-2 (Jul. 1986).

Zehnder et al., Physiology of methanobacterium strain AZ, Arch. Microbiol., 111:199-205 (1977).

Zeikus et al., *Methanobacterium thermoautotrophicus* sp. n., an anaerobic, autotrophic, extreme thermophile, J. Bacteriol., 109(2):707-13 (1972).

Zolghadr et al., Identification of a System Required for the Functional Surface Localization of Sugar Binding Proteins with Class III Signal Peptides in Sulfolobus Solfataricus, *Mol. Microbiol.*, 64 (3):795-806 (2007).

\* cited by examiner

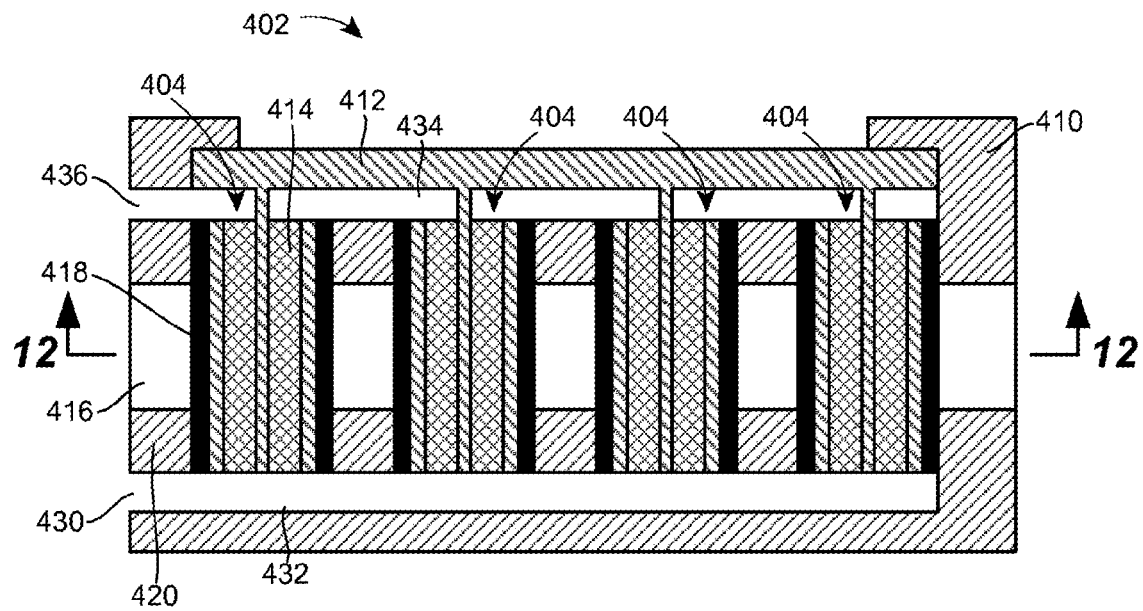
FIG. 11
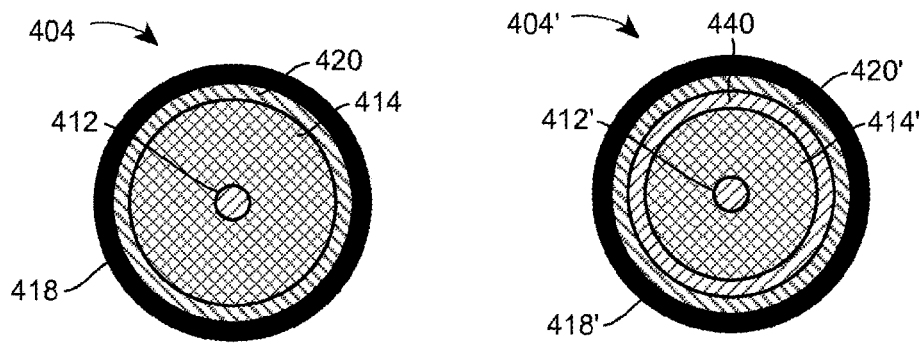
FIG. 12  FIG. 13

METHANOTHERMOBACTER THERMAUTOTROPHICUS STRAIN AND VARIANTS THEREOF

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 6 KB ASCII (Text) file named "45956A_SeqListing.txt," created on Jan. 4, 2012.

BACKGROUND

The United States annually consumes about 90 ExaJoules (EJ) of carbon-based fuels, 88% of its total energy consumption in 2008. The use of these fuels is supported by heavily capitalized processing, distribution and utilization industries.

The sustainability of these systems is questionable on two counts. First, the US imports 25% of the energy it uses, a proportion that is projected to increase substantially. Imported energy is obtained from sources that are under pressure to serve increasing demand from growing economies in other parts of the world. Second, more than 96% of the carbon-based fuels are obtained from fossil reserves, which are finite. Useful energy is obtained from carbon-based fuels by oxidizing reduced states of carbon to carbon dioxide. For fossil fuels, this process is basically open-loop, producing $CO_2$ with no compensating carbon reduction process to close the cycle. The consequent gradual accumulation of atmospheric $CO_2$ is beginning to cause changes in the global climate that threaten many aspects of our way of life. Therefore, a process that can close this carbon energy cycle for the total energy economy is needed.

An annual flux of 58,000 EJ of solar energy strikes US soil, making it our most abundant carbon-free energy resource—500 times current consumption. Solar energy has the unique advantage of being a domestic resource not just in the US, but everywhere that people live. Its widespread use as a primary resource would secure energy independence throughout the world. Nevertheless, today solar energy is only a marginal component of the energy economy, providing less than 0.1% of marketed US energy consumption. Exploitation of solar energy is limited principally because it is intermittent and cannot be relied upon to provide the base-load energy that must be available whenever needed. What is lacking is a method for storing solar energy in a stable form that can be tapped whenever needed. Ideally, such a storage form should fit smoothly into the existing energy infrastructure so that it can be quickly deployed once developed.

There is a need in the energy industry for systems to convert one form of energy into another. In particular, there is a need for systems to convert electricity into a form of energy that can be stored inexpensively on industrial scales. Many sources of electricity generation cannot be adjusted to match changing demand. For example, coal power plants run most efficiently when maintained at a constant rate and cannot be adjusted as easily as natural gas (methane) fired power plants. Likewise, wind turbines generate electricity when the wind is blowing which may not necessarily happen when electricity demand is highest.

There is also a need to convert electricity into a form that can be transported long distances without significant losses. Many opportunities for wind farms, geothermal, hydroelectric or solar based power generation facilities are not located close to major population centers, but electric power losses over hundreds of miles add significant cost to such distant power facilities.

Methane is one of the most versatile forms of energy and can be stored easily. There already exists much infrastructure for transporting and distributing methane as well as infrastructure for converting methane into electricity and for powering vehicles. Methane also has the highest energy density per carbon atom of all fossil fuels, and therefore of all fossil fuels, methane releases the least carbon dioxide per unit energy when burned. Hence, systems for producing methane, e.g., through converting carbon dioxide and electricity into methane, would be highly useful and valuable in all energy generation and utilization industries.

SUMMARY

The disclosure provides an isolated *Methanothermobacter* microorganism that produces methane from carbon dioxide via a process called methanogenesis. In exemplary aspects, the *Methanothermobacter* microorganism is a microorganism of the species *thermautotrophicus*, which is also known as *thermoautotrophicus*, which is also known as *thermautotrophicum* or *thermoautotrophicum*. In exemplary aspects, the *Methanothermobacter* microorganism is a microorganism of the species *marburgensis*.

In exemplary aspects, the *Methanothermobacter* microorganism of the disclosure exhibits the phenotypic characteristics described herein. In exemplary aspects, the *Methanothermobacter* microorganism exhibits a high methane production efficiency. For instance, the *Methanothermobacter* microorganism exhibits a high methane production efficiency that is at least or about 25 $CO_2$ molecules converted to methane per $CO_2$ molecule converted to cellular material.

In exemplary aspects, the *Methanothermobacter* microorganism demonstrates a high level of methane productivity. For example, the *Methanothermobacter* microorganism produces at least or about 96 molecules of methane per 100 molecules of carbon dioxide supplied to the microorganism.

In exemplary aspects, the *Methanothermobacter* microorganism demonstrates a high level of methane productivity. For instance, the *Methanothermobacter* microorganism produces at least or about 17 grams of methane per gram of *Methanothermobacter* cellular material (i.e., biomass) produced.

In exemplary aspects, the *Methanothermobacter* microorganism exhibits a doubling time of at least or about 72 hours in a stationary phase. By virtue of the slow doubling time, the *Methanothermobacter* microorganism in exemplary aspects exhibits a significant reduction in required nutrients for maintenance and growth of the microorganisms.

In exemplary aspects, the *Methanothermobacter* microorganism:
  a. exhibits a methane production efficiency that is at least or about 25 $CO_2$ molecules converted to methane per $CO_2$ molecule converted to cellular material; or
  b. survives in a stationary phase with a doubling time of at least or about 72 hours; or
  c. exhibits a cell culture density of at least or about 6 mg dry mass of cells/ml culture in a stationary phase; or
  d. returns to at least 80% of the methane productivity level in the operating state within 20 minutes of exposure to at least or about 3 minutes to either oxygen or carbon monoxide; or e. a combination (e.g., a combination of (a)-(d) or a sub-combination of (a) to (d)) thereof.

In exemplary aspects, the *Methanothermobacter* microorganism is (1) autotrophic and either thermophilic or hyperthermophilic; and (2) capable of returning to at least 80% (e.g., 90%, 95%, 98%) of the methane productivity level in the operating state within 20 minutes, after an exposure of at least 10 minutes to oxygen (e.g. oxygen in ambient air) or carbon monoxide; and any one or more of the following:

(3) capable of exhibiting a methane production efficiency per molecule of carbon dioxide ($CO_2$) that is at least or about 25 CO) molecules converted to methane per $CO_2$ molecule converted to cellular material (e.g., at least or about 40, 50, 60, or 70 $CO_2$ molecules converted to methane per $CO_2$ molecule converted to cellular material), optionally while exhibiting a doubling time of at least or about 72 hours;

(4) capable of surviving with a doubling time of at least or about 72 hours (e.g., a doubling time of at least or about 80, 90, or 100 hours) for at least 30 days (e.g., for at least about 1, 2, 3, 4, 5, 6, 7, 8, 9, 10, 11 or 12 months)—e.g., in a stationary or a nearly stationary phase;

(5) capable of continuously maintaining a methane production efficiency of (3) for at least 30 days (e.g., for at least or about 6 months, at least or about 12 months), optionally while in a stationary phase or a nearly stationary phase having a doubling time of at least or about 72 hours (e.g., a doubling time of at least or about 80, 90, or 100 hours); and (6) capable of returning to at least 80% (e.g., 90%, 95%, 98%) of the methane productivity in the operating state within 20 minutes of re-supplying hydrogen ($H_2$) gas or electricity, after being in a dormant state for at least 2 hours as induced by interrupting or ceasing $H_2$ gas supply or electricity.

In exemplary aspects, the isolated *Methanothermobacter* microorganism produces methane at a pH within a range of about 6.5 to about 7.5, at a temperature within a range of about 55° C. to about 69° C., and/or in a medium having a conductivity within a range of about 5 mS/cm to about 100 mS/cm.

In exemplary embodiments, the isolated *Methanothermobacter* microorganism of the disclosure is (a) a microorganism of *Methanothermobacter thermautotrophicus* strain UC 120910, deposited on Dec. 21, 2010, with the American Type Culture Collection (ATCC®) under ATCC® Patent Deposit Designation No. PTA-11561, (b) a variant of a microorganism of *Methanothermobacter thermautotrophicus* strain UC 120910, or (c) a progeny of a microorganism of *Methanothermobacter thermautotrophicus* strain UC 120910, wherein the variant or progeny retains the $CO_2$ conversion phenotypic characteristics of a microorganism of *Methanothermobacter thermautotrophicus* strain UC 120910.

In exemplary embodiments, the isolated *Methanothermobacter* microorganism of the disclosure is an isolated progeny of a *Methanothermobacter* microorganism of *Methanothermobacter thermautotrophicus* strain UC 120910, deposited on Dec. 21, 2010, with the American Type Culture Collection (ATCC) under ATCC® Patent Deposit Designation No. PTA-11561, that retains the $CO_2$ conversion phenotypic characteristics of strain UC 120910.

The disclosure also provides a substantially pure culture or monoculture comprising any of the microorganisms of the disclosure. In exemplary aspects, the substantially pure culture or monoculture comprises a *Methanothermobacter* microorganism that is (a) a microorganism of *Methanothermobacter thermautotrophicus* strain UC 120910, deposited on Dec. 21, 2010, with the American Type Culture Collection (ATCC®) under ATCC® Patent Deposit Designation No. PTA-11561, (b) a variant of a microorganism of *Methanothermobacter thermautotrophicus* strain UC 120910, or (c) a progeny of a microorganism of *Methanothermobacter thermautotrophicus* strain UC 120910, wherein the variant or progeny retains the $CO_2$ conversion phenotypic characteristics of the microorganism of *Methanothermobacter thermautotrophicus* strain UC 120910.

The disclosure furthermore provides a system for producing methane from carbon dioxide comprising any of the microorganisms of the disclosure. In exemplary aspects, the system is for converting electric power into methane. In exemplary embodiments, the system comprises a biological reactor having at least a cathode, an anode, water, a supply of carbon dioxide, and a *Methanothermobacter* microorganism that is (a) a microorganism of *Methanothermobacter thermautotrophicus* strain UC 120910, deposited on Dec. 21, 2010, with the American Type Culture Collection (ATCC®) under ATCC® Patent Deposit Designation No. PTA-11561, (b) a variant of a microorganism of *Methanothermobacter thermautotrophicus* strain UC 120910, or (c) a progeny of a microorganism of *Methanothermobacter thermautotrophicus* strain UC 120910, wherein the variant or progeny retains the $CO_2$ conversion phenotypic characteristics of the microorganism of *Methanothermobacter thermautotrophicus* strain UC 120910. In exemplary embodiments, the biological reactor comprises at least a first chamber comprising said cathode, said microorganism or said progeny, water, and a supply of carbon dioxide, and a second chamber containing at least an anode. In exemplary embodiments, the system comprises, in addition to the biological reactor, a source of electricity coupled to the anode and the cathode, a supply of carbon dioxide coupled to the first chamber, and an outlet to receive methane from the first chamber.

The disclosure moreover provides a method of converting electricity into methane. In exemplary embodiments, the method comprises supplying electricity and carbon dioxide to the presently disclosed system comprising a biological reactor, the biological reactor having an operating state wherein the microorganism is maintained at a temperature greater than or about 60° C. and collecting methane from the first chamber.

The disclosure further provides a porous cathode comprising a microorganism as described herein. Kits are also provided, wherein the kits comprise a microorganism, a substantially pure culture or monoculture, a system, a porous cathode, as described herein, or a combination thereof, along with instructions for care or for use.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

FIG. 11 is a cross-sectional view of the system of FIG. 10 taken along line 11-11;

FIG. 12 is a cross-sectional view of one of the plurality of biological reactors of FIG. 11 taken along line 12-12;

FIG. 13 is a cross-sectional view of a variant biological reactor for use in the system of FIG. 10;

DETAILED DESCRIPTION

Figure 1:
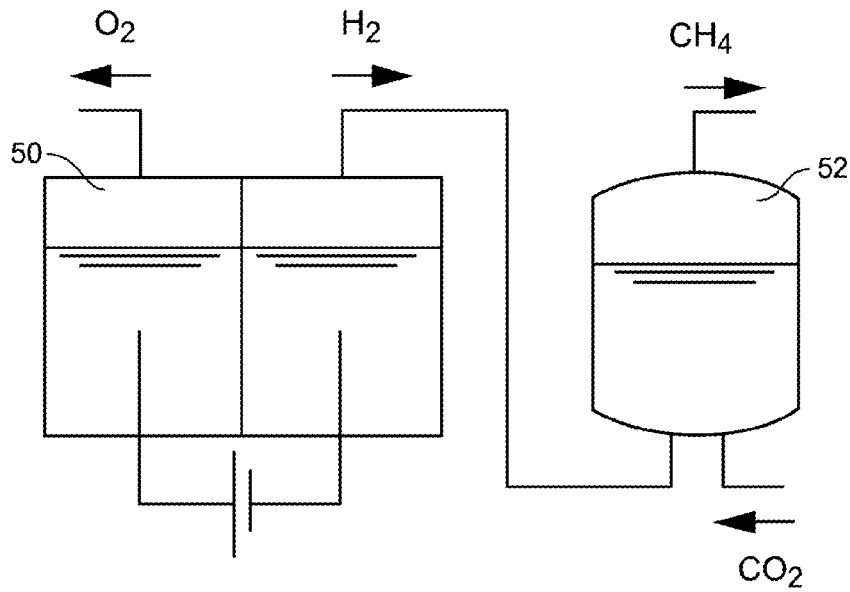
FIG. 1 is a schematic view of a system for converting carbon dioxide into methane using a digester.

Although the following text sets forth a detailed description of numerous different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term is '_____' hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Microorganisms

The disclosure provide microorganisms that produce methane from carbon dioxide via a process called methanogenesis. Accordingly, the microorganisms of the disclosure are methanogenic microorganisms, also known as methanogens. As used herein, the term "methanogenic" refers to microorganisms that produce methane as a metabolic byproduct. In exemplary aspects, the microorganism produces methane from carbon dioxide, electricity, and water, via a process called electrobiological methanogenesis. In exemplary aspects, the microorganism utilizes hydrogen in the production of methane via a process called hydrogenotrophic methanogenesis. Accordingly, in exemplary aspects, the presently disclosed microorganism is a hydrogenotrophic methanogenic microorganism. In exemplary aspects, the microorganism of the disclosure has the capacity to produce methane via electrobiological methanogenesis or via hydrogenotrophic methanogenesis. In exemplary aspects, the *Methanothermobacter* microorganism produces methane at a pH within a range of about 6.5 to about 7.5, at a temperature within a range of about 55° C. to about 69° C., and/or in a medium having a conductivity within a range of about 5 mS/cm to about 100 mS/cm.

In exemplary aspects, the presently disclosed microorganism belong to the genus *Methanothermobacter*. The characteristics of this genus are known in the art. See, e.g., Reeve et al., J Bacteriol 179: 5975-5986 (1997) and Wasserfallen et al., *Internatl J Systematic Evol Biol* 50: 43-53 (2000), each incorporated herein by reference. Accordingly, in exemplary aspects, the microorganism expresses a 16S rRNA which has at least 90% (e.g., at least 95%, at least 98%, at least 99%) sequence identity to the full length of the sequence of 16S rRNA of *Methanothermobacter thermautotrophicus* Delta H, which is publicly available from the under European Molecular Biology Laboratory (EMBL) sequence database as Accession No. X68720, and which is set forth herein as SEQ ID NO: 1. In exemplary aspects, the *Methanothermobacter* microorganism is a microorganism of the species *thermautotrophicus* which is also known as *thermoautotrophicus*. In exemplary aspects, the *Methanothermobacter* microorganism is a microorganism of the species *marburgensis*.

In exemplary aspects, the *Methanothermobacter* microorganism of the disclosure exhibits the phenotypic characteristics described herein. In exemplary aspects, the *Methanothermobacter* microorganism exhibits a high methane production efficiency. For instance, the *Methanothermobacter* microorganism exhibits a high methane production efficiency per molecule of $CO_2$ that is at least or about 25 $CO_2$ molecules converted to methane per $CO_2$ molecule converted to cellular material.

In exemplary aspects, the *Methanothermobacter* microorganism demonstrates a high level of methane productivity relative to the supplied carbon dioxide. For example, the *Methanothermobacter* microorganism produces at least or about 96 molecules of methane per 100 molecules of carbon dioxide supplied to the microorganism. As another example, the *Methanothermobacter* microorganism produces at least or about 17 grams of methane per gram of biomass produced.

In exemplary aspects, the *Methanothermobacter* microorganism exhibits a doubling time of at least or about 72 hours. Relative to the growth rate of this microorganism during exponential growth, for example, the doubling time of at least or about 72 hours defines a stationary phase or a nearly stationary phase of growth. By virtue of the slow doubling time, the *Methanothermobacter* microorganism in exemplary aspects exhibits a significant reduction in required nutrients for maintenance and growth of the microorganisms.

In exemplary aspects, the *Methanothermobacter* microorganism:
a. exhibits a methane production efficiency that is at least or about 25 $CO_2$ molecules converted to methane per $CO_2$ molecule converted to cellular material; or
b. survives with a doubling time of at least or about 72 hours (e.g., in a stationary phase or a nearly stationary phase); or
c. exhibits a cell culture density of at least or about 6 mg dry mass of cells/ml culture in a stationary phase or nearly stationary phase; or
d. returns to at least 80% of the methane productivity level in the operating state within 20 minutes of exposure to at least or about 3 minutes of either oxygen or carbon monoxide; or
e. a combination (e.g., a combination of (a)-(d) or a sub-combination of (a) to (d)) thereof.

In exemplary aspects, the *Methanothermobacter* microorganism is (1) autotrophic and either thermophilic or hyperthermophilic; and (2) capable of returning to at least 80% (e.g., 90%, 95%, 98%) of the methane productivity level in the operating state within 20 minutes of exposure to at least 10 minutes of oxygen (e.g. oxygen in ambient air) or carbon monoxide; and any one or more of the following:
(3) capable of exhibiting a methane production efficiency that is at least or about 25 $CO_2$ molecules converted to methane per CO) molecule converted to cellular material (e.g., at least or about 40, 50, 60, or 70 $CO_2$ molecules converted to methane per $CO_2$ molecule converted to cellular material), optionally while exhibiting a doubling time of at least or about 72 hours;
(4) capable of surviving with a doubling time of at least or about 72 hours (e.g., a doubling time of at least or about 80, 90, or 100 hours) for at least 30 days (e.g., for at least about 1, 2, 3, 4, 5, 6, 7, 8, 9, 10, 11 or 12 months);
(5) capable of continuously maintaining a methane production efficiency of (3) for at least 30 days (e.g., for at least or about 6 months, at least or about 12 months), optionally while exhibiting a doubling time of at least or about 72 hours (e.g., a doubling time of at least or about 80, 90, or 100 hours); and
(6) capable of returning to at least 80% (e.g., 90%, 95%, 98%) of the methane productivity in the operating state within 20 minutes of re-supplying hydrogen or electricity, after being in a dormant state for at least 2 hours as induced by interrupting or ceasing hydrogen supply or electricity.

In any of the exemplary embodiments described herein, the microorganism may be isolated. As used herein, the term "isolated" means having been removed from its natural environment, not naturally-occurring, and/or substantially purified from contaminants that are naturally associated with the microorganism.

Microorganisms: Strain UC 120910

In exemplary embodiments, the *Methanothermobacter* microorganism of the disclosure is a microorganism of *Methanothermobacter thermautotrophicus* strain UC 120910, deposited on Dec. 21, 2010, with the American Type Culture Collection (ATCC®) under ATCC® Patent Deposit Designation No. PTA-11561.

Microorganisms: Progeny

In alternative exemplary embodiments, the isolated *Methanothermobacter* microorganism of the disclosure is a progeny of the microorganism of *Methanothermobacter thermautotrophicus* strain UC 120910, which progeny retain the $CO_2$ conversion phenotypic characteristics of a microorganism of *Methanothermobacter thermautotrophicus* strain UC 120910, as further described herein. Optionally, the progeny retain additional phenotypic characteristics of *Methanothermobacter thermautotrophicus* strain UC 120910.

Accordingly, the disclosure also provide an isolated progeny of a *Methanothermobacter* microorganism of *Methanothermobacter thermautotrophicus* strain UC 120910, deposited on Dec. 21, 2010, with the American Type Culture Collection (ATCC®) under ATCC® Patent Deposit Designation No. PTA-11561, that retains the $CO_2$ conversion phenotypic characteristics of said strain.

As used herein, the term "progeny" refers to any microorganism resulting from the reproduction or multiplication of a microorganism of *Methanothermobacter thermautotrophicus* strain UC 120910. In this regard, "progeny" means any descendant of a microorganism of *Methanothermobacter thermautotrophicus* strain UC 120910. As such, the progeny are themselves identified as *Methanothermobacter thermautotrophicus* strain UC 120910. In exemplary embodiments, the progeny are genetically identical to a microorganism of *Methanothermobacter thermautotrophicus* strain UC 120910, and, as such, the progeny may be considered as a "clone" of the microorganism of *Methanothermobacter thermautotrophicus* strain UC 120910. In alternative exemplary embodiments, the progeny are substantially genetically identical to a microorganism of *Methanothermobacter thermautotrophicus* strain UC 120910, such that the sequence of the genome of the progeny is different from the genome sequence of the microorganism of *Methanothermobacter thermautotrophicus* strain UC 120910, but the phenotype of the progeny are substantially the same as the phenotype of a microorganism of *Methanothermobacter thermautotrophicus* strain UC 120910. In exemplary embodiments, the progeny are progeny as a result of culturing the microorganisms of *Methanothermobacter thermautotrophicus* strain UC 120910 under the conditions set forth herein, e.g., Example 1 or 2.

Microorganisms: Variants

In exemplary embodiments, the isolated *Methanothermobacter* microorganism of the disclosure is a variant of a microorganism of *Methanothermobacter thermautotrophicus* strain UC 120910, which variant retains the $CO_2$ conversion phenotypic characteristics of the microorganism of *Methanothermobacter thermautotrophicus* strain UC 120910, as further described herein.

Accordingly, the disclosure also provides an isolated variant of a *Methanothermobacter* microorganism of *Methanothermobacter thermautotrophicus* strain UC 120910, deposited on Dec. 21, 2010, with the American Type Culture Collection (ATCC®) under ATCC® Patent Deposit Designation No. PTA-11561, that retains the $CO_2$ conversion phenotypic characteristics of said strain.

As used herein, the term "variant" refers to any microorganism resulting from modification of a microorganism of *Methanothermobacter thermautotrophicus* strain UC 120910. In exemplary aspects, the variant is a microorganism resulting from adapting in culture a microorganism of *Methanothermobacter thermautotrophicus* strain UC 120910, as described herein. In alternative aspects, the variant is a microorganism resulting from genetically modifying a microorganism of *Methanothermobacter thermautotrophicus* strain UC 120910, as described herein.

In exemplary embodiments, the variant is a microorganism of *Methanothermobacter thermautotrophicus* strain UC 120910 modified to exhibit or comprise certain characteristics or features, which, optionally, may be specific to a given growth phase (active growth phase, stationary growth phase, nearly stationary growth phase) or state (e.g., dormant state, operating state). For example, in some embodiments, the microorganism of *Methanothermobacter thermautotrophicus* strain UC 120910 has been modified to survive and/or grow in a desired culture condition which is different from a prior culture condition in which the methanogenic microorganism of *Methanothermobacter thermautotrophicus* strain UC 120910 survived and/or grew. The desired culture conditions may differ from the prior environment in temperature, pH, pressure, cell density, volume, humidity, salt content, conductivity, carbon content, nitrogen content, vitamin-content, amino acid content, mineral-content, or a combination thereof. In some embodiments, the methanogenic microorganism, before adaptation in culture or genetic modification, is one that is not a halophile but, through adaptation in culture or genetic modification, has become a halophile. As used herein, "halophile" or "halophilic" refers to a microorganism that survives and grows in a medium comprising a salt concentration higher than 100 g/L. Also, for example, in some embodiments, the methanogenic microorganism before genetic modification is one which does not express a protein, but through genetic modification has become a methanogenic microorganism which expresses the protein. Further, for example, in some embodiments, the methanogenic microorganism before adaptation in culture or genetic modification, is one which survives and/or grows in the presence of a particular carbon source, nitrogen source, amino acid, mineral, salt, vitamin, or combination thereof but through adaptation in culture or genetic modification, has become a methanogenic microorganism which survives and/or grows in the substantial absence thereof. Alternatively or additionally, in some embodiments, the methanogenic microorganism before adaptation in culture or genetic modification, is one which survives and/or grows in the presence of a particular amount or concentration of carbon source, nitrogen source, amino acid, mineral, salt, vitamin, but through adaptation in culture or genetic modification, has become a methanogenic microorganism which survives and/or grows in a different amount or concentration thereof.

In some embodiments, the methanogenic microorganisms are adapted to a particular growth phase or state. Furthermore, for example, the methanogenic microorganism in some embodiments is one which, before adaptation in culture or genetic modification, is one which survives and/or grows in a given pH range, but through adaptation in culture becomes a methanogenic microorganism that survives and/or grows in a different pH range. In some embodiments, the methanogenic microorganisms are adapted in culture to a nearly stationary growth phase in a pH range of about 3.5 to about 10 (e.g., about 5.0 to about 8.0, about 6.0 to about 7.5). Accordingly, in some aspects, the methanogenic microorganisms are adapted in culture to a nearly stationary growth phase at a pH of about 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. In some embodiments, the methanogenic microorganisms are adapted in culture to an active growth phase in a pH range of about 6.5 to about 7.5 (e.g., about 6.8 to about 7.3). Accordingly, in some aspects, the methanogenic microorganisms are adapted in culture to a nearly stationary growth phase at a pH of about 6.5, 6.6, 6.7, 6.8, 6.9, 7.0, 7.1, 7.2, 7.3, 7.4, or 7.5.

As used herein, the term "adaptation in culture" refers to a process in which microorganisms are cultured under a set of desired culture conditions (e.g., high salinity, high temperature, substantial absence of any carbon source, low pH, etc.), which differs from prior culture conditions. The culturing under the desired conditions occurs for a period of time which is sufficient to yield modified microorganisms (progeny of the parental line (i.e. the unadapted microorganisms)) which survive and/or grow (and/or produce methane) under the desired condition(s). The period of time of adaptation in some aspects is 1 day, 2 days, 3 days, 4 days, 5 days, 6 days, 7 days, 8 days, 9 days, 10 days, 11 days, 12 days, 13 days, 2 weeks, 3 weeks 4 weeks, 5 weeks, 6 weeks, 1 month, 2 months, 3 months, 4 months, 5 months 6 months, 7 months, 8 months, 9 months, 10 months, 12 months, 1 year, 2 years. The process of adapting in culture selects for microorganisms that can survive and/or grow and/or produce methane in the desired culture conditions; these selected microorganisms remain in the culture, whereas the other microorganisms that cannot survive and/or grow and/or produce methane in the desired culture conditions eventually die in the culture. In some embodiments, as a result of the adaptation in culture, the methanogenic microorganisms produce methane at a higher efficiency, e.g., at a ratio of the number of carbon dioxide molecules converted to methane to the number of carbon dioxide molecules converted to cellular materials which is higher than N:1, wherein N is a number greater than 20, as further described herein.

For purposes of the present invention, in some embodiments, the methanogenic microorganism (e.g., *Methanothermobacter thermautotrophicus* strain UC 120910) has been adapted in culture to survive and/or grow in a high salt and/or high conductivity culture medium. For example, the methanogenic microorganism which has been adapted in culture to survive and/or grow in a culture medium having a conductivity of about 5 mS/cm to about 100 mS/cm.

In alternative or additional embodiments, the methanogenic microorganism (e.g., *Methanothermobacter thermautotrophicus* strain UC 120910) has been adapted in culture to survive and/or grow at higher temperature (e.g., a temperature which is between about 1 and about 15 degrees C. greater than the temperature that the microorganisms survives and/or grows before adaptation). In exemplary embodiments, the methanogenic microorganisms are adapted to survive and/or grow in a temperature which is greater than 50° C., e.g., greater than 55° C., greater than 60° C., greater than 65° C., greater than 70° C., greater than 75° C., greater than 80° C., greater than 85° C., greater than 90° C., greater than 95° C., greater than 100° C., greater than 105° C., greater than 110° C., greater than 115° C., or greater than 120° C.

In some embodiments, the presently disclosed methanogenic microorganism (e.g., *Methanothermobacter thermautotrophicus* strain UC 120910) has been adapted in culture to grow and/or survive in conditions which are low in or substantially absent of any vitamins. In some aspects, the methanogenic microorganism (e.g., *Methanothermobacter thermautotrophicus* strain UC 120910) has been adapted in culture to grow and/or survive in conditions which are low in or substantially absent of any organic carbon source. In some embodiments, the methanogenic microorganism has been adapted in culture to grow and/or survive in conditions with substantially reduced amounts of carbon dioxide. In these embodiments, the methanogenic microorganisms may be adapted to exhibit an increased methanogenesis efficiency, producing the same amount of methane (as compared to the unadapted microorganism) with a reduced amount of carbon dioxide. In some embodiments, the methanogenic microorganism has been adapted in culture to survive in conditions which substantially lack carbon dioxide. In these embodiments, the methanogenic microorganisms may be in a dormant phase in which the microorganisms survive but do not produce detectable levels of methane. In some embodiments, the methanogenic microorganisms have been adapted to grow and/or survive in conditions which are low in or substantially absent of any hydrogen. In some embodiments, the methanogenic microorganisms have been adapted to grow and/or survive in conditions which are low in or substantially absent of any external source of water, e.g., the conditions depend only upon water produced by the metabolism of the organisms and do not comprise a step involving dilution with externally added water.

In exemplary embodiments, the methanogens are adapted in culture to a nearly stationary growth phase. Such methanogens favor methane production over cell growth as measured, e.g., by the ratio of the number of $CO_2$ molecules converted to methane to the number of $CO_2$ molecules converted to cellular materials (i.e., biomass). This ratio is increased as compared to unadapted methanogens (which may exhibit, e.g., a ratio ranging from about 8:1 to about 20:1). In exemplary embodiments, the methanogens are adapted in culture to a nearly stationary growth phase by being deprived of one or more nutrients otherwise required for optimal growth for a prolonged period of time (e.g., 1 week, 2 week, 3 weeks, 1 month, 2 months, 3 months, 4 months, 5 months, 6 months, 7 months, 8 months, 9 months, 10 months, 11 months, 1 year, 2 years, 3 years, 4 years, 5 years or more). In exemplary embodiments, the methanogens are deprived of inorganic nutrients (e.g., hydrogen or electrons) necessary for optimum growth. In exemplary embodiments, depriving the methanogens of hydrogen or electrons is achieved by sparging the media with an insert gas mixture such as $Ar:CO_2$ at a flow rate of 250 mL/min for several hours until neither hydrogen nor methane appear in the effluent gas stream. In exemplary embodiments, the methanogenic microorganisms have been adapted to a nearly stationary growth phase in conditions which are low in or substantially absent of any external source of water, e.g., the adaptation conditions do not comprise a dilution step.

In exemplary aspects, the methanogenic microorganism has been adapted in culture to grow and/or survive in the culture medium set forth herein as Medium 1 and/or Medium 2 or a medium which is substantially similar to Medium 1 or Medium 2.

In exemplary embodiments, the variant expresses a 16S rRNA which has at least or about 90% (e.g., at least or about 95%, at least or about 98%, at least or about 99%) sequence identity to the 16S rRNA of the parent microorganism (e.g., a microorganism of *Methanothermobacter thermautotrophicus* strain UC 120910). In exemplary embodiments, the variant expresses a 16S rRNA which has at least or about 90% (e.g., at least or about 95%, at least or about 98%, at least or about 99%) sequence identity to the 16S rRNA of a Delta H *M. thermautotrophicus*, which sequence is set forth herein as SEQ ID NO: 1. In exemplary embodiments, the variant expresses a 16S rRNA which has at least or about 90% (e.g., at least or about 95%, at least or about 98%, at least or about 99%) sequence identity to the 16S rRNA of the microorganism of *Methanothermobacter thermautotrophicus* strain UC 120910 and which has at least or about 90% (e.g., at least or about 95%, at least or about 98%, at least or about 99%) sequence identity to SEQ ID NO: 1.

Genetically Modified Archaea

In exemplary embodiments, the methanogenic microorganisms have been purposefully or intentionally genetically modified to become suitable, e.g., more suitable, for the purposes of the disclosure. Suitable microorganisms may also be obtained by genetic modification of non-methanogenic organisms in which genes essential for supporting autotrophic methanogenesis are transferred from a methanogenic microbe or from a combination of microbes that may or may not be methanogenic on their own. Suitable genetic modification may also be obtained by enzymatic or chemical synthesis of the necessary genes.

In exemplary embodiments, a host cell that is not naturally methanogenic is intentionally genetically modified to express one or more genes that are known to be important for methanogenesis. For example, the host cell in some aspects is intentionally genetically modified to express one or more coenzymes or cofactors involved in methanogenesis. In some specific aspects, the coenzymes or cofactors are selected from the group consisting of F420, coenzyme B, coenzyme M, methanofuran, and methanopterin, the structures of which are known in the art. In exemplary aspects, the organisms are modified to express the enzymes, well known in the art, that employ these cofactors in methanogenesis.

In exemplary embodiments, the host cells that are intentionally modified are extreme halophiles. In exemplary embodiments, the host cells that are intentionally modified are thermophiles or hyperthermophiles. In exemplary embodiments, the host cells that are intentionally modified are non-autotrophic methanogens. In some aspects, the host cells that are intentionally modified are methanogens that are not autotrophic. In some aspects, the host cells that are intentionally modified are cells which are neither methanogenic nor autotrophic. In other embodiments, the host cells that are intentionally modified are host cells comprising synthetic genomes. In some aspects, the host cells that are intentionally modified are host cells which comprise a genome which is not native to the host cell.

In some embodiments, the methanogenic microorganisms have been purposefully or intentionally genetically modified to express pili or altered pili, e.g., altered pili that promote cell adhesion to the cathode or other components of the electrobiological methanogenesis reactor or pili altered to become electrically conductive. Pili are thin filamentous protein complexes that form flexible filaments that are made of proteins called pilins. Pili traverse the outer membrane of microbial cells and can extend from the cell surface to attach to a variety of other surfaces. Pili formation facilitates such disparate and important functions as surface adhesion, cell-cell interactions that mediate processes such as aggregation, conjugation, and twitching motility. Recent in silico analyses of more than twenty archaeal genomes have identified a large number of archaeal genes that encode putative proteins resembling type IV pilins (Szabo et al. 2007, which is incorporated by reference herein in its entirety). The expression of several archaeal pilin-like proteins has since been confirmed in vivo (Wang et al. 2008; Zolghadr et al. 2007; Fröls et al. 2007, 2008, which are incorporated by reference herein in their entirety). The sequence divergence of these proteins as well as the differential expression of the operons encoding these proteins suggests they play a variety of roles in distinct biological processes.

Certain microorganisms such as *Geobacter* and *Rhodoferax* species, have highly conductive pili that can function as biologically produced nanowires as described in US 20060257985, which is incorporated by reference herein in its entirety. Many methanogenic organisms, including most of the *Methanocaldococcus* species and the *Methanotorris* species, have native pili and in some cases these pili are used for attachment. None of these organisms are known to have natively electrically conductive pili.

In exemplary embodiments of the disclosure, the pili of a methanogenic organism and/or surfaces in contact with pili of a methanogenic organism or other biological components are altered in order to promote cell adhesion to the cathode or other components of the electrobiological methanogenesis reactor. Pili of a methanogenic organism can be further engineered to optimize their electrical conductivity. Pilin proteins can be engineered to bind to various complexes. For example, pilin proteins can be engineered to bind iron, mimicking the pili of *Geobacter* species or alternatively, they can be engineered to bind a low potential fenedoxin-like iron-sulfur cluster that occurs naturally in many hyperthermophilic methanogens. The desired complex for a particular application will be governed by the midpoint potential of the redox reaction.

The microorganisms may be genetically modified, e.g., using recombinant DNA technology. For example, cell or strain variants or mutants may be prepared by introducing appropriate nucleotide changes into the organism's DNA. The changes may include, for example, deletions, insertions, or substitutions of, nucleotides within a nucleic acid sequence of interest. The changes may also include introduction of a DNA sequence that is not naturally found in the strain or cell type. One of ordinary skill in the art will readily be able to select an appropriate method depending upon the particular cell type being modified. Methods for introducing such changes are well known in the art and include, for example, oligonucleotide-mediated mutagenesis, transposon mutagenesis, phage transduction, transformation, random mutagenesis (which may be induced by exposure to mutagenic compounds, radiation such as X-rays, UV light, etc.), PCR-mediated mutagenesis, DNA transfection, electroporation, etc.

The ability of the pili of the methanogenic organisms to adhere to the cathode coupled with an increased ability to conduct electrons, enable the organisms to receive directly electrons passing through the cathode from the negative electrode of the power source. The use of methanogenic organisms with genetically engineered pili attached to the cathode will greatly increase the efficiency of conversion of electric power to methane.

Phenotypic Characteristics

In exemplary embodiments, "$CO_2$ conversion phenotypic characteristics" of a methanogen or *Methanothermobacter* microorganism refer to one or more of the following:

(1) capable of exhibiting a high methane production efficiency per molecule of carbon dioxide ($CO_2$);
(2) capable of exhibiting a high level of methane productivity (per molecule of supplied carbon dioxide);
(3) capable of exhibiting a high level of methane productivity (per gram of biomass produced);
(4) capable of exhibiting a doubling time of at least or about 72 hours (i.e., in a stationary phase or a nearly stationary phase);
(5) capable of requiring significantly less nutrients for maintenance and growth of the microorganisms Exemplary "$CO_2$ conversion phenotypic characteristics" of a methanogen or *Methanothermobacter* microorganism may include one or more of the following:

(1) exhibiting a high methane production efficiency that is at least or about 25 $CO_2$ molecules converted to methane per $CO_2$ molecule converted to cellular material;

(2) producing at least or about 96 molecules of methane per 100 molecules of carbon dioxide supplied to the microorganism;

(3) producing at least or about 17 grams of methane per gram of cellular material produced.

In exemplary embodiments, "phenotypic characteristics" of a methanogen or *Methanothermobacter* microorganism refers to one or more of the following:

(a) capable of exhibiting a methane production efficiency that is at least or about 25 $CO_2$ molecules converted to methane per $CO_2$ molecule converted to cellular material; or (b) capable of surviving with a doubling time of at least or about 72 hours (i.e., in a stationary phase or a nearly stationary phase); or (c) capable of exhibiting a cell culture density of at least or about 6 mg dry mass of cells/ml culture in a stationary phase or nearly stationary phase; or (d) capable of returning to at least 80% of the methane productivity level in the operating state within 20 minutes, after an exposure of at least or about 3 minutes to oxygen or carbon monoxide; or (e) a combination (e.g., a combination of (a)-(d) or a sub-combination of (a) to (d)) thereof.

In exemplary embodiments, "phenotypic characteristics" of the methanogen or *Methanothermobacter* microorganism refers to (1) autotrophic and either thermophilic or hyperthermophilic; and (2) capable of returning to at least 80% (e.g., 90%, 95%, 98%) of the methane productivity level in the operating state within 20 minutes, after an exposure of at least 10 minutes to oxygen (e.g. oxygen in ambient air) or carbon monoxide;

and any one or more of the following:

(3) capable of exhibiting a methane production efficiency that is at least or about 25 $CO_2$ molecules converted to methane per $CO_2$ molecule converted to cellular material (e.g., at least or about 40, 50, 60, or 70 $CO_2$ molecules converted to methane per $CO_2$ molecule converted to cellular material), optionally while exhibiting a doubling time of at least or about 72 hours;

(4) capable of surviving with a doubling time of at least or about 72 hours (e.g., a doubling time of at least or about 80, 90, or 100 hours) for at least 30 days (e.g., for at least about 1, 2, 3, 4, 5, 6, 7, 8, 9, 10, 11 or 12 months);

(5) capable of continuously maintaining the methane production efficiency of (3) for at least 30 days (e.g., for at least or about 6 months, at least or about 12 months), optionally with a doubling time of at least or about 72 hours (e.g., a doubling time of at least or about 80, 90, or 100 hours); and (6) capable of returning to at least 80% (e.g., 90%, 95%, 98%) of the methane productivity in the operating state within 20 minutes of re-supplying $H_2$ gas or electricity, after being in a dormant state for at least 2 hours as induced by interrupting or ceasing $H_2$ gas supply or electricity.

In exemplary aspects, the *Methanothermobacter* microorganism is (1) autotrophic and either thermophilic or hyperthermophilic; and (2) capable of returning to at least 80% (e.g., 90%, 95%, 98%) of the methane productivity level in the operating state within 20 minutes, after an exposure of at least 10 minutes to oxygen (e.g. oxygen in ambient air) or carbon monoxide; and any one or more of the following:

(3) capable of exhibiting a methane production efficiency that is at least or about 40 $CO_2$ molecules converted to methane per $CO_2$ molecule converted to cellular material (e.g., at least or about 70 $CO_2$ molecules converted to methane per $CO_2$ molecule converted to cellular material), optionally while exhibiting a doubling time of at least or about 100 hours;

(4) capable of surviving with a doubling time of at least or about 100 hours for at least 6 months (e.g., for at least about 7, 8, 9, 10, 11 or 12 months);

(5) capable of continuously maintaining the methane production efficiency of (3) for at least 30 days (e.g., for at least or about 6 months, at least or about 12 months), optionally while in a stationary phase or a nearly stationary phase having a doubling time of at least or about 100 hours; and (6) capable of returning to at least 80% (e.g., 90%, 95%, 98%) of the methane productivity in the operating state within 10 minutes of re-supplying $H_2$ gas or electricity, after being in a dormant state for at least 2 hours as induced by interrupting or ceasing $H_2$ gas supply or electricity.

Autotrophic. In exemplary aspects, the microorganisms of the disclosure are autotrophic. As used herein, the term "autotrophic" refers to a microorganism capable of using carbon dioxide, formic acid, and/or carbon monoxide, and a source of reducing power to provide all carbon and energy necessary for growth and maintenance of the cell (e.g., microorganism). Suitable sources of reducing power may include but are not limited to hydrogen, hydrogen sulfide, sulfur, formic acid, carbon monoxide, reduced metals, sugars (e.g., glucose, fructose), acetate, photons, or cathodic electrodes or a combination thereof. In exemplary aspects, the autotrophic microorganisms of the disclosure obtains reducing power from a cathode or hydrogen.

Thermophilic or Hyperthermophilic. In exemplary aspects, the microorganisms of the disclosure are thermophilic or hyperthermophilic. As used herein, the term "thermophilic" refers to an organism which has an optimum growth temperature of about 50° C. or more, e.g., within a range of about 50° C. to about 80° C., about 55° C. to about 75° C., or about 60° C. to about 70° C. (e.g., about 60° C. to about 65° C., about 65° C. to about 70° C.). As used herein, the term "hyperthermophilic" refers to organism which has an optimum growth temperature of about 80° C. or more, e.g., within a range of about 80° C. to about 105° C.

Resilience to Oxygen or Carbon Monoxide. Methanogenic organisms are regarded as extremely strict anaerobes. Oxygen is known as an inhibitor of the enzyme catalysts of both hydrogen uptake and methanogenesis. A low oxidation-reduction potential (ORP) in the growth medium is regarded as important to methanogenesis. In exemplary embodiments, the *Methanothermobacter* microorganism of the disclosure is substantially resilient to oxygen exposure, inasmuch as the microorganism returns to a methane productivity level which is substantially the same as the methane productivity level exhibited before oxygen exposure within a relatively short period of time. In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before oxygen exposure) within 10 minutes after an exposure of at least 3 minutes to oxygen (e.g. oxygen in ambient air). In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before oxygen exposure) within 10 minutes after an exposure of at least 4 minutes to oxygen (e.g. oxygen in ambient air). In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before oxygen exposure) within 10 minutes after an exposure of at least 5 minutes to oxygen (e.g. oxygen in ambient air). In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before oxygen exposure) within 10 minutes after an exposure of at least 6 minutes to oxygen (e.g. oxygen in ambient air). In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before oxygen exposure) within 10 minutes after an exposure of at least 7 minutes to oxygen (e.g. oxygen in ambient air). In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before oxygen exposure) within 10 minutes after an exposure of at least 8 minutes to oxygen (e.g. oxygen in ambient air). In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before oxygen exposure) within 10 minutes after an exposure of at least 9 minutes to oxygen (e.g. oxygen in ambient air). In exemplary embodiments, the microorganism of the disclosure is capable of returning to a level of methane productivity level which is 100% of the methane productivity level in the operating state (e.g., before oxygen exposure) within 10 minutes after an exposure of at least 3 minutes to oxygen (e.g. oxygen in ambient air). In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before oxygen exposure) within 20 minutes after an exposure of at least 10 minutes to oxygen (e.g. oxygen in ambient air). In exemplary embodiments, the microorganism of the disclosure is capable of returning to a level of methane productivity which is at least 80% (e.g., at least 85%, at least 90%, at least 95%, at least 98%, 100%) of the methane productivity level in the operating state (e.g., before oxygen exposure) within 10 minutes after an exposure of at least 10 minutes to oxygen (e.g. oxygen in ambient air). In exemplary embodiments, the microorganism of the disclosure is capable of returning to a level of methane productivity which is at least 80% (e.g., at least 85%, at least 90%, at least 95%, at least 98%, 100%) of the methane productivity level in the operating state (e.g., before oxygen exposure) within 5 minutes or within 2 minutes after an exposure of at least 10 minutes to oxygen (e.g. oxygen in ambient air). In exemplary aspects, the exposure to oxygen is at least 30 minutes, at least 60 minutes, at least 90 minutes, 2 hours, 4 hours, 6 hours, 8 hours, 10 hours, 15 hours, 24 hours, 48 hours, 72 hours, or more. In exemplary embodiments, the methane productivity level in the operating state is within a range of about 300 VVD to about 500 VVD. Resilience to oxygen exposure may be tested in accordance with methods known in the art or as described in Example 4.

Carbon monoxide (CO) is another known inhibitor of enzymes involved in both hydrogen uptake and methanogenesis. In exemplary embodiments, the *Methanothermobacter* microorganism of the disclosure is substantially resilient to CO exposure, inasmuch as the microorganism returns to a methane productivity level which is substantially the same as the methane productivity level exhibited before CO exposure within a relatively short period of time. In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before CO exposure) within 20 minutes after an exposure of at least 10 minutes to CO. In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before CO exposure) within 10 minutes after an exposure of at least 3 minutes to CO. In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before CO exposure) within 10 minutes after an exposure of at least 4 minutes to CO. In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before CO exposure) within 10 minutes after an exposure of at least 5 minutes to CO. In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before CO exposure) within 10 minutes after an exposure of at least 6 minutes to CO. In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before CO exposure) within 10 minutes after an exposure of at least 7 minutes to CO. In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before CO exposure) within 10 minutes after an exposure of at least 8 minutes to CO. In exemplary embodiments, the microorganism of the disclosure is capable of returning to a level of methane productivity level which is at least 80% (e.g., at least 85%, at least 90%, at least 95%, at least 98%, 100%) of the methane productivity level in the operating state (e.g., before CO exposure) within 10 minutes after an exposure of at least 9 minutes to CO. In exemplary embodiments, the microorganism of the disclosure is capable of returning to a level of methane productivity level which is 100% of the methane productivity level in the operating state (e.g., before CO exposure) within 10 minutes after an exposure of at least 3 minutes to CO. In exemplary embodiments, the microorganism of the disclosure is capable of returning to a level of methane productivity which is at least 80% (e.g., at least 85%, at least 90%, at least 95%, at least 98%, 100%) of the methane productivity level in the operating state (e.g., before CO exposure) within 10 minutes after an exposure of at least 10 minutes to CO. In exemplary embodiments, the microorganism of the disclosure is capable of returning to a level of methane productivity which is at least 80% (e.g., at least 85%, at least 90%, at least 95%, at least 98%, 100%) of the methane productivity level in the operating state (e.g., before CO exposure) within 5 minutes or within 2 minutes after an exposure of at least 10 minutes to CO. In exemplary aspects, the exposure to CO is at least 30 minutes, at least 60 minutes, at least 90 minutes, 2 hours, 4 hours, 6 hours, 8 hours, 10 hours, 15 hours, 24 hours, 48 hours, 72 hours, or more. In exemplary embodiments, the methane productivity level in the operating state is within a range of about 300 VVD to about 500 VVD. Resilience to CO exposure may be tested in accordance with methods known in the art or as described in Example 4.

Methane Production Efficiency. It has been reported that naturally-occurring methanogenic microorganisms in the active growth phase produce methane at a ratio of about 8 $CO_2$ molecules converted to methane per molecule of $CO_2$ converted to cellular material, ranging up to a ratio of about 20 $CO_2$ molecules converted to methane per molecule of $CO_2$ converted to cellular material. In exemplary embodiments, the presently disclosed microorganisms demonstrate an increased efficiency, particularly when adapted in culture to stationary phase growth conditions. Accordingly, in exemplary aspects, the ratio of the number of $CO_2$ molecules converted to methane to the number of $CO_2$ molecules converted to cellular material of the disclosed microorganisms is higher than the ratio of naturally-occurring methanogenic microorganisms in the active growth phase. In exemplary embodiments, the ratio of the number of $CO_2$ molecules converted to methane to the number of $CO_2$ molecules converted to cellular material of the microorganisms of the disclosure is N:1, wherein N is a number greater than 20, e.g. about 25, 30, 35, 40, 45, 50, 55, 60, 65, 70, 75, 80, or higher. In some embodiments, N is less than 500, less than 400, less than 300, or less than 200. In some embodiments, N ranges from about 40 to about 150. In exemplary embodiments, the microorganism exhibits a methane production efficiency per molecule of carbon dioxide ($CO_2$) that is at least or about 25 $CO_2$ molecules converted to methane per $CO_2$ molecule converted to cellular material (e.g., at least or about 40, 50, 60, or 70 $CO_2$ molecules converted to methane per $CO_2$ molecule converted to cellular material). In exemplary embodiments, the microorganism exhibits a methane production efficiency per molecule of carbon dioxide ($CO_2$) that is at least or about 25 $CO_2$ molecules converted to methane per $CO_2$ molecule converted to cellular material (e.g., at least or about 40, 50, 60, or 70 $CO_2$ molecules converted to methane per $CO_2$ molecule converted to cellular material) while exhibiting a doubling time of at least or about 72 hours (e.g., a doubling time of at least or about 80, 90, or 100 hours). Methods of determining the number of carbon dioxide molecules converted to methane per carbon dioxide molecule converted to cellular material are known in the art and include the method described in Example 3.

In exemplary embodiments, the microorganism of the disclosure is capable of continuously maintaining for at least 30 days (e.g., for at least or about 6 months, at least or about 12 months) a methane production efficiency per molecule of carbon dioxide ($CO_2$) that is at least or about 25 $CO_2$ molecules converted to methane per $CO_2$ molecule converted to cellular material (e.g., at least or about 40 $CO_2$ molecules converted to methane per $CO_2$ molecule converted to cellular material, at least or about 70 $CO_2$ molecules converted to methane per $CO_2$ molecule converted to cellular material). In exemplary embodiments, the microorganism of the disclosure is capable of continuously maintaining for at least or about 12 months a methane production efficiency per molecule of carbon dioxide ($CO_2$) that is at least or about 70 $CO_2$ molecules converted to methane per $CO_2$ molecule converted to cellular material. In exemplary embodiments, the microorganisms of the disclosure are capable of continuously maintaining such a methane production efficiency, while in a stationary phase or a nearly stationary phase having a doubling time of at least or about 36 or 72 hours (e.g., a doubling time of at least or about 80, 90, 100, 240 hours).

In exemplary aspects, the microorganisms of the disclosure demonstrates a high level of methane productivity per molecule of supplied carbon dioxide. For example, the *Methanothermobacter* microorganism produces at least or about 96 molecules of methane per 100 molecules of carbon dioxide supplied to the microorganism. In exemplary aspects, the *Methanothermobacter* microorganism produces at least 96 (e.g., at least 96.0, 96.1, 96.2, 96.3, 96.4, 96.5, 96.6, 96.7, 96.8, 96.9, 97.0, 97.1, 97.2, 97.3, 97.4, 97.5, 97.6, 97.7, 97.8, 97.9, 98.0, 98.1, 98.2, 98.3, 98.4, 98.5, 98.6, 98.7, 98.9, 98.9, 99.0, 99.1, 99.2, 99.3, 99.4, 99.5, 99.6, 99.7, 99.8, or 99.9) molecules of methane per 100 molecules of carbon dioxide supplied to the microorganism. In exemplary aspects, the microorganism produces at least or about 96 molecules of methane per 100 molecules of carbon dioxide supplied to the microorganism when no more than 25 molecules of hydrogen are supplied to the microorganism for every 6 molecules of methane produced, or, optionally, no more than 200 molecules of hydrogen are supplied for every 49 molecules of methane produced.

In exemplary aspects, the microorganisms of the disclosure demonstrate a high level of methane productivity versus cellular material or biomass productivity. For example, the *Methanothermobacter* microorganism produces at least or about 17 grams of methane per gram of cellular material or biomass produced. In exemplary aspects, the *Methanothermobacter* microorganism produces at least 18 grams of methane per gram of cellular material or biomass produced. In exemplary aspects, the *Methanothermobacter* microorganism produces at least 19 grams of methane per gram of cellular material or biomass produced. In exemplary aspects, the *Methanothermobacter* microorganism produces at least 20 grams of methane per gram of cellular material or biomass produced. In exemplary aspects, the *Methanothermobacter* microorganism produces at least 25 grams of methane per gram of cellular material or biomass produced. In exemplary aspects, the *Methanothermobacter* microorganism produces at least 30 grams of methane per gram of cellular material or biomass produced. In exemplary aspects, the *Methanothermobacter* microorganism produces at least 35 grams of methane per gram of cellular material or biomass produced. In exemplary aspects, the *Methanothermobacter* microorganism produces at least 18 grams of methane per gram of cellular material or biomass produced. In exemplary aspects, the *Methanothermobacter* microorganism produces at least 40 grams of methane per gram of cellular material or biomass produced. In exemplary aspects, the microorganism produces at least or about 17 grams of methane per gram of biomass produced when no more than 25 molecules of hydrogen are supplied to the microorganism for every 6 molecules of methane produced, or, optionally, no more than 200 molecules of hydrogen are supplied for every 49 molecules of methane produced.

Operating States. The microorganisms of the disclosure may exist at any point in time in a dormant state or an operating state. As used herein, the term "dormant state" refers to a state in which the disclosed microorganisms are not producing methane (i.e., not producing methane at a detectable level). In exemplary aspects, the dormant state is induced by interrupting or ceasing (i.e., withholding) $H_2$ gas supply or electricity to the microorganism. As used herein, the term "operating state" refers to a state in which the disclosed microorganisms are producing methane (i.e., producing methane at a detectable level). In exemplary aspects, the operating state is induced by supplying (e.g., re-supplying) a $H_2$ gas supply or electricity to the microorganism.

In exemplary aspects, the microorganisms of the disclosure transition or cycle between an operating state and a dormant state. In exemplary aspects, the microorganisms of the disclosure transition or cycle between an operating state and a dormant state without decreasing its methane productivity level. In exemplary aspects, the microorganisms of the disclosure substantially maintain the methane productivity level of the operating state after transitioning out of a dormant state. As used herein, the term "substantially maintains the methane productivity level" refers to a methane productivity level which does not differ by more than 20% (e.g., within about 10% higher or lower) than a first methane productivity level. Accordingly, in exemplary aspects, the microorganisms of the disclosure are substantially resilient to being placed in a dormant state for a relatively long period of time, inasmuch as the microorganisms return to the methane productivity level exhibited before being placed in the dormant state within a relatively short period of time.

In exemplary aspects, after being in a dormant state for at least 2 hours as induced by interrupting or ceasing hydrogen supply or electricity, the microorganism of the disclosure is capable of returning to at least 80% (e.g., at least 85%, at least 90%, at least 95%, at least 98%, 100%) of the methane productivity in the operating state within 20 minutes of re-supplying hydrogen or electricity. In exemplary aspects, after being in a dormant state for at least 2 hours as induced by interrupting or ceasing hydrogen supply or electricity, the microorganism of the disclosure is capable of returning to at least 80% (e.g., at least 85%, at least 90%, at least 95%, at least 98%, 100%) of the methane productivity in the operating state within 10 minutes of re-supplying hydrogen or electricity. In exemplary aspects, after being in a dormant state for at least 2 hours as induced by interrupting or ceasing hydrogen supply or electricity, the microorganism of the disclosure is capable of returning to at least 80% (e.g., at least 85%, at least 90%, at least 95%, at least 98%, 100%) of the methane productivity in the operating state within 5 minutes or within 2 minutes of re-supplying hydrogen or electricity. In exemplary aspects, the microorganism is in a dormant state for at least 2 hours (e.g., at least 4 hours, 6 hours, 8 hours, 10 hours, 15 hours, 24 hours, 48 hours, 72 hours, or more) as induced by interrupting or ceasing hydrogen supply or electricity. In exemplary aspects, the microorganism is exposed to a condition in which the hydrogen supply or electricity is interrupted or ceased for a period of at least 2 hours (e.g., at least 4 hours, 6 hours, 8 hours, 10 hours, 15 hours, 24 hours, 48 hours, 72 hours, or more). In exemplary embodiments, the methane productivity level in the operating state is within a range of about 300 VVD to about 500 VVD.

Growth phases. When the microorganisms are in an operating state, the methanogenic microorganisms may be in one of a variety of growth phases, which differ with regard to the growth rate of the microorganisms (which can be expressed, e.g., as doubling time of microorganism number or cell mass). The phases of growth typically observed include a lag phase, an active growth phase (also known as exponential or logarithmic phase when microorganisms multiply rapidly), a stationary phase, and a death phase (exponential or logarithmic decline in cell numbers). In some embodiments, the microorganisms of the disclosure are in a lag phase, an active growth phase, a stationary phase, or a nearly stationary phase.

In some embodiments, the methanogenic microorganisms are in an active growth phase in which the methanogenic microorganisms are actively multiplying at a rapid rate. In some aspects, the doubling time of the microorganisms may be rapid or similar to that observed during the growth phase in its natural environment or in a nutrient-rich environment. For example, the doubling time of the methanogenic microorganisms in the active growth phase is about 15 minutes, about 20 minutes, about 30 minutes, about 45 minutes, about 60 minutes, about 75 minutes, about 80 minutes, about 90 minutes, or about 2 hours.

Stationary phase represents a growth phase in which, after the logarithmic or active growth phase, the rate of cell division and the rate of cell death are in equilibrium or near equilibrium, and thus a relatively constant concentration of microorganisms is maintained in the reactor. (See, Eugene W. Nester, Denise G. Anderson, C. Evans Roberts Jr., Nancy N. Pearsall, Martha T. Nester; Microbiology: A Human Perspective, 2004, Fourth Edition, Chapter 4, which is incorporated by reference herein in its entirety).

In exemplary embodiments, the methanogenic microorganisms are in an stationary growth phase or nearly stationary growth phase in which the methanogenic microorganisms are not rapidly growing or have a substantially reduced growth rate. In some embodiments, the doubling time of the methanogenic microorganisms is about 1 day or greater, including about 30 hours, 36 hours, 48 hours, 72 hours, 80 hours, 90 hours, 100 hours, 110 hours, 120 hours, 200 hours, 240 hours, 2, 3, 4, 5, 6, days or greater or about 1, 2, 3, 4 weeks or greater, or 1, 2, 3, 4, 5, 6, 7, 8, 9, 10, 11 or 12 months or greater.

In exemplary embodiments, the methanogenic microorganisms are capable of surviving in a stationary phase or a nearly stationary phase having a doubling time of at least or about 72 hours when provided with $CO_2$ gas at a rate of at least or about 34 VVD. In exemplary embodiments, the methanogenic microorganisms are capable of surviving in a stationary phase or a nearly stationary phase having a doubling time of at least or about 72 hours when provided with $CO_2$ gas at a rate of at least or about 34 VVD and with reducing power sufficient to reduce at least 90% of the $CO_2$. In exemplary aspects, the reducing power is hydrogen ($H_2$) gas supplied at a rate of at least 122 VVD. In exemplary aspects, the reducing power is electrical current.

In exemplary embodiments, the methanogenic microorganisms are capable of surviving in a stationary phase or a nearly stationary phase having a doubling time of at least or about 72 hours (e.g., a doubling time of at least or about 80, 90, or 100 hours) for a period of time which is at least 7 consecutive days (e.g., for at least about 1, 2, 3, 4, 5, 6, 7, 8, 9, 10, 11 or 12 months). In exemplary embodiments, the methanogenic microorganisms are capable of surviving in a stationary phase or a nearly stationary phase having a doubling time of at least or about 72 hours (e.g., a doubling time of at least or about 80, 90, or 100 hours) for a period of time which is at least 30 consecutive days (e.g., for at least about 1, 2, 3, 4, 5, 6, 7, 8, 9, 10, 11 or 12 months).

In exemplary embodiments, the methanogenic microorganisms are capable of surviving in a stationary phase or a nearly stationary phase having a doubling time of at least or about 72 hours (e.g., a doubling time of at least or about 80, 90, or 100 hours) for a period of time which is at least 30 days (e.g., for at least about 1, 2, 3, 4, 5, 6, 7, 8, 9, 10, 11 or 12 months).

In exemplary embodiments, the microorganism of the disclosure, while in a stationary phase or a nearly stationary phase having a doubling time of at least or about 36, 72 hours (e.g., a doubling time of at least or about 80, 90, 100, 240 hours), is capable of continuously maintaining for at least 30 days (e.g., for at least or about 6 months, at least or about 12 months) a methane production efficiency that is at least or about 25 $CO_2$ molecules converted to methane per $CO_2$ molecule converted to cellular material (e.g., at least or about 40 $CO_2$ molecules converted to methane per $CO_2$ molecule converted to cellular material, at least or about 70 $CO_2$ molecules converted to methane per $CO_2$ molecule converted to cellular material). In exemplary embodiments, the microorganism of the disclosure, while in a stationary phase or a nearly stationary phase having a doubling time of at least or about 100 hours, is capable of continuously maintaining for at least 12 months a methane production efficiency that is at least or about 70 $CO_2$ molecules converted to methane per $CO_2$ molecule converted to cellular material.

In exemplary embodiments, the methanogenic microorganisms are initially in an active growth phase and subsequently in a stationary or nearly stationary phase. In exemplary embodiments, when in an operating state, the methanogenic microorganisms cycle between an active growth phase and a stationary or nearly stationary phase. In exemplary aspects, the microorganisms of the disclosure transition or cycle between an active growth phase and a stationary or nearly stationary phase without decreasing its methane production efficiency, as described above.

Combinations of Phenotypic Characteristic. With regard to the above listing of phenotypic characteristics, (1) and (2) may be considered as required features of the microorganisms of the disclosure, while (3), (4), (5), and (6) may be considered as optional features of the microorganisms of the disclosure. In exemplary embodiments, the microorganisms of the disclosure exhibit (1), (2), (3), (4), (5), and (6). In exemplary aspects, the microorganism of the disclosure exhibits, in addition to (1) and (2), a combination of phenotypic characteristics selected from the group consisting of: [(3), (4), and (5)], [(3) and (4)], [(3)], [(3) and (5)], [(3) and (6)], [(4), (5), and (6)], [(4) and (5)], [(4)], [(4) and (6)], [(5) and (6)], [(5)], and [(6)]. All combinations and sub-combinations thereof are contemplated herein.

Additional phenotypic characteristics. In exemplary embodiments, the microorganisms of the disclosure exhibit additional phenotypic characteristics (in addition to the phenotypic characteristics set forth above as (1) to (6)).

In exemplary aspects, the microorganism is (i) capable of producing methane via hydrogenotrophic methanogenesis under the maximal hydrogen ($H_2$) gas supply conditions and in a fermenter as described in Example 2 at (a volume of methane at standard temperature and pressure produced per day) divided by the liquid volume of the culture (VVD) of at least about 300 VVD; (ii) capable of producing methane via electrobiological methanogenesis under the conditions and in a cell as described in Example 2 at a VVD of at least about 300 VVD; or a both of (i) and (ii). In exemplary embodiments, the microorganisms of the disclosure are capable of producing methane from carbon dioxide and $H_2$ gas via hydrogenotrophic methanogenesis. In exemplary embodiments, the microorganism is capable of producing methane via hydrogenotrophic methanogenesis under the maximal $H_2$ gas supply conditions and in a fermenter as described in Example 2 at a VVD of at least about 300 VVD (e.g., at least or about 500 VVD, at least or about 1000 VVD, at least or about 2000 VVD, at least or about 3000 VVD, at least or about 5000 VVD, at least or about 10,000 VVD. In exemplary aspects, the microorganism is capable of producing no more than 100,000 VVD under such conditions. In exemplary embodiments, the microorganisms of the disclosure are capable of producing methane from carbon dioxide, electricity, and water, via a process known as electrobiological methanogenesis. In exemplary embodiments, the microorganism is capable of producing methane via electrobiological methanogenesis under the conditions and in a cell as described in Example 2 at a VVD of at least about 300 VVD (e.g., at least or about 500 VVD, at least or about 1000 VVD, at least or about 2000 VVD, at least or about 3000 VVD, at least or about 5000 VVD, at least or about 10,000 VVD. In exemplary aspects, the microorganism is capable of producing no more than 100,000 VVD under such conditions. Methods of determining methane productivity in units of VVD are set forth in Example 2, for example.

The specific catalytic activity of methanogenic microorganisms can be expressed as the ratio of moles of methane formed per hour to moles of carbon in the microbial biomass formed per hour. Under some conditions, one of the necessary substrates may be limiting the reaction, in which case the specific catalytic capacity may exceed the measured specific catalytic activity. Thus, an increase in the limiting substrate would lead to an increase in the observed specific catalytic activity. Under other conditions, the observed specific catalytic activity may be saturated with substrate, in which case an increase in substrate concentration would not yield an increase in specific catalytic activity. Under substrate saturating conditions, the observed specific catalytic activity would equal the specific catalytic capacity. Methods of determining specific catalytic activity for methane production are described in Example 5, for example.

In exemplary embodiments, the microorganisms of the disclosure growing under steady state conditions (e.g., conditions as described in Example 1) are capable of exhibiting a specific catalytic capacity that is in excess of the specific catalytic activity that supports its growth. In exemplary embodiments, the specific catalytic activity of the microorganisms of the disclosure is at least 10 fold greater than observed during steady-state growth with doubling times in the range of 100 hours. In exemplary embodiments, the microorganism of the disclosure is capable of producing methane at a rate or an amount which is consistent with the increase in hydrogen or electricity supplied to the microorganisms. For example, in exemplary aspects, the microorganisms are capable of producing an X-fold increase in methane production in response to an X-fold increase in the supply of $H_2$ gas or electricity, wherein X is any number greater than 1, e.g., 2, 5, 10. In exemplary embodiments, when supplied with a 2-fold increase in hydrogen supply (e.g., from 0.2 L/min to 0.4 L/min), the microorganisms of the disclosure are capable of exhibiting a 2-fold increase in methane productivity.

In exemplary aspects, the microorganism of the disclosure exhibits additional resilience or resistance to exposure to contaminants other than oxygen or carbon monoxide, such as, for example, ethanol, sulfur oxides, and nitrogen oxides. In exemplary aspects, the microorganisms of the disclosure are capable of substantially returning to the methane productivity level after exposure to a contaminant selected from the group consisting of: ethanol, sulfur oxides, and nitrogen oxides. In exemplary aspects, the microorganisms of the disclosure are capable of returning to a methane productivity level which is at least 80% of the methane productivity level observed in the operating state within 20 minutes (e.g., within 10 minutes, within 5 minutes, within 2 minutes) after an exposure of at least 10 minutes to the contaminant.

Additionally, the microorganisms in exemplary embodiments exhibit phenotypic characteristics other than those described herein as (1) to (6) and (i) and (ii).

In exemplary aspects, the methanogenic microorganisms exhibit a cell culture density of at least or about 6 mg dry mass (e.g., 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg) of cells/ml culture in a stationary phase or nearly stationary phase. In exemplary aspects, the methanogenic microorganisms exhibit a cell culture density of at least or about 6 mg dry mass (e.g., 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg) of cells/ml culture in a stationary phase or nearly stationary phase for at least or about 15 consecutive days. In exemplary aspects, the methanogenic microorganisms exhibit a cell culture density of at least or about 6 mg dry mass (e.g., 6 mg, 7 mg, 8 mg, 9 mg, 10 mg, 11 mg, 12 mg. 13 mg, 14 mg, 15 mg, 16 mg, 17 mg, 18 mg, 19 mg, or 20 mg) of cells/ml culture in a stationary phase or nearly stationary phase for at least or about 20 consecutive days. In exemplary aspects, the methanogenic microorganisms exhibit a cell culture density of at least or about 6 mg dry mass (e.g., 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg) of cells/ml culture in a stationary phase or nearly stationary phase for at least or about 25 consecutive days. In exemplary aspects, the methanogenic microorganisms exhibit a cell culture density of at least or about 6 mg dry mass (e.g., 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg) of cells/ml culture in a stationary phase or nearly stationary phase for at least or about 30 consecutive days.

Cultures

The disclosure further provide cultures comprising a *Methanothermobacter* microorganism of the disclosure, e.g., a *Methanothermobacter* microorganism that is a microorganism of *Methanothermobacter thermautotrophicus* strain UC 120910, deposited on Dec. 21, 2010, with the American Type Culture Collection (ATCC) under ATCC® Patent Deposit Designation No. PTA-11561, a variant of a microorganism of *Methanothermobacter thermautotrophicus* strain UC 120910, or a progeny of a microorganism of *Methanothermobacter thermautotrophicus* strain UC 120910. The term "culture" as used herein refers to a population of live microorganisms in or on culture medium.

Monocultures, Substantially Pure Cultures

In some embodiments, the culture is a monoculture and/or is a substantially-pure culture. As used herein the term "monoculture" refers to a population of microorganisms derived or descended from a single species (which may encompass multiple strains) or a single strain of microorganism. The monoculture in some aspects is "pure," i.e., nearly homogeneous, except for (a) naturally-occurring mutations that may occur in progeny and (b) natural contamination by non-methanogenic microorganisms resulting from exposure to non-sterile conditions. Organisms in monocultures can be grown, selected, adapted, manipulated, modified, mutated, or transformed, e.g. by selection or adaptation under specific conditions, irradiation, or recombinant DNA techniques, without losing their monoculture nature.

As used herein, a "substantially-pure culture" refers to a culture that substantially lacks microorganisms other than the desired species or strain(s) of microorganism. In other words, a substantially-pure culture of a strain of microorganism is substantially free of other contaminants, which can include microbial contaminants (e.g., organisms of different species or strain). In some embodiments, the substantially-pure culture is a culture in which greater than or about 70%, greater than or about 75%, greater than or about 80%, greater than or about 85%, greater than or about 90%, greater than or about 91%, greater than or about 92%, greater than or about 93%, greater than or about 94%, greater than or about 95%, greater than or about 96%, greater than or about 97%, greater than or about 98%, greater than or about 99% of the total population of the microorganisms of the culture is a single, species or strain of methanogenic microorganism. By way of example, in some embodiments, the substantially-pure culture is a culture in which greater than 70%, 75%, 80%, 85%, 90%, 91%, 92%, 93%. 94%, 95%, 96%, 97%, 98%, 99% or more of the total population of microorganisms of the culture is a single methanogenic microorganism species, e.g., *Methanothermobacter thermautotrophicus*.

In exemplary embodiments, the culture initially is a pure or substantially pure monoculture. As the culture is exposed to non-sterile conditions, the culture may be contaminated by other non-methanogenic microorganisms in the environment without significant impact on methane production efficiency over a period of 1, 2, 3, 4, 5, 6, 7, 8, 9, 10, 11, 12 months, or 1.5 or 2 years.

Mixed Cultures

In other embodiments, the culture comprises a plurality of (e.g., a mixture or combination of two or more) different species of methanogenic microorganisms. In some aspects, the culture comprises two, three, four, five, six, seven, eight, nine, ten, or more different species of methanogenic microorganisms. In some aspects, the culture comprises a plurality of different species of methanogenic microorganisms, but the culture is substantially free of any non-methanogenic microorganism.

In yet other embodiments, the culture comprises a plurality of microorganisms of different species, in which at least one is a methanogenic microorganism of the disclosure. In some aspects of this embodiment, the culture comprises at least one of the disclosed methanogenic microorganisms and further comprises at least one selected non-methanogenic microorganism. In some aspects, the culture comprises two or more different species of methanogens, of which one is a disclosed methanogenic microorganism, and, optionally comprises at least one selected non-methanogenic microorganism.

Culture Media

The culture comprising the methanogenic microorganisms, e.g., the methanogenic archaea, may be maintained in or on a culture medium. In some embodiments, the culture medium is a solution or suspension (e.g., an aqueous solution). In other embodiments, the culture medium is a solid or semisolid. In yet other embodiments, the culture medium comprises or is a gel, a gelatin, or a paste.

In some embodiments, the culture medium is one that encourages the active growth phase of the methanogenic microorganisms. In exemplary aspects, the culture medium comprises materials, e.g., nutrients, in non-limiting amounts that support relatively rapid growth of the microorganisms. The materials and amounts of each material of the culture medium that supports the active phase of the methanogenic microorganisms will vary depending on the species or strain of the microorganisms of the culture. However, it is within the skill of the ordinary artisan to determine the contents of culture medium suitable for supporting the active phase of the microorganisms of the culture. In some embodiments, the culture medium encourages or permits a stationary phase of the methanogenic microorganisms. In some embodiments, a culture medium will support the active growth phase when microorgamisms have not reached or approached sufficient viable cell concentrations to inhibit the growth rate, through depletion of an essential nutrient and/or production of toxic metabolites, while the same culture medium will support a stationary or nearly stationary growth phase for the microorganism when the concentration of viable cells reaches a certain level, which one of skill in the art can readily determine empirically. Exemplary culture medium components and concentrations are described in further detail below. Using this guidance, alternative variations can be selected for particular species for electrobiological methanogenesis in the operating state of the biological reactor using well known techniques in the field.

Inorganic Materials: Inorganic Elements, Minerals, and Salts

In some embodiments, the medium for culturing archaea comprises one or more nutrients that are inorganic elements, or salts thereof. Common inorganic elements include but are not limited to sodium, potassium, magnesium, calcium, iron, chloride, sulfur sources such as hydrogen sulfide or elemental sulfur, phosphorus sources such as phosphate and nitrogen sources such as ammonium, nitrogen gas or nitrate. Exemplary sources include NaCl, NaHCO$_3$, KCl, MgCl$_2$, MgSO$_4$, CaCl$_2$, ferrous sulfate, Na$_2$HPO$_4$, NaH$_2$PO$_4$H$_2$O, H$_2$S, Na$_2$S, NH$_4$OH, N$_2$, and NaNO$_3$. In some embodiments, the culture medium further comprises one or more trace elements selected from the group consisting of ions of barium, bromine, boron, cobalt, iodine, manganese, chromium, copper, nickel, selenium, vanadium, titanium, germanium, molybdenum, silicon, iron, fluorine, silver, rubidium, tin, zirconium, cadmium, zinc, tungsten and aluminum. These ions may be provided, for example, in trace element salts, such as H$_3$BO$_3$, Ba(C$_2$H$_2$O$_2$)$_2$, KBr, CoCl$_2$-6H$_2$O, KI, MnCl$_2$-2H$_2$O, Cr(SO$_4$)$_3$-15H$_2$O, CuSO$_4$-5H$_2$O, NiSO$_4$-6H$_2$O, H$_2$SeO$_3$, NaVO$_3$, TiCl$_4$, GeO$_2$, (NH$_4$)$_6$Mo$_7$O$_{24}$-4H$_2$O, Na$_2$SiO$_3$-9H$_2$O, FeSO$_4$-7H$_2$O, NaF, AgNO$_3$, RbCl, SnCl$_2$, ZrOCl$_2$-8H$_2$O, CdSO$_4$-8H$_2$O, ZnSO$_4$-7H$_2$O, Fe(NO$_3$)$_3$-9H$_2$ONa$_2$WO$_4$, AlCl$_3$-6H$_2$O.

In some embodiments, the medium comprises one or more minerals selected from the group consisting of nickel, cobalt, sodium, magnesium, iron, copper, manganese, zinc, boron, phosphorus, sulfur, nitrogen, selenium, tungsten, aluminum and potassium including any suitable non-toxic salts thereof. Thus, in some embodiments, the minerals in the medium are provided as mineral salts. Any suitable salts or hydrates may be used to make the medium. For example, and in some embodiments, the media comprises one or more of the following mineral salts: Na$_3$ nitrilotriacetate, nitrilotriacetic acid, NiCl$_2$-6F$_2$O, CoCl$_2$-6H$_2$O, Na$_2$MoO$_4$—H$_2$O, MgCl$_2$-6H$_2$O, FeSO$_4$—H$_2$O, Na$_2$SeO$_3$, Na$_2$WO$_4$, KH$_2$PO$_4$, and NaCl. In some embodiments, L-cysteine may be added as a reduction-oxidation (redox) buffer to support early phases of growth of a low-density culture. In some embodiments, the medium comprises nickel, optionally NiCl$_2$-6H$_2$O in an amount of about 0.001 mM to about 0.01 mM, e.g. 0.002 mM, 0.003 mM, 0.004 mM, 0.005 mM, 0.006 mM, 0.007 mM, 0.008 mM, 0.009 mM, or any combination of the foregoing range endpoints. In some embodiments, the media comprises a nitrogen source, e.g., ammonium hydroxide or ammonium chloride in an amount of about 1 mM to about 10 mM, e.g. 2 mM, 3 mM, 4 mM, 5 mM, 6 mM, 7 mM, 8 mM, 9 mM, or any combination of the foregoing range endpoints. In some embodiments, the media comprises cobalt, e.g. CoCl$_2$-6H$_2$O, in an amount of about 0.001 mM to about 0.01 mM, e.g., 0.002 mM, 0.003 mM, 0.004 mM, 0.005 mM, 0.006 mM, 0.007 mM, 0.008 mM, 0.009 mM, or any combination of the foregoing range endpoints. In some embodiments, the media comprises molybdenum, a molybdenum source or molybdate, e.g. Na$_2$MoO$_4$—F$_2$O, in an amount of about 0.005 mM to about 0.05 mM, e.g., 0.006 mM, 0.007 mM, 0.008 mM, 0.009 mM, 0.01 mM, 0.02 mM, 0.03 mM, 0.04 mM, or any combination of the foregoing range endpoints. In some embodiments, the media comprises magnesium, e.g. MgCl$_2$-6H$_2$O, in an amount of about 0.5 mM to about 1.5 mM, e.g., 0.6 mM, 0.7 mM, 0.8 mM, 0.9 mM, 1.0 mM, 1.1 mM, 1.2 mM, 1.3 mM, 1.4 mM, or any combination of the foregoing range endpoints. In some embodiments, the media comprises iron, e.g. FeSO$_4$—H$_2$O, in an amount of about 0.05 mM to about 0.5 mM, e.g., 0.06 mM, 0.07 mM, 0.08 mM, 0.09 mM, 0.1 mM, 0.2 mM, 0.3 mM, 0.4 mM, or any combination of the foregoing range endpoints. In some embodiments, the media comprises a sulfur source or sulfate in an amount of about 0.05 mM to about 0.5 mM, e.g., 0.06 mM, 0.07 mM, 0.08 mM, 0.09 mM, 0.1 mM, 0.2 mM, 0.3 mM, 0.4 mM, or any combination of the foregoing range endpoints. In some embodiments, the media comprises selenium, a selenium source or selenate, e.g. Na$_2$SeO$_3$, in an amount of about 0.005 mM to about 0.05 mM, e.g., 0.006 mM, 0.007 mM, 0.008 mM, 0.009 mM, 0.01 mM, 0.02 mM, 0.03 mM, 0.04 mM, or any combination of the foregoing range endpoints. In some embodiments, the media comprises tungsten, a tungsten source or tungstate, e.g. Na$_2$WO$_4$, in an amount of about 0.005 mM to about 0.05 mM, e.g., 0.006 mM, 0.007 mM, 0.008 mM, 0.009 mM, 0.01 mM, 0.02 mM, 0.03 mM, 0.04 mM, or any combination of the foregoing range endpoints. In some embodiments, the media comprises potassium, e.g. KH$_2$PO$_4$, in an amount of about 5 mM to about 15 mM, e.g., 6 mM, 7 mM, 8 mM, 9 mM, 10 mM, 11 mM, 12 mM, 13 mM, 14 mM, or any combination of the foregoing range endpoints. In some embodiments, the media comprises phosphorus, a phosphorus source, or phosphate, e.g. KH$_2$PO$_4$, in an amount of about 5 mM to about 15 mM, e.g., 6 mM, 7 mM, 8 mM, 9 mM, 10 mM, 11 mM, 12 mM, 13 mM, 14 mM, or any combination of the foregoing range endpoints. In some embodiments, the media comprises NaCl in an amount of about 5 mM to about 15 mM, e.g., 6 mM, 7 mM, 8 mM, 9 mM, 10 mM, 11 mM, 12 mM, 13 mM, 14 mM, or any combination of the foregoing range endpoints.

In some embodiments, the microorganism is adapted to prefer high salt conditions, e.g. about 1.5M to about 5.5 M NaCl, or about 3 M to about 4 M NaCl. In some embodiments, the microorganism is adapted to growth in higher salt conditions than their normal environment.

In some embodiments, the culture medium serves more than one purpose. Accordingly, in some aspects, the culture medium supports the growth and/or survival of the microorganisms of the culture and serves as a cathode electrolytic medium within a bioreactor. An electrolyte is a substance that, when dissolved in water, permits current to flow through the solution. The conductivity (or specific conductance) of an electrolytic medium is a measure of its ability to conduct electricity. The SI unit of conductivity is siemens per meter (S/m), and unless otherwise qualified, it is measured at a standard temperature of 25° C. Deionized water may have a conductivity of about 5.5 μS/m, while sea water has a conductivity of about 5 S/m (i.e., sea water's conductivity is one million times higher than that of deionized water).

Conductivity is traditionally determined by measuring the AC resistance of the solution between two electrodes or by torroidal inductance meters.

Limiting ion conductivity in water at 298 K for exemplary ions:

| Cations | λ + 0/mS m$^2$mol$^{-1}$ | anions | λ − 0/mS m$^2$mol$^{-1}$ |
|---|---|---|---|
| H$^+$ | 34.96 | OH | 19.91 |
| Li$^+$ | 3.869 | Cl | 7.634 |
| Na$^+$ | 5.011 | Br | 7.84 |
| K$^+$ | 7.350 | I | 7.68 |
| Mg$^{2+}$ | 10.612 | SO42 | 15.96 |
| Ca$^{2+}$ | 11.900 | NO$_3$ | 7.14 |

In some embodiments, the culture medium comprises a high salt concentration for purposes of increasing the conductivity of the culture medium/reactor cathode electrolyte. Conductivity is readily adjusted, for example, by adding NaCl until the desired conductivity is achieved. In exemplary embodiments, the conductivity of the medium/electrolyte is in the range of about 5 mS/cm to about 100 mS/cm. This conductivity is readily achieved within the range of salt concentrations that are compatible with living methanogenic Archaea. In some embodiments, the conductivity of the medium/electrolyte is in the range of about 100 mS/cm to about 250 mS/cm, which is exemplary of a high conductivity medium.

Vitamins

In some embodiments, vitamins are substantially absent from the culture medium, to reduce contamination by non-methanogens and/or to decrease the cost of the culture medium, and thus, the overall cost of the biological reactor. However, it is possible to operate the biological reactor using media supplemented with one or more vitamins selected from the group consisting of ascorbic acid, biotin, choline chloride; D-Ca$^{++}$ pantothenate, folic acid, i-inositol, menadione, niacinamide, nicotinic acid, paraarninobenzoic acid (PABA), pyridoxal, pyridoxine, riboflavin, thiamine-HCl, vitamin A acetate, vitamin B$_{12}$ and vitamin D$_2$. In some embodiments, the medium is supplemented with a vitamin that is essential to survival of the methanogenic microorganism, but other vitamins are substantially absent.

Other Materials

The culture medium in some embodiments comprises materials other than inorganic compounds and salts. For example, the culture medium in some embodiments, comprises a chelating agent. Suitable chelating agents are known in the art and include but are not limited to nitrilotriacetic acid and/or salts thereof. Also, in some aspects, the culture medium comprises a redox buffer, e.g., cystine, to support an early active growth phase in a low-density culture.

Carbon Sources

In some aspects, the culture medium comprises a carbon source, e.g., carbon dioxide, formic acid, or carbon monoxide. In some embodiments, the culture medium comprises a plurality of these carbon sources in combination. In exemplary embodiments, organic carbon sources are substantially absent, to reduce contamination by non-methanogens.

Nitrogen Sources

In some embodiments, the culture medium comprises a nitrogen source, e.g., ammonium, anhydrous ammonia, ammonium salts and the like. In some embodiments, the culture medium may comprise nitrate or nitrite salts as a nitrogen source, although chemically reduced nitrogen compounds are preferable. In some aspects, the culture medium substantially lacks an organic nitrogen source, e.g., urea, corn steep liquor, casein, peptone yeast extract, and meat extract. In some embodiments diatomic nitrogen (N$_2$) may serve as a nitrogen source, either alone or in combination with other nitrogen sources.

Oxygen

Methanogens that are primarily anaerobic may still be capable of surviving prolonged periods of oxygen stress, e.g. exposure to ambient air for at least 6, 12, 18, or 24 hours, or 2 days, 3 days, 4 days, 5 days, 6 days, 1 week or more. Ideally, exposure to air is for 4 days or less, or 3 days or less, or 2 days or less, or 24 hours or less. Methane production may continue in the presence of oxygen concentrations as high as 2-3% of the gas phase for extended periods (at least days). However, anaerobic organisms will grow optimally in conditions of low oxygen. In some embodiments, the biological reactor substantially excludes oxygen to promote high levels of methane production.

In some embodiments, the system comprises various methods and/or features that reduce the presence of oxygen in the $CO_2$ stream that is fed into the biological reactor. When obligate anaerobic methanogenic microorganisms are used to catalyze methane formation, the presence of oxygen may be detrimental to the performance of the process and contaminates the product gas. Therefore, reduction of the presence of oxygen in the $CO_2$ stream is helpful for improving the process. In one embodiment, the oxygen is removed by pre-treatment of the gas stream in a biological reactor. In this embodiment, the reductant may be provided either by provision of a source of organic material (e.g. glucose, starch, cellulose, fermentation residue from an ethanol plant, whey residue, etc.) that can serve as substrate for an oxidative fermentation. The microbial biological catalyst is chosen to oxidatively ferment the chosen organic source, yielding $CO_2$ from the contaminant oxygen. In another embodiment, oxygen removal is accomplished in the main fermentation vessel via a mixed culture of microbes that includes one capable of oxidative fermentation of an added organic source in addition to the autotrophic methanogen necessary for methane production. An example of a suitable mixed culture was originally isolated as "*Methanobacillus omelianskii*" and is readily obtained from environmental sources (Bryant et al. Archiv Microbiol 59:20-31 (1967) "*Methanobacillus omelianskii*, a symbiotic association of two species of bacteria.", which is incorporated by reference herein in its entirety). In another embodiment, carbon dioxide in the input gas stream is purified away from contaminating gases, including oxygen, by selective absorption or by membrane separation. Methods for preparing carbon dioxide sufficiently free of oxygen are well known in the art.

Exemplary Media

In some embodiments, the culture medium comprises the following components: Na$_3$ nitrilotriacetate, nitrilotriacetic acid, NiCl$_2$-6H$_2$O, CoCl$_2$-6H$_2$O, Na$_2$MoO$_4$—H$_2$O, MgCl$_2$-

6H$_2$O, FeSO$_4$—H$_2$O, Na$_2$SeO$_3$, Na$_2$WO$_4$, KH$_2$PO$_4$, and NaCl. In some embodiments, cysteine may be added as a redox buffer to support early phases of growth of a low-density culture. In some embodiments, the media comprises Na$_3$ nitrilotriacetate (0.81 mM), nitrilotriacetic acid (0.4 mM), NiCl$_2$-6H$_2$O (0.005 mM), CoCl$_2$-6H$_2$O (0.0025 mM), Na$_2$MoO$_4$—H$_2$O (0.0025 mM), MgCl$_2$-6H$_2$O (1.0 mM), FeSO$_4$—H$_2$O (0.2 mM), Na$_2$SeO$_3$ (0.001 mM), Na$_2$WO$_4$ (0.01 mM), KH$_2$PO$_4$ (10 mM), and NaCl (10 mM). L-cysteine (0.2 mM) may be included.

In some embodiments, the culture medium comprises the following components: KH$_2$PO$_4$, NH$_4$Cl, NaCl, Na$_3$ nitrilotriacetate, NiCl$_2$-6H$_2$O, CoCl$_2$—H$_2$O, Na$_2$MoO$_4$-2H$_2$O, FeSO$_4$-7F$_2$O, MgCl$_2$-6H$_2$O, Na$_2$SeO$_3$, Na$_2$WO$_4$, Na$_2$S-9H$_2$O. A culture medium comprising these components may be referred to herein as Medium 1, which is capable of supporting survival and/or growth of methanogenic microorganisms originally derived from a terrestrial environment, e.g., a *Methanothermobacter* species. Thus, in some embodiments, the biological reactor comprises a culture of *Methanothermobacter* and a culture medium of Medium 1. In some aspects, the culture medium is adjusted with NH$_4$OH to a pH between about 6.8 and about 7.3. In some embodiments, the culture medium not only supports growth of and/or survival of and/or methane production by the methanogenic microorganisms but also serves as the cathode electrolytic medium suitable for conducting electricity within the reactor. Accordingly, in some aspects, the conductivity of the culture medium is in the range of about 5 mS/cm to about 100 mS/cm or about 100 mS/cm to about 250 mS/cm.

In some embodiments, the KH$_2$PO$_4$ is present in the medium at a concentration within the range of about 1 mM to about 100 mM, e.g., about 2 mM, about 50 mM, about 5 mM to about 20 mM.

In some embodiments, the NH$_4$Cl is present in the culture medium at a concentration within the range of about 10 mM to about 1500 mM, e.g., about 20 mM to about 600 mM, about 60 mM to about 250 mM.

In some embodiments, the NaCl is present in the culture medium within the range of about 1 mM to about 100 mM, e.g., about 2 mM, about 50 mM, about 5 mM to about 20 mM.

In some embodiments, the Na$_3$ nitrilotriacetate is present in the culture medium within the range of about 0.1 mM to about 10 mM, e.g., 0.20 mM to about 6 mM, about 0.5 to about 2.5 mM.

In some embodiments, the NiCl$_2$-6H$_2$O is present in the culture medium within the range of about 0.00025 to about 0.025 mM, e.g., about 0.005 mM to about 0.0125 mM, about 0.0005 mM to about 0.005 mM.

In some embodiments, the CoCl$_2$—H$_2$O is present in the culture medium within the range of about 0.0005 mM to about 0.05 mM, e.g., about 0.001 mM to about 0.025 mM, about 0.0025 mM to about 0.01 mM.

In some embodiments, the Na$_2$MoO$_4$-2H$_2$O is present in the culture medium within the range of about 0.00025 mM to about 0.025 mM, e.g., about 0.0005 mM to about 0.0125 mM, about 0.00125 mM to about 0.005 mM.

In some embodiments, the FeSO$_4$-7H$_2$O is present in the culture medium within the range of about 0.02 mM to about 2 mM, e.g., about 0.04 mM to about 1 mM, about 0.1 mM to about 0.4 mM.

In some embodiments, the MgCl$_2$-6H$_2$O is present in the culture medium within the range of about 0.1 mM to about 10 mM, e.g., about 0.2 mM to about 5 mM, about 0.5 mM to about 2 mM.

In some embodiments, the Na$_2$SeO$_3$ is present in the culture medium within the range of about 0.0001 mM to about 0.01 mM, e.g., about 0.0002 mM to about 0.005 mM, about 0.0005 mM to about 0.002 mM.

In some embodiments, the Na$_2$WO$_4$ is present in the culture medium within the range of about 0.001 mM to about 0.1 mM, e.g., about 0.05 mM to about 0.05 mM, about 0.005 mM to about 0.02 mM.

In some embodiments, Medium 1 is supplemented with components, such as sulfide, that support the active growth phase or relatively rapid multiplication of the microorganism. Accordingly, in some aspects, the culture medium comprises a higher sulfide concentration, e.g. 0.1 mM to about 10 mM (e.g., about 0.2 mM to about 5 mM, about 0.5 mM to about 2 mM), about 0.5 to 5 mM, or about 1 mM Na$_2$S-9H$_2$O, and preferably greater than 0.01 mM Na$_2$S-9H$_2$O, optionally with a pH between about 6.8 and about 7.0. In other embodiments, Medium 1 supports the stationary or nearly-stationary growth phase of the microorganism and the medium comprises a lower sulfide concentration. Accordingly, in some aspects, the culture comprises about 0.01 mM or less Na2S-9H2O, and not 1 mM Na2S-9H2O, optionally with a pH between about 7.2 and about 7.4.

In some embodiments, the culture medium comprises the following components: KH$_2$PO$_4$, NaCl, NH$_4$Cl, Na$_2$CO$_3$, CaCl$_2$×2H$_2$O, MgCl$_2$×6H$_2$O, FeCl$_2$×4H$_2$O, NiCl$_2$×6H$_2$O, Na$_2$SeO$_3$×5H$_2$O, Na$_2$WO$_4$×H$_2$O, MnCl$_2$×4H$_2$O, ZnCl$_2$, H$_3$BO$_3$, CoCl$_2$×6H$_2$O, CuCl$_2$×2H$_2$O, Na$_2$MoO$_4$×2H$_2$O, Nitrilotriacetic acid, Na$_3$ nitrilotriacetic acid, KAl(SO$_4$)$_2$×12H$_2$O, Na$_2$S×9H$_2$O. A culture medium comprising these components may be referred to herein as Medium 2, which is capable of supporting survival and/or growth of methanogenic microorganisms originally derived from a marine environment, e.g., a *Methanocaldooccus* species, *Methanotorris* species, *Methanopyrus* species, or *Methanotherinococcus* species. In some aspects, the culture medium is adjusted with NH$_4$OH to a pH between about 6.3 and about 6.8 (e.g., about 6.4 to about 6.6). In some embodiments, the culture medium not only supports growth of and/or survival of and/or methane production by the methanogenic microorganisms but also serves as the cathode electrolytic medium suitable for conducting electricity within the reactor. Accordingly, in some aspects, the conductivity of the culture medium is in the range of about 5 mS/cm to about 100 mS/cm or about 100 mS/cm to about 250 mS/cm.

In some embodiments, the KH$_2$PO$_4$ is present in the culture medium at a concentration within the range of about 0.35 mM to about 37 mM, e.g., about 0.7 mM to about 0.75 mM, about 1.75 mM to about 7.5 mM.

In some embodiments, the NaCl is present in the culture medium at a concentration within the range of about 17 mM to about 1750 mM, e.g., about 30 mM to about 860 mM, about 80 mM to about 350 mM.

In some embodiments, the NH$_4$Cl is present in the culture medium at a concentration within the range of about 0.7 mM to about 750 mM, e.g., about 1.5 mM to about 40 mM, about 3.75 mM to about 15 mM.

In some embodiments, the Na$_2$CO$_3$ is present in the culture medium at a concentration within the range of about 5 mM to about 600 mM, e.g., 10 mM to about 300 mM, about 30 mM to about 150 mM.

In some embodiments, the CaCl$_2$×2H$_2$O is present in the culture medium at a concentration within the range of about 0.05 to about 50 mM, e.g., 0.2 mM to about 5 mM, about 0.5 mM to about 2 mM.

In some embodiments, the MgCl$_2$×6H$_2$O is present in the culture medium at a concentration within the range of about 3 mM to about 350 mM, e.g., about 6.5 mM to about 175 mM, about 15 mM to about 70 mM.

In some embodiments, the $FeCl_2 \times 4H_2O$ is present in the culture medium at a concentration within the range of about 0.003 mM to about 0.3 mM, e.g., about 0.006 mM to about 0.15 mM, about 0.015 mM to about 0.06 mM.

In some embodiments, the $NiCl_2 \times 6H_2O$ is present in the culture medium at a concentration within the range of about 0.0005 mM to about 0.007 mM, e.g., 0.0012 mM to about 0.03 mM, about 0.003 mM to about 0.012 mM.

In some embodiments, the $Na_2SeO_3 \times 5H_2O$ is present in the culture medium at a concentration within the range of about 0.0001 mM to about 0.01 mM, e.g., about 0.00025 mM to about 0.01 mM, about 0.001 mM to about 0.005 mM.

In some embodiments, the $Na_2WO_4 \times H_2O$ is present in the culture medium at a concentration within the range of about 0.0005 mM to about 0.007 mM, e.g., 0.0012 mM to about 0.03 mM, about 0.003 mM to about 0.012 mM.

In some embodiments, the $MnCl_2 \times 4H_2O$ is present in the culture medium at a concentration within the range of about 0.003 mM to about 0.4 mM, e.g., about 0.08 mM to about 2 mM, about 0.02 mM to about 0.08 mM.

In some embodiments, the $ZnCl_2$ is present in the culture medium at a concentration within the range of about 0.0005 mM to about 0.007 mM, e.g., 0.0012 mM to about 0.03 mM, about 0.003 mM to about 0.012 mM.

In some embodiments, the $H_3BO_3$ is present in the culture medium at a concentration within the range of about 0.0001 mM to about 0.01 mM, e.g., about 0.00025 mM to about 0.01 mM, about 0.001 mM to about 0.005 mM.

In some embodiments, the $CoC_{l2} \times 6H_2O$ is present in the culture medium at a concentration within the range of about 0.0005 mM to about 0.007 mM, e.g., 0.0012 mM to about 0.03 mM, about 0.003 mM to about 0.012 mM.

In some embodiments, the $CuCl_2 \times 2H_2O$ is present in the culture medium at a concentration within the range of about 0.00004 mM to about 0.004 mM, e.g., 0.00008 mM to about 0.002 mM, about 0.0002 mM to about 0.0008 mM.

In some embodiments, the $Na_2MoO_4 \times 2H_2O$ is present in the culture medium at a concentration within the range of about 0.00004 mM to about 0.004 mM, e.g., 0.00008 mM to about 0.002 mM, about 0.0002 mM to about 0.0008 mM.

In some embodiments, the Nitrilotriacetic acid is present in the culture medium at a concentration within the range of about 0.003 mM to about 0.7 mM, e.g., about 0.12 mM to about 0.3 mM, about 0.03 mM to about 0.12 mM.

In some embodiments, the $Na_3$ nitrilotriacetic acid is present in the culture medium at a concentration within the range of about 0.002 mM to about 0.2 mM, e.g., about 0.004 mM to about 0.1 mM, about 0.01 mM to about 0.04 mM.

In some embodiments, the $KAl(SO_4)_2 \times 12H_2O$ is present in the culture medium at a concentration within the range of about 0.00004 mM to about 0.004 mM, e.g., 0.00008 mM to about 0.002 mM, about 0.0002 mM to about 0.0008 mM.

In some embodiments, the salt concentration in Medium 2 is adjusted upward to the range of 400 to 800 mM for formulation of the electrolyte in the reactor. Additionally, the sulfide concentration of relatively stationary cultures is adjusted downward to the range of <0.01 mM (<1 ppm sulfide in the exit gas stream).

In some examples, the media is sparged with a $H_2$: $CO_2$ gas mixture in a 4:1 ratio. The gas mixture can, in some embodiments, be generated with mass flow controllers at a total flow of 250 ml/minute. In some embodiments, the medium should be replenished at a rate suitable to maintain a useful concentration of essential minerals and to eliminate any metabolic products that may inhibit methanogenesis. Dilution rates below 0.1 culture volume per hour are suitable, since they yield high volumetric concentrations of active methane generation capacity.

Culture Conditions

The microorganisms may be cultured under any set of conditions suitable for the survival and/or methane production. Suitable conditions include those described below.

Temperature

In some embodiments, the temperature of the culture is maintained near the optimum temperature for growth of the organism used in the culture (e.g. about 60° C. to about 65° C. for thermophiles such as *Methanothermobacter thermautotrophicus* and *Methanothermobacter marburgensis*, and about 85° C. to about 90° C. for organisms such as *Methanocaldococcus jannaschii*, *Methanocaldococcus fervens*, *Methanocaldococcus indicus*, *Methanocaldococcus infernus*, and *Methanocaldococcus vulcanius*). However, it is envisioned that temperatures above or below the temperatures for optimal growth may be used. In fact, higher conversion rates of methane may be obtained at temperatures above the optimal growth rate temperature. Temperatures of about 50° C. or higher are contemplated, e.g., about 51° C. or higher, about 52° C. or higher, about 53° C. or higher, about 54° C. or higher, about 55° C. or higher, about 56° C. or higher, about 57° C. or higher, about 58° C. or higher, about 59° C. or higher, about 60° C. to about 150° C. about 60° C. to about 120° C., about 60° C. to about 100° C., about 60° C. to about 80° C. Temperatures of about 40° C. or higher, or about 50° C. or higher are contemplated, e.g. about 40° C. to about 150° C., about 50° C. to about 150° C., about 40° C. to about 120° C., about 50° C. to about 120° C., about 40° C. to about 100° C., or about 50° C. to about 100° C.

In view of the foregoing, the temperature at which the culture is maintained may be considered as a description of the methanogenic microorganisms contemplated herein. For example, when the temperature of the culture is maintained at a temperature between 55° C. and 120° C., the methanogenic microorganism is considered as one that can be cultured at this temperature. Accordingly, the methanogenic microorganism in some embodiments is a thermophile or a hyperthermophile. In some aspects, the culture comprises an autotrophic thermophilic methanogenic microorganism or an autotrophic hyperthermophilic methanogenic microorganism. In some aspects, the culture of the biological reactor comprises an autotrophic thermophilic methanogenic microorganism or an autotrophic hyperthermophilic methanogenic microorganism, either of which is tolerant to high conductivity culture medium (e.g., about 100 mS/cm to about 250 mS/cm), as described herein, e.g., a halophile.

Archaea may be capable of surviving extended periods at suboptimal temperatures. In some embodiments, cultured microorganisms of the disclosure are adapted to survive at room temperature (e.g. 22-28° C.) for a period of at least 3 weeks to 1, 2, 3, 4, 5 or 6 months.

In some embodiments, the organisms in the culture are not mesophilic. In some embodiments, the culture is not maintained at a temperature below or about 37° C. With respect to thermophilic or hyperthermophilic organisms (including, but not limited to, *Methanothermobacter thermautotrophicus*, *Methanothermobacter marburgensis*, *Methanocaldococcus jannaschii*, *Methanocaldococcus fervens*, *Methanocaldococcus indicus*, *Methanocaldococcus infernus*, and *Methanocaldococcus vulcanius*), in some embodiments, the temperature of the culture is e.g. about 60° C. to about 150° C., about 60° C. to about 120° C., about 60° C. to about 100° C., or about 60° C. to about 80° C.

pH

Microorganisms of the disclosure can be adapted to survive under a range of pH conditions. In some embodiments, the pH of the culture comprising methanogenic microorganisms is between about 3.5 and about 10.0, although for growth conditions, the pH may be between about 6.5 and about 7.5. For example, the pH of the culture may be about 3.5, about 3.6, about 3.7, about 3.8, about 3.9, about 4.0, about 4.5, about 5.0, about 5.5, about 6.0, about 6.5, about 7.0, about 7.5, about 8.0, about 8.5, about 9.0, about 9.5, about 10.0. In some embodiments, the pH of the media is acidic, e.g. about 0.1 to about 5.5, about 0.1 to about 4, about 0.1 to about 3, about 1 to about 3, or about 2 to about 3. In some embodiments, the pH of the media is close to neutral, e.g. about 6 to about 8. In some embodiments, the pH of the media is alkaline, e.g. about 8.5 to about 11, or about 8 to about 10. The pH of the media can be altered by means known in the art. For example, the pH can be controlled by sparging $CO_2$ and/or by adding acid (e.g., HCL) or base (e.g., NaOH or $NH_4OH$) as needed.

Pressure and Other Parameters

In some embodiments, the cultures are maintained in a culture vessel within a range from about 0.5 atmospheres to about 500 atmospheres. The culture can be maintained with a source of intermittent agitation, shaking, stirring, and the like. Also in exemplary embodiments, the methane gas removed from the culture suitably comprises less than about 450 ppm hydrogen sulfide, or alternatively less than about 400 ppm, 300 ppm, 200 ppm, 150 ppm, 100 ppm, 50 ppm or 20 ppm of hydrogen sulfide. Total gas delivery rates ($CO_2$) in the range of 0.2 to 4 volume of gas (STP) per volume of culture per minute are suitable, since they both maintain and exploit high volumetric concentrations of active methane generation capacity. In one embodiment, the redox potential is maintained below −100 mV or lower during methanogenesis. The method of the disclosure encompasses conditions in which the redox potential is transiently increased to above −100 MV, as for example when air is added to the system.

Culture Containers

A biological reactor, also known as a fermentor vessel, bioreactor, or simply reactor, as set forth herein may be any suitable vessel in which methanogenesis can take place. Suitable biological reactors should be sized relative to the volume of the $CO_2$ source. Typical streams of 2,200,000 lb $CO_2$/day from a 100,000,000 gal/yr ethanol plant would require a $CO_2$ recovery/methane production fermentor of about 750,000 gal total capacity. Fermentor vessels similar to the 750,000 gal individual fermentor units installed in such an ethanol plant would be suitable.

Culture Volume and Density

The concentration of living cells in the culture medium (culture density) is in some embodiments maintained above 1 g dry weight/L. In certain embodiments, the density may be 30 g dry weight/L or higher. The volume of the culture is based upon the pore volume within the porous cathode structure within the reactor, plus any volume needed to fill any ancillary components of the reactor system, such as pumps and liquid/gas separators.

Culture Medium for Reducing Contamination by Non-Methanogens

The term "non-methanogen" as used herein refers to any microorganism that is not a methanogen or is not a host cell expressing genes that permit methanogenesis. For example, in some embodiments, the archaea are cultured under conditions wherein the temperature, pH, salinity, sulfide concentration, carbon source, hydrogen concentration or electric source is altered such that growth of non-methanogens is significantly retarded under such conditions. For example, in some embodiments, the methanogens are cultured at a temperature that is higher than 37° C. In some aspects, the methanogenic microorganisms are cultured at a temperature of at least 50° C. or higher, as discussed herein, e.g., 100° C. or more, to avoid contamination by mesophilic non-methanogens. In other embodiments, the methanogens are cultured under conditions of high salinity (e.g., >75%) to avoid contamination by non-methanogens that are not capable of growing under high salt conditions. In still other embodiments, the methanogens are cultured under conditions in which the pH of the culture media is altered to be more acidic or more basic in order to reduce or eliminate contamination by non-methanogens that are not capable of growing under such conditions.

Contamination by non-methanogens can also be accomplished by minimizing amounts of organic carbon nutrients (e.g., sugars, fatty acids, oils, etc.) in the media. For example, in some embodiments, organic nutrients are substantially absent from the medium.

In some embodiments, components required for the growth of non-methanogenic organisms are substantially absent from the media. Such components include, but are not limited to, one or more organic carbon sources, and/or one or more organic nitrogen sources, and/or one or more vitamins. In some embodiments, formate, acetate, ethanol, methanol, methylamine, and any other metabolically available organic materials are substantially absent from the media.

In some embodiments, high salt conditions that permit survival of methanogens can retard growth of contaminating organisms.

In some embodiments, high temperatures that permit survival of methanogens can retard growth of contaminating organisms.

The term "substantially lacks" or "substantially absent" or "substantially excludes" as used herein refers to the qualitative condition of lacking an amount of a particular component significant enough to contribute to the desired function (e.g. growth of microorganisms, production of methane). In some embodiments, the term "substantially lacks" when applied to a given component of the media means that the media contains less than 5%, 4%, 3%, 2%, 1%, 0.9%, 0.8%, 0.7%, 0.6%, 0.5%, 0.4%, 0.3%, 0.2%, 0.1% or less of that component. In some embodiments, the media does not contain detectable amounts of a given component.

Systems

The disclosure furthermore provides a system or apparatus for converting carbon dioxide into methane including a supply of carbon dioxide, a source of reducing power, and a microorganism in accordance with the disclosure or a variant or progeny thereof, as described above.

In exemplary aspects, the source of reducing power (in whole or in part) is hydrogen, e.g., hydrogen ($H_2$) gas. Accordingly, in exemplary aspects, the system of the present disclosure includes a supply of carbon dioxide, a supply of hydrogen gas, and a microorganism in accordance with the disclosure or a variant or progeny thereof, as described herein.

In other exemplary aspects, the source of reducing power (in whole or in part) are electrons, e.g., hydronium ions. Accordingly, in exemplary aspects, the system comprises a biological reactor having at least a cathode, an anode, a supply of carbon dioxide, water, and a microorganism in accordance with the disclosure or a variant or progeny thereof, as described herein. In exemplary aspects, the biological reactor comprises at least a first chamber including the cathode, the microorganism, its variant or progeny, and water, and a second chamber including at least the anode. In exemplary aspects, in addition to the biological reactor, the system further includes a source of electricity coupled to the anode and the cathode, a supply of carbon dioxide coupled to the first chamber, and an outlet to receive methane from the first chamber.

Digester Embodiments

Using the microorganism described above, it may be possible to produce methane from electric power in a two-step process, such as outlined schematically in FIG. 1. The first step would use the electric power to make hydrogen gas from water in a standard water electrolysis system 50. In a second step, the hydrogen gas (to be used as the reducing power) could then be pumped into a methanogenic reaction chamber 52, such as a biological reactor as is described in greater detail in U.S. Publ. No. 2009/0130734 by Laurens Mets, which is incorporated in its entirety herein by reference.

Figure 2:
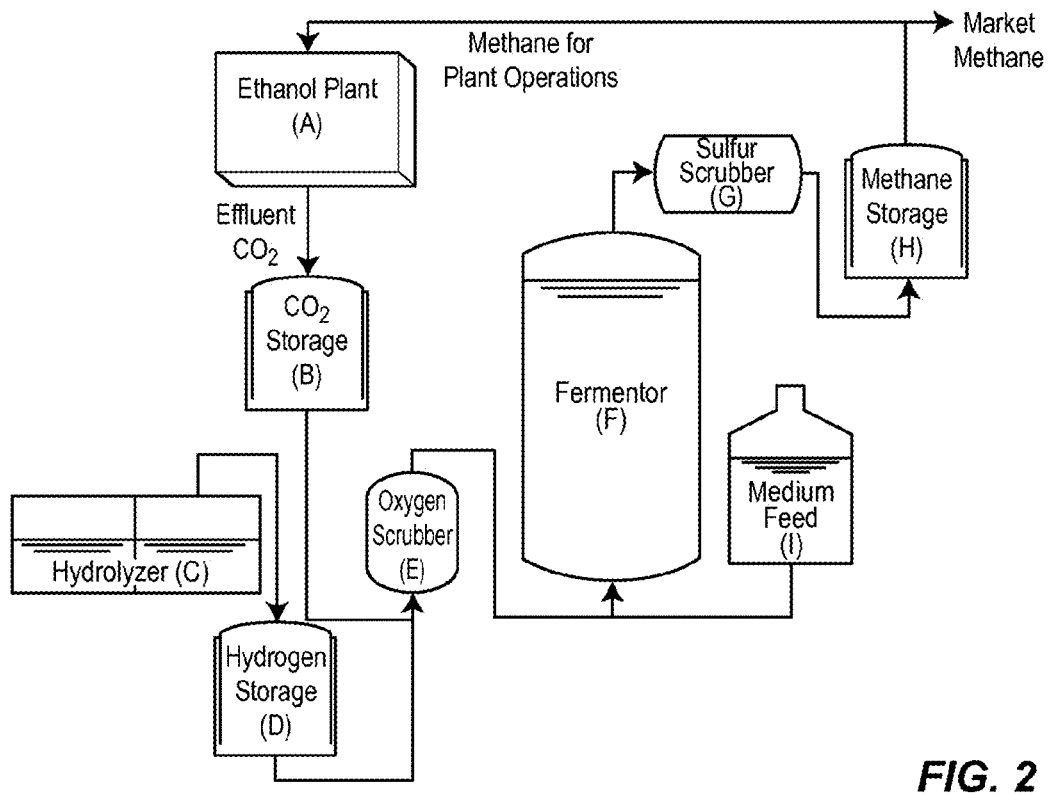
FIG. 2 is a schematic view of another system for converting carbon dioxide into methane using a digester.

In particular, FIG. 2 illustrates an embodiment of a plant using the microorganisms described above. An industrial carbon dioxide source (A)—e.g. fuel ethanol plant—with carbon dioxide effluent and natural gas demand, vents carbon dioxide to a carbon dioxide collection and storage tank (B), for example. A hydrolyzer (C) produces hydrogen, suitably from electrolysis. Hydrogen produce by the hydrolyzer (C) is collected in a hydrogen storage tank (D). The hydrogen and carbon dioxide from their respective storage tanks may be fed through an oxygen scrubber (E) for removal of oxygen from the carbon dioxide effluent stream. After passing through the oxygen scrubber (E), the hydrogen and carbon dioxide are fed into a digestor/fermentor/bioreactor system (F) for conversion of carbon dioxide and hydrogen to methane. A storage tank providing medium (I) is also connected to the system (F) to provide for replenishment of nutrients in the system (F). The methane gas vented from the system (F) passes through a sulfur scrubber (G) for recovering sulfur from the product methane stream. The methane gas can then be stored in a methane storage tank (H).

A bioreactor, also known as a digestor or fermentor vessel, as set forth in this disclosure is any suitable vessel in which methanogenesis can take place. Suitable bioreactors should be sized relative to the volume of the carbon dioxide source. Typical streams of 2,200,000 lb carbon dioxide/day from a 100,000,000 gal/yr ethanol plant would require a carbon dioxide recovery/methane production bioreactor of about 750,000 gal total capacity. Vessels similar to the 750,000 gal individual fermentor units typically installed in such an ethanol plant may thus be a suitable bioreactor.

Figure 3:
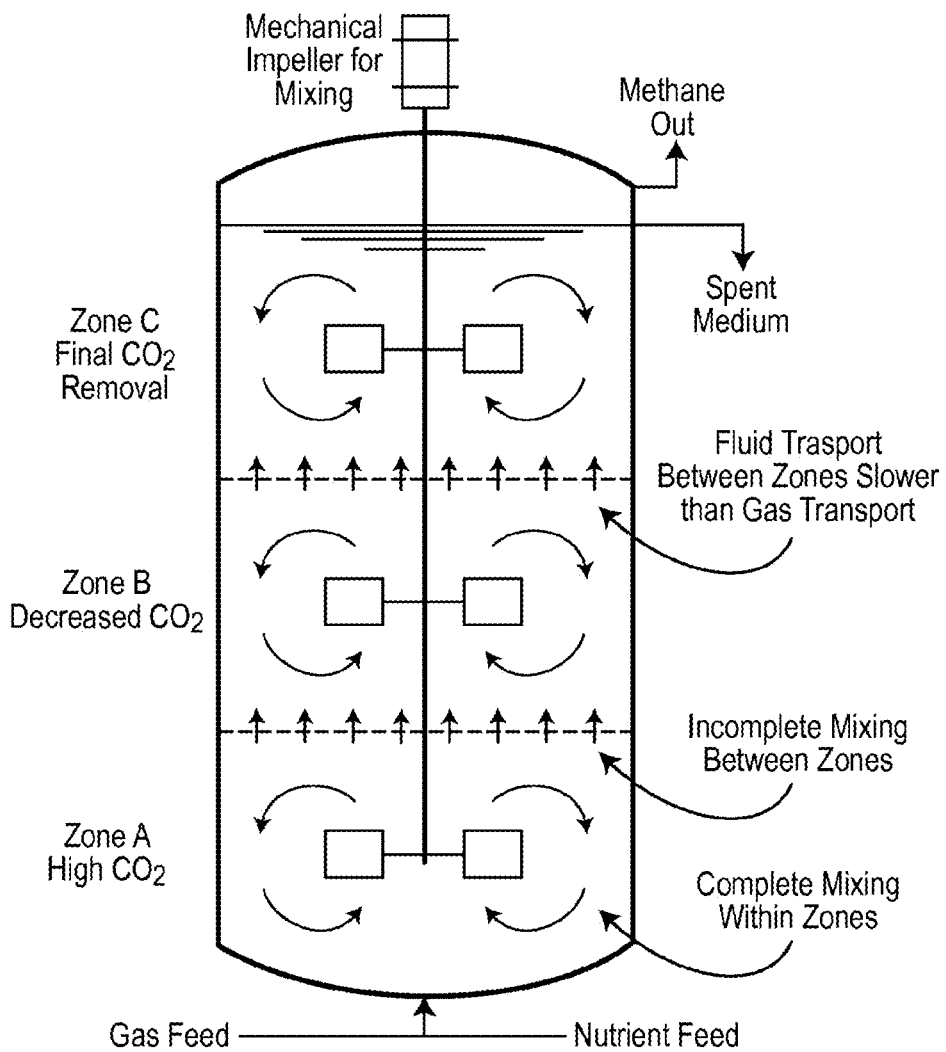
FIG. 3 is a schematic view of a stratified digester for use in the systems of FIGS. 1 and 2.

FIG. 3 illustrates an embodiment of a stratified bioreactor that can be used in the plant of FIG. 2, for example. In this embodiment, the bioreactor has the carbon dioxide and hydrogen entering into the bottom of the bioreactor along with the nutrients for the bioreactor. A mechanical impeller is positioned on the top of the bioreactor and is used to move a mixing apparatus within the bioreactor. The bioreactor has three zones, A, B and C. Zone A at the bottom of the reactor is a high carbon dioxide zone. Zone B, in the middle of the bioreactor has a decreased carbon dioxide presence, and Zone C at the top end of the reactor has little if any carbon dioxide. The methane produced, and the spent medium is removed from the top of the bioreactor.

Figure 4:
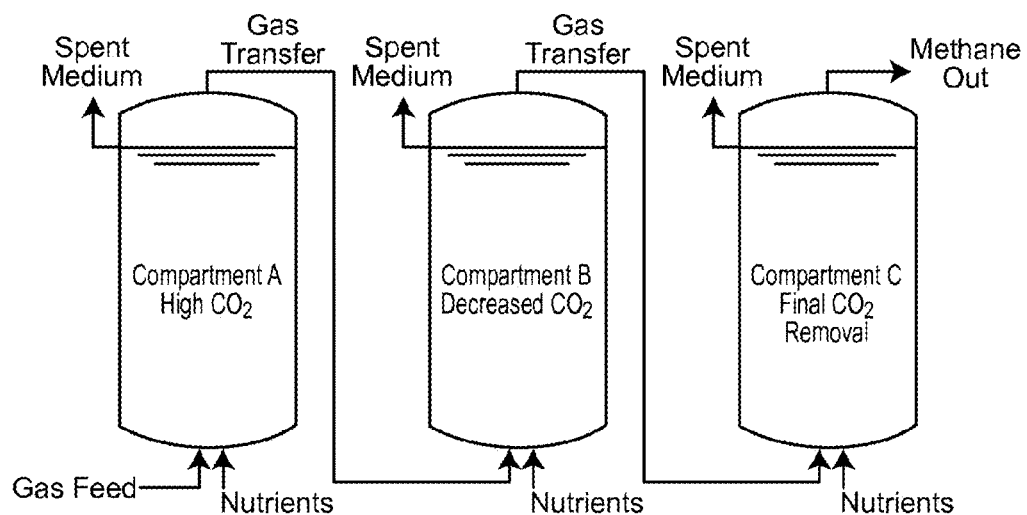
FIG. 4 is a schematic view of a set of cascaded digesters in serial arrangement.

FIG. 4 illustrates an embodiment of a cascaded bioreactor that may instead be used in the plant of FIG. 2. In this embodiment, the hydrogen, carbon dioxide and cell nutrients are fed into the bottom of a first compartment (A). In this compartment (A), even after processing, there is still a high level of carbon dioxide. The gas produced by the reaction in the first compartment (A) is then transferred from the top of the first compartment to the bottom of a second compartment (B) along with cell nutrients. In this second compartment (B), the carbon dioxide level is decreased from the levels found in the first compartment (A). The gas produced by the reaction in the second compartment (B) is transferred from the top of the second compartment (B) to the bottom of a third compartment (C) along with cell nutrients. In this third compartment (C), most (if not all) of the carbon dioxide has been removed and only the methane gas is left to be removed from the top of the compartment. In each of the compartments, spent medium can be removed from the compartments.

Biological Reactor Embodiments

In the alternative to the digester embodiments, it may be possible to use the microorganism described above to process or convert carbon dioxide into methane using an electro-biological apparatus. Systems and apparatuses of this category are further described in International Patent Application No. PCT/US2010/040944, filed Jul. 2, 2010, which is incorporated herein by reference in its entirety. The apparatus may be referred to herein as a biological reactor, bioreactor, processor, converter or generator. It will be recognized that this designation is not intended to limit the role that the converter may perform within a system including one or more converters.

For example, the apparatus provides a non-fossil carbon-based energy resource. In this regard, the apparatus is being used to generate an energy resource that may be substituted for fossil-based carbon fuels, to reduce reliance on fossil-based carbon fuels, for example. Additionally, the apparatus converts or processes carbon dioxide to generate this energy resource. In this regard, the apparatus removes carbon dioxide from the environment, which may be a beneficial activity in and of itself. Such removal of carbon dioxide from the environment may happen by removing carbon dioxide directly from the atmosphere or by utilizing carbon dioxide from another industrial process and thereby preventing such carbon dioxide from being released into the atmosphere or into a storage system or into another process. Further, the apparatus converts or processes carbon dioxide into methane using electricity to convert electricity into another energy resource when demand for electricity may be such that the electricity would otherwise be wasted or even sold at a loss to the electricity producer, for example. In this regard, the apparatus may be viewed as part of an energy storage system. In the operation of a power grid, or an individual power plant or other power source on the grid, or as part of a facility not associated with a power grid, or in the operation of a biological reactor, available power output may be used by one or more biological reactors to consume as an input carbon dioxide, water or electrical power and to produce methane or oxygen when business conditions are favorable to provide an incentive greater than for other use of such inputs. Such conditions may exist when certain regulatory policies, power purchase agreements, carbon credits, futures trading opportunities, storage capacity, electrical demand, taxes, tax credits or abatements, contracts, customer preferences, transmission capacity, pricing conditions, or other market incentives can provide sufficient value for operation of the biological reactor to produce methane or oxygen or to consume carbon dioxide, water or electrical power. In addition to the above and other uses, the apparatus converts electrical energy into methane which may be transmitted via natural gas transmission pipes which on a per unit energy basis are less expensive than electrical transmission lines and in some locales the electrical transmission lines may not have as much spare transmission capacity as the natural gas transmission lines. In this regard, the apparatus may be viewed as part of an energy transmission system. All of these roles may be performed by an apparatus according to the disclosure.

Figure 5:
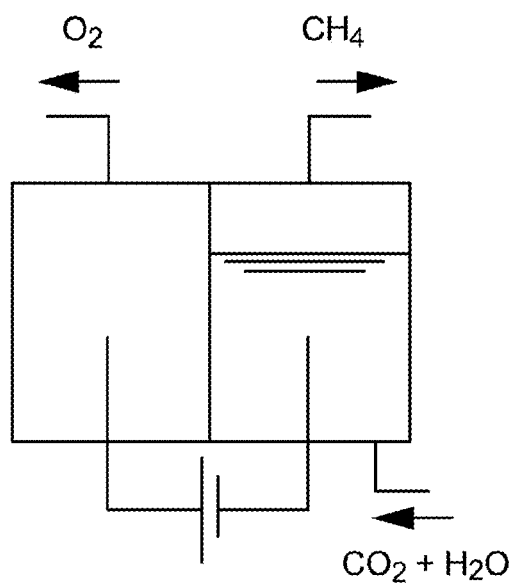
FIG. 5 is a schematic view of a system for converting carbon dioxide into methane using a biological or electro-biological reactor.

As illustrated in FIG. 5, the biological reactor according to the disclosure may include a container that is divided into at least a first chamber and a second chamber. At least one cathode is disposed in the first chamber, and at least one anode is disposed in the second chamber. The first chamber may have inlets that are connected to a source of carbon dioxide gas and a source of water, and an outlet that is connected, for example, to a storage device used to store methane produced in the first chamber. The first and second chambers are separated by a divider that is permeable to ions (protons) to permit them to move from the second chamber to the first chamber. This membrane also may be impermeable to the gaseous products and by-products of the conversion process to limit or prevent them from moving between the first chamber and the second chamber.

Methanogenic microorganisms may be cultured, for example, in shake or stirred tank bioreactors, hollow fiber bioreactors, or fluidized bed bioreactors, and operated in a batch, fed batch, continuous, semi-continuous, or perfusion mode. In batch mode (single batch), an initial amount of medium containing nutrients necessary for growth is added to the biological reactor, and the biological reactor is operated until the number of viable cells rises to a steady-state maximum, or stationary condition. In fed-batch mode, concentrated media or selected amounts of single nutrients are added at fixed intervals to the culture. Methanogenic microorganisms can survive for years under fed batch conditions, provided that any waste products are effectively minimized or removed to prevent loss of efficiency of methane production over time. Any inhibitory waste products may be removed by continuous perfusion production processes, well known in the art. Perfusion processes may involve simple dilution by continuous feeding of fresh medium into the culture, while the same volume is continuously withdrawn from the reactor. Perfusion processes may also involve continuous, selective removal of medium by centrifugation while cells are retained in the culture or by selective removal of toxic components by dialysis, adsorption, electrophoresis, or other methods. Continuously perfused cultures may be maintained for weeks, months or years.

Figure 6:
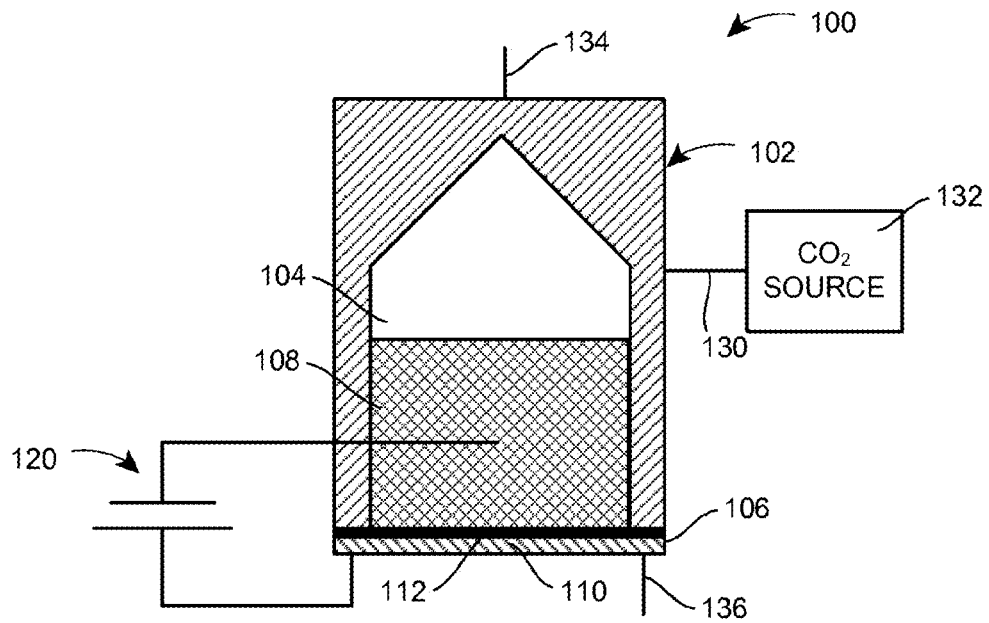
FIG. 6 is a cross-sectional view of an embodiment of a biological reactor for converting carbon dioxide into methane.

FIG. 6 illustrates a first embodiment of a system 100 that may be used, for example, to convert electric power into methane. The system 100 includes a biological reactor 102 having at least a first chamber 104 and a second chamber 106. The first chamber 104 may contain at least a cathode 108, a culture comprising living methanogenic microorganisms, and water. In particular, the culture may include the microorganisms described above, and the water may be part of an aqueous electrolyte medium compatible with the living microorganisms. The second chamber may contain at least an anode 110.

The biological reactor 102 may also include a proton permeable barrier 112. The barrier 112 may be at least gas semipermeable, although according to certain embodiments, the barrier 112 is impermeable to gases. According to certain embodiments, the impermeable barrier 112 may be a solid polymer electrolyte membrane (PEM), such as is available under tradename Nafion from E. I. du Pont de Nemours and Company. For optimum energy conversion in the reactor according to certain embodiments, it is believed that the permeability of the barrier to hydronium ions should preferably be a minimum of two orders of magnitude greater on a molar basis than permeability of the barrier to oxygen under conditions of operation of the reactor. Other suitable PEM membranes that meet these criteria, such as sulfonated polyarylene block co-polymers (see, e.g., Bae, B., K Miyatake, and M. Watanabe. Macromolecules 43:2684-2691 (2010), which is incorporated by reference herein in its entirety) and PTFE-supported Nafion (see, e.g., G.-B. Jung, et al, J Fuel Cell Technol 4:248-255(2007), which is incorporated by reference herein in its entirety), are under active development in numerous laboratories. Suitable commercial PEM membranes, in addition to Nafion, include Gore-Select (PRIMEA), Flemion (Asahi), 3M Fluoropolymer ionomer, SPEEK (Polyfuel), Kynar blended membrane (Arkema), Fumapem (FuMA-Tech), and Solupor (Lydall).

In the biological reactor 102, it is believed that the water acts as a net electron donor for the methanogenic microorganisms in the biological reactor. Accordingly, it is also believed that the barrier 112 should be permeable for hydronium ions ($H_3O+$). Nafion PEM is one example of a suitable material for such a barrier 112.

The cathode 108 may be made of a porous electrically conductive material. In particular, the cathode 108 may be made from a reticulated vitreous carbon foam according to certain embodiments. As explained in greater detail below, other materials may be used. According to certain embodiments, the pores of the cathode may be large enough (e.g., greater than 1-2 micrometers in minimum dimension) to accommodate living methanogenic microorganisms within the pores. The electrical conductivity of the cathode matrix is preferably at least two orders of magnitude greater than the ion conductivity of the aqueous electrolyte medium contained within its pores.

It will be recognized that the role of the cathode 108 is to supply electrons to the microorganisms while minimizing side-reactions and minimizing energy loss. Additionally, it is advantageous for the cathode to be inexpensive. At the present time, it is believed that certain materials may be more or less suitable for inclusion in the reactor.

For instance, platinum cathodes may be less suitable for inclusion in the reactor. In this regard, the platinum provides a surface highly active for catalyzing hydrogen gas production from the combination of protons or hydronium ions with electrons provided by the cathode. The activity of platinum cathode catalysts for hydrogen formation in aqueous solutions is so high that the hydrogen concentration in the vicinity of the catalyst quickly rises above its solubility limit and hydrogen gas bubbles emerge. Despite the fact that the methanogenic microorganisms are evolved to consume hydrogen in the process of methane formation, hydrogen in bubbles re-dissolves only slowly in the medium and is largely unavailable to the microorganisms. Consequently, much of the energy consumed in hydrogen formation at a platinum catalyst does not contribute to methane formation. Additionally, the binding energy of hydrogen is higher than the binding energy per bond of methane. This difference results in an energetic loss when hydrogen gas is produced as an intermediate step.

On the other hand, a solid carbon cathode is an example of an inexpensive, electrically conductive material that has low activity for hydrogen formation and that can provide electrons to microorganisms. However, it will be recognized that electron transfer between microorganisms and an external electron source or sink, such as an electrode, requires some level of proximity between the microorganisms and the electrode and the total rate of electron transfer is related to the area of electrode in close contact with microorganisms. Since a porous electrode that allows the microorganisms to enter the pores has a much larger surface area in proximity to the microorganisms than a planar electrode of equivalent dimensions, the porous electrode is expected to provide superior volumetric current density.

A suitable porous cathode material may be provided by reticulated vitreous carbon foam. It is inexpensive and conductive. Its porous structure provides for electrical connections to a large number of the microorganisms allowing for a high volumetric productivity. Additionally, the vitreous nature of the carbon provides low activity for hydrogen production, which increases both energetic and Faradaic efficiency. It will also be recognized that vitreous carbon is also very resistant to corrosion.

Other suitable porous electrode materials may include, but are not limited to graphite foam (see, e.g., U.S. Pat. No. 6,033,506, which is incorporated by reference herein in its entirety), woven carbon and graphite materials, carbon, graphite or carbon nanotube impregnated paper (see, e.g., Hu, L., et al. Proc Nat Acad Sci USA 106: 21490-4 (2009), which is incorporated by reference herein in its entirety), and metal foams, or woven or non-woven mesh comprised of materials, such as titanium, that are non-reactive under the conditions of the reaction and that present a high surface to volume ratio.

Further enhancement of electron transfer between the cathode and the microorganisms may be achieved with conductive fibers. Suitable conductive fibers may consist of conductive pili generated by the microorganisms as described in more detail above. Alternatively or additionally, nanowires, such as carbon nanotubes (Iijima, S. Nature 354:56 (1991), which is incorporated by reference herein in its entirety), may be attached directly to the cathode. Wang, J. et al, J. Am. Chem. Soc. 125:2408-2409 (2003) and references therein, all of which are incorporated by reference herein in their entirety, provide techniques for modifying glassy carbon electrodes with carbon nanotubes. Additionally, conductive organic polymers may be used for this purpose (see, e.g., Jiang, P. Angewandte Chemie 43:4471-4475 (2004), which is incorporated by reference herein in its entirety). Non-conductive materials that bind the microorganisms to the surface of the electrode may also enhance electron transfer. Suitable non-conductive binders include but are not limited to poly-cationic polymers such as poly-lysine or poly(beta-aminosulfonamides). The living methanogenic microorganisms may also produce biological materials, such as those that support biofilm formation, that effectively bind them to the surface of the electrode.

The anode 110 may comprise a Pt-carbon catalytic layer or other materials known to provide low overpotential for the oxidation of water to oxygen.

As illustrated in FIG. 6, a source of electricity 120 is coupled to the anode 110 and the cathode 108. As mentioned above, the source 120 may be generated from carbon-free, renewable sources. In particular, the source 120 may be generated from carbon-free, renewable sources such as solar sources (e.g., photovoltaic cell arrays) and wind sources (e.g., wind turbines). However, according to other embodiments, the source 120 may be a coal power plant, a fuel cell, a nuclear power plant. According to still further embodiments, the source 120 may be a connector to an electrical transmission grid.

The biological reactor 102 may operate at an electrical current density above 6 mA/cm$^2$. For example, the biological reactor 102 may operate at an electrical current density of between 6 and 10 mA/cm$^2$. According to certain embodiments, the biological reactor 102 may operate at electrical current densities at least one order of magnitude higher (e.g., 60-100 mA/cm$^2$). The current may be supplied as direct current, or may be supplied as pulsed current such as from rectified alternating current. The frequency of such pulsed current is not constrained by the properties of the reactor. The frequency of the pulsed current may be variable, such as that generated by variable speed turbines, for example wind turbines lacking constant-speed gearing The living methanogenic microorganisms may be impregnated into the cathode 108. Various embodiments and variants of the microorganisms are described in greater detail in the preceding section As explained in greater detail above, the biological reactor 102 may have an operating state wherein the culture is maintained at a temperature above 50° C., although certain embodiments may have an operating state in the range of between approximately 60° C. and 100° C. The biological reactor 102 may also have a dormant state wherein either electricity or carbon dioxide is not supplied to the reactor 102. According to such a dormant state, the production of methane may be significantly reduced relative to the operating state, such that the production may be several orders of magnitude less than the operating state, and likewise the requirement for input electrical power and for input carbon dioxide may be several orders of magnitude less than the operating state. According to certain embodiments of the disclosure, the biological reactor 102 may change between the operating state and the dormant state or between dormant state and operating state without addition of microorganisms to the reactor 102.

The biological reactor 102 may have an inlet 130 connected to the first chamber for receiving gaseous carbon dioxide. The inlet 130 may be coupled to a supply of carbon dioxide 132 to couple the supply of carbon dioxide to the first chamber 104. The biological reactor 102 may also have an outlet 134 to receive methane from the first chamber.

The biological reactor 102 may also have an outlet 136 connected to the second chamber 106 for receiving byproducts. For example, gaseous oxygen may be generated in the second chamber 106 as a byproduct of the production of methane in the first chamber 104. According to certain embodiments, oxygen may be the only gaseous byproduct of the biological reactor 102. In either event, the gaseous oxygen may be received by the outlet 134 connected to the second chamber 106.

In keeping with the disclosure of FIG. 6, a method of the disclosure may include supplying electricity to the anode 110 and the cathode 108 of the biological reactor 102 having at least the first chamber 104 containing at least the cathode 108, a culture comprising living methanogenic microorganisms as described above, and water (e.g., as part of an aqueous electrolyte medium compatible with the living microorganisms), and the second chamber 106 containing at least the anode 110, wherein the culture is maintained at a temperature above 50° C. Further, the method may include generating electricity from carbon-free, renewable sources, such as from solar and wind sources, as noted above. According to certain embodiments, electricity may be supplied during a non-peak demand period.

The method may also include supplying carbon dioxide to the first chamber 104. As noted above, the method may include recycling carbon dioxide from at least a concentrated industrial source or atmospheric carbon dioxide, which carbon dioxide is supplied to the first chamber 104.

The method may further include collecting methane from the first chamber 104. The method may further include storing and transporting the methane. The method may also include collecting other gaseous products or byproducts of the biological reactor; for example, the method may include collecting oxygen from the second chamber 106.

It will be recognized that while the system of FIG. 6 may be viewed as operating to convert electricity into methane, it is also possible to view the system of FIG. 6 as operating to create or earn carbon credits, as an alternative to carbon sequestration for example. According to such a method, the method would include supplying electricity to the anode 110 and the cathode 108 of biological reactor 102 having at least the first chamber 104 containing at least the cathode 108, methanogenic microorganisms, and water (e.g., as part of an aqueous electrolyte medium compatible with the living microorganisms), and a second chamber containing at least the anode, wherein the culture is maintained at a temperature above 50° C. The method would also include supplying carbon dioxide to the first chamber 104. Finally, the method would include receiving carbon credits for the carbon dioxide converted in the biological reactor 102 into methane. According to such a method, the carbon dioxide may be recycled from a concentrated industrial source.

It will be recognized that the system 100 is only one such embodiment of a system according to the disclosure. Additional embodiments and variants of the system 100 are illustrated in FIGS. 7-13, and will be described in the following section. While these embodiments are generally shown in cross-section, assuming a generally cylindrical shape for the reactor and disc-like shapes for the anode and cathode, which may be arranged parallel to one another as illustrated, it will be appreciated that other geometries may be used instead.

Figure 7:
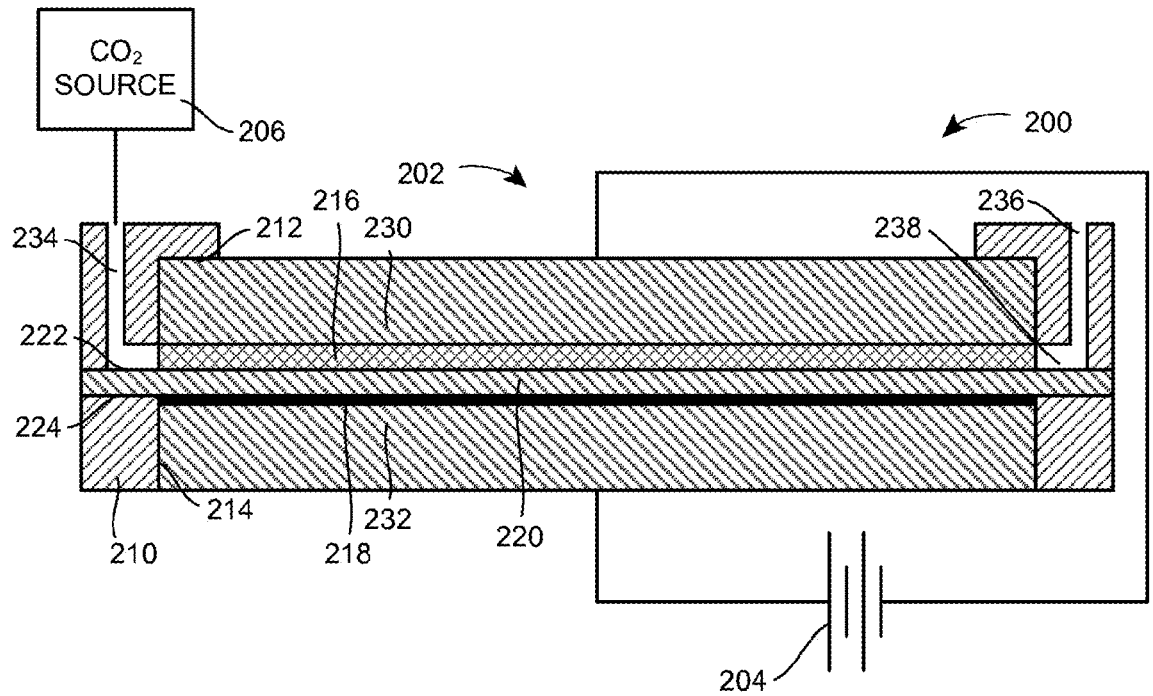
FIG. 7 is a cross-sectional view of another embodiment of a biological reactor for converting carbon dioxide into methane.

FIG. 7 illustrates a system 200 that includes a biological reactor 202, a source of electricity 204 and a source of carbon dioxide 206. As illustrated, the source of electricity 204 and the source of carbon dioxide 206 are both coupled to the biological reactor 202. The biological reactor 202 uses a circulating liquid/gas media, as explained in greater detail above.

The biological reactor 202 includes a housing 210 that defines, in part, first and second chambers 212, 214. The reactor 202 also includes a cathode 216 disposed in the first chamber 212, and an anode 218 disposed in the second chamber 214. The first and second chambers 212, 214 are separated by proton permeable, gas impermeable barrier 220, the barrier 220 having surfaces 222, 224 which also define in part the first and second chambers 212, 214.

The biological reactor 202 also includes current collectors 230, 232, one each for the cathode 216 and the anode 218. The current collector 230 for the cathode 216 may be made as a solid disc of material, so as to maintain a sealed condition within the chamber 212 between an inlet 234 for the carbon dioxide and an outlet 236 for the methane (and potentially byproducts). The inlet 234 and the outlet 236 may be defined in the housing 210. The current collector 232 for the anode 218 may also define a porous gas diffusion layer, on which the anode catalyst layer is disposed. It will be recognized that a porous gas diffusion layer should be provided so as to permit gaseous byproducts to exit the second chamber 214, because the barrier 220 prevents their exit through the outlet 236 via the first chamber 212.

In keeping with the disclosure above, the cathode 216 is made of a porous material, such as a reticulated carbon foam. The cathode 216 is impregnated with the methanogenic microorganisms and with the aqueous electrolyte medium. The methanogenic microorganisms are thus in a passage 238 formed between the barrier 220 and the current collector 230 between the inlet 234 and the outlet 236.

In operation, carbon dioxide is dissolved into the aqueous electrolyte medium and is circulated through the cathode 216. The methanogenic microorganisms may reside within the circulating electrolyte medium or may be bound to the porous cathode 216. In the presence of an electric current, the methanogenic microorganisms process the carbon dioxide to generate methane. The methane is carried by the electrolyte medium out of the reactor 202 via the outlet 236. According to such an embodiment, post-processing equipment, such as a liquid/gas separator, may be connected to the outlet to extract the methane from the solution.

Figure 8:
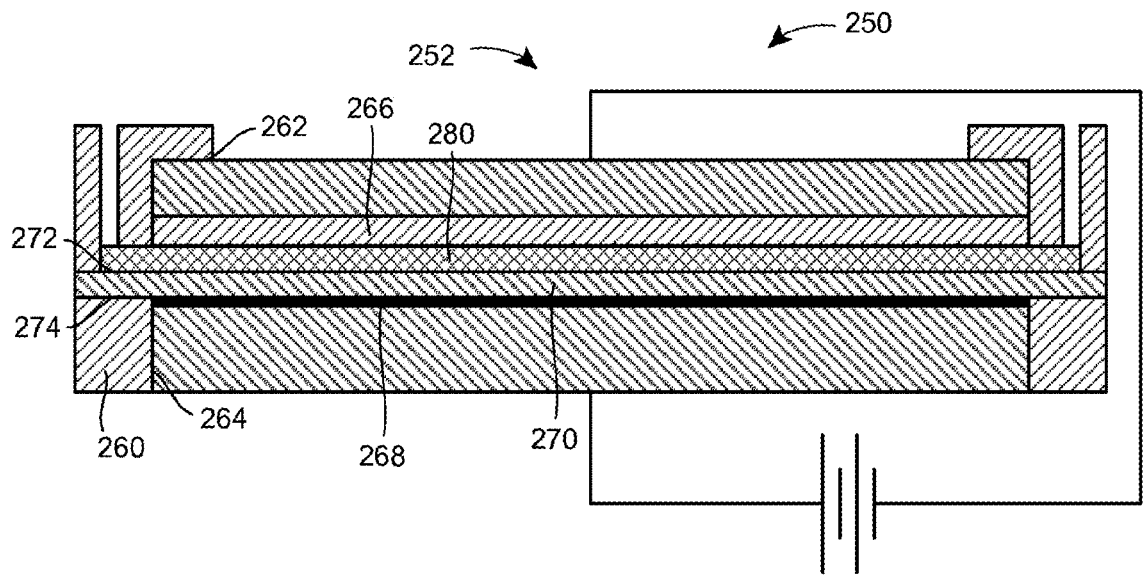
FIG. 8 is a cross-sectional view of yet another embodiment of a biological reactor for converting carbon dioxide into methane.

FIG. 8 illustrates a system 250 including a reactor 252 that is a variant of that illustrated in FIG. 7. Similar to the reactor 202, the reactor 252 includes a housing 260 that defines, in part, first and second chambers 262, 264. The reactor 252 also includes a cathode 266 disposed in the first chamber 262, and an anode 268 disposed in the second chamber 264. The first and second chambers 262, 264 are separated by proton permeable, gas impermeable barrier 270, the barrier 270 having surfaces 272, 274 that also define in part the first and second chambers 262, 264.

Unlike the embodiment illustrated in FIG. 7, the embodiment illustrated in FIG. 8 also includes a porous, proton conducting gas diffusion layer 280. The gas diffusion layer 280 is disposed between the cathode 266 and the barrier 270. Using this gas diffusion layer 280, gaseous carbon dioxide may enter the first chamber 212 through the gas diffusion layer 280 and then diffuse into the cathode 266, while gaseous methane produced by the microorganisms may diffuse from the cathode 266 into the layer 280 and then out of the first chamber 212. Proton-conducting gas diffusion layers suitable for use as layer 280 may be produced by coating porous materials with proton-conducting ionomer, by incorporating ionomer directly into the porous matrix, or by chemical derivitization of porous matrix materials with sulfate, phosphate, or other groups that promote proton-conduction, for example.

Figure 14:
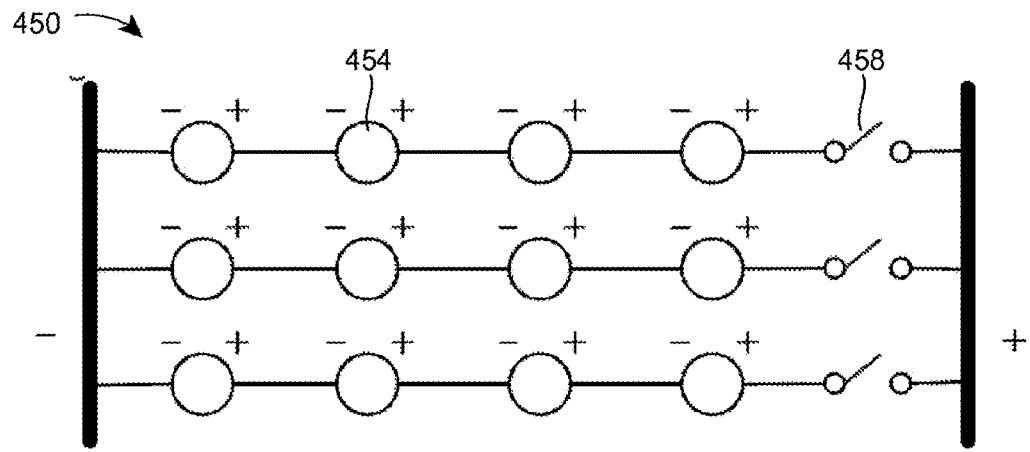
FIG. 14 is a schematic view of a series arrangement of biological reactors according to the present disclosure.

It will thus be recognized that the carbon dioxide and the methane are not carried by a circulating liquid media according to the embodiment of FIG. 8. Instead, the culture and the media are contained in the first chamber 262, while only the gaseous carbon dioxide and the methane circulate between inlet and outlet. Such an embodiment may present certain advantages relative to the reactor 202 of FIG. 7, in that the handling of the methane post-processing or generation may be simplified. Further, the absence of a circulating liquid media in the reactor 202 may simplify the serial connection between multiple reactors, as illustrated in FIG. 14. However, while the circulating media in the embodiment of FIG. 7 provided any water required by the culture, it may be necessary to couple equipment to the reactor to provide water vapor to the culture, in addition to the gaseous carbon dioxide. The electrolyte medium and microorganisms may be retained within the pores of the cathode 266 by surface tension or alternatively by including materials within the electrolyte that increase its viscosity or form a gel.

Figure 9:
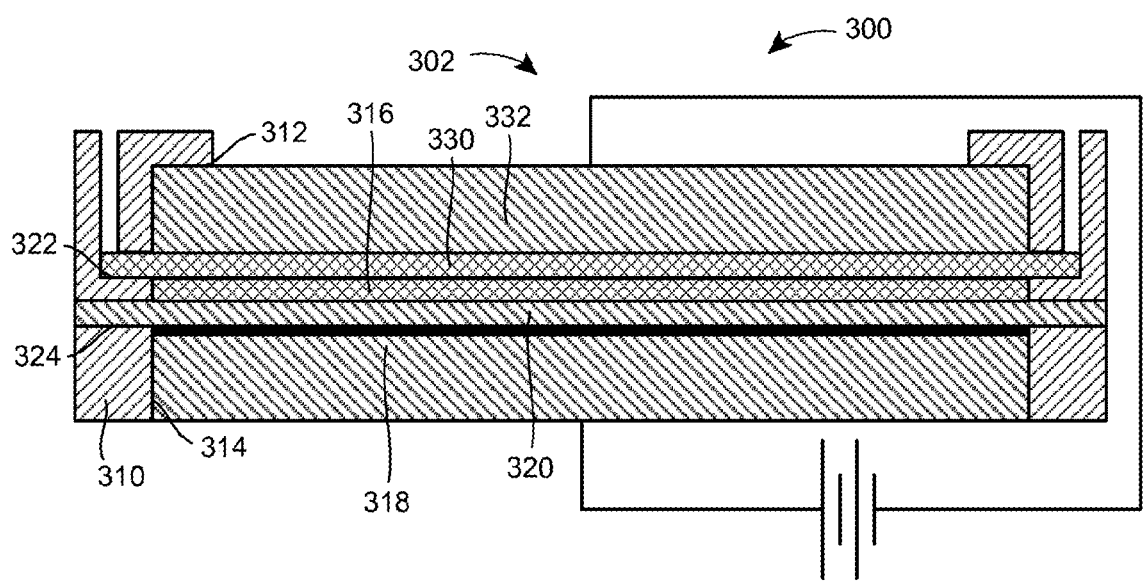
FIG. 9 is a cross-sectional view of a further embodiment of a biological reactor for converting carbon dioxide into methane.

FIG. 9 illustrates a system 300 including a reactor 302 that is a variant of that illustrated in FIG. 8. Similar to the reactors 202 and 252, the reactor 302 includes a housing 310 that defines, in part, first and second chambers 312, 314. The reactor 302 also includes a cathode 316 disposed in the first chamber 312, and an anode 318 disposed in the second chamber 314. The first and second chambers 312, 314 are separated by proton permeable, gas impermeable barrier 320, the barrier 320 having surfaces 322, 324 that also define in part the first and second chambers 312, 314.

Moreover, similar to the embodiment illustrated in FIG. 8, the embodiment illustrated in FIG. 9 also includes a porous, proton conducting gas diffusion layer 330. However, the gas diffusion layer 330 is not disposed between the cathode 316 and the barrier 320, but instead is disposed between the cathode 316 and the current collector 332. In this arrangement, the gas diffusion layer 330 is current-conducting rather than proton-conduction like the gas diffusion layer 280 in reactor 252. Current would pass through the layer 330 into the cathode 316. As in the reactor 252, the carbon dioxide still would enter the first chamber 312 passes through the gas diffusion layer 330 and diffuse into the cathode 316, while methane produced by the microorganisms would diffuse from the cathode 316 through the layer 330.

As a result, the embodiment of FIG. 9 illustrates a reactor wherein the gaseous carbon dioxide enters the cathode from a side or along a path opposite that of the protons. By comparison, the embodiment of FIG. 8 illustrates a reactor wherein the gaseous carbon dioxide and the protons enter the cathode from the same side or along a similar path. The counter-diffusion of the embodiment of FIG. 9 may provide slower production than that of FIG. 8, but may provide acceptable production levels. As to the material used for the barrier 320 according to such an embodiment, it is believed that a porous carbon foam impregnated with Nafion particles may be suitable.

FIGS. 10-13 illustrate a system 400 including a biological reactor 402 that highlights several aspects of the disclosure over and above those illustrated in FIGS. 5-9. In particular, while the general nature of the reactor (with first and second chambers, anode, cathode, barrier, microorganisms, and aqueous electrolyte medium) has much in common with the systems illustrated in FIGS. 5-9, the reactor 402 illustrates new geometries, as well as a reactor in which a plurality of anodes and a plurality of cathodes are present.

Figure 10:
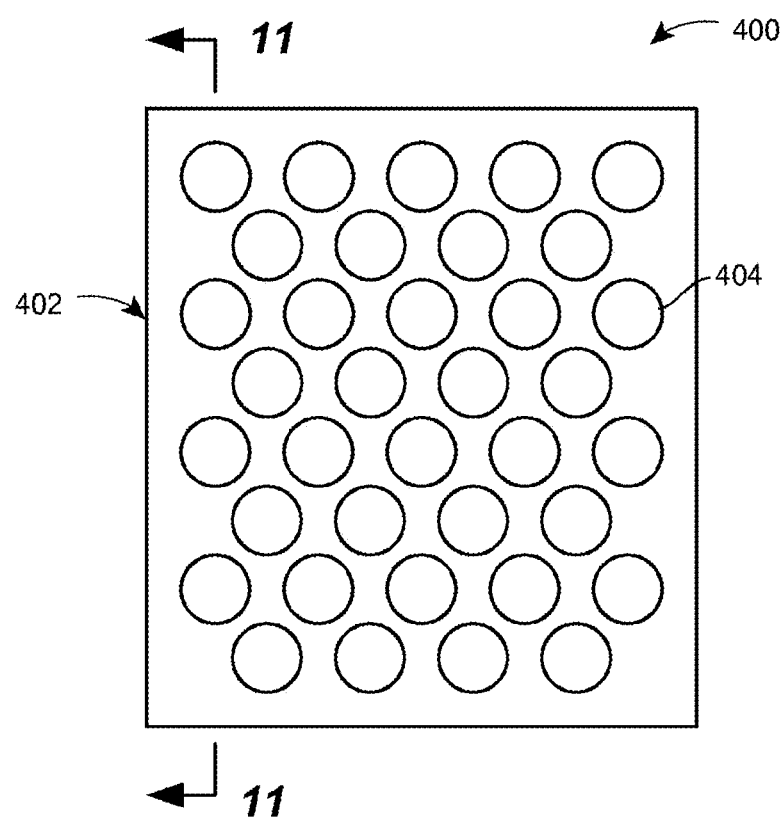
FIG. 10 is a schematic view of an embodiment of a biological reactor with a plurality anodes and cathodes.

In particular, as illustrated in FIG. 10, the reactor 402 includes a number of tubular reactor subunits 404 that may be arranged in a matrix format. It will be recognized that the particular arrangement of the subunits 404 utilizes an offset relative to the arrangement of adjacent rows of subunits 404, so as to increase the number of subunits 404 within a volume. It will also be recognized that adjacent rows of subunits 404 may be aligned with each other instead. It will also be recognized that while four rows of five subunits 404 each and four rows of four subunits 404 each have been illustrated, this should not be taken as limiting the reactor 402 thereby.

FIG. 11 illustrates a plurality of subunits in cross-section, so as to appreciate the similarities and differences with the systems illustrated in FIGS. 5-9 above. While it need not be the case for all embodiments, each of the subunits 404 illustrated in FIG. 11 is identical, such that discussion of any one of the subunits 404 would be inclusive of remarks that may be made relative to the other subunits 404 as well.

As seen in FIG. 11, the reactor 402 includes a housing 410, in which the subunits 404 are disposed. It will be recognized that the housing 410 is sealed against leakage of products and byproducts as explained in greater detail below. Disposed at one end of the housing 410 is a common current collector 412 that is connected to a generally tubular cathode 414 of each of the subunits 404. In a similar fashion, the reactor 402 includes a porous gas diffusion layer/current collector 416 that is connected to a generally tubular anode 418 of each subunit 404. Disposed between the cathode 414 and the anode 418 is a generally tubular proton-permeable, gas impermeable barrier 420, as is discussed in greater detail above. This arrangement is also illustrated in FIG. 12.

According to this embodiment, the carbon dioxide enters the reactor 402 via an inlet 430 and moves along a passage 432. The carbon dioxide then passes along the porous cathode 414, which is impregnated with methanogenic microorganisms and aqueous electrolyte medium. The methane produced in the cathode 414 then is collected in a space 434 that is connected to the outlet 436.

FIG. 13 illustrates a variant to the subunit 404 illustrated relative to the system 400 in FIGS. 10 and 11. Given the similarities between the subunit 404 and its variant, the common structures will be designated with a prime.

As illustrated in FIG. 13, the subunit 404' includes a tubular cathode 414', a tubular anode 418' and a tubular barrier 420'. As in the subunit 404, the tubular cathode 414' is disposed centrally of the subunit 404', with the anode 418' disposed radially outward of the cathode 416' and the barrier 420' disposed therebetween. However, similar to the variants described in FIG. 8, the subunit 404' includes a porous, proton-conducting gas diffusion layer 440. This layer 440 may be in communication with the passage 432 and the space 434 in a reactor 402, instead of the cathode 414'. As such, carbon dioxide would pass from the inlet 430 through the layer 440 to the cathode 414', while methane would pass from the cathode 414' through the layer 440 to the outlet 436. An arrangement similar to FIG. 10, but with an electrically conductive gas diffusion layer arranged as in FIG. 9 between the cathode 414' and the current collector 412' is also possible.

Figure 15:
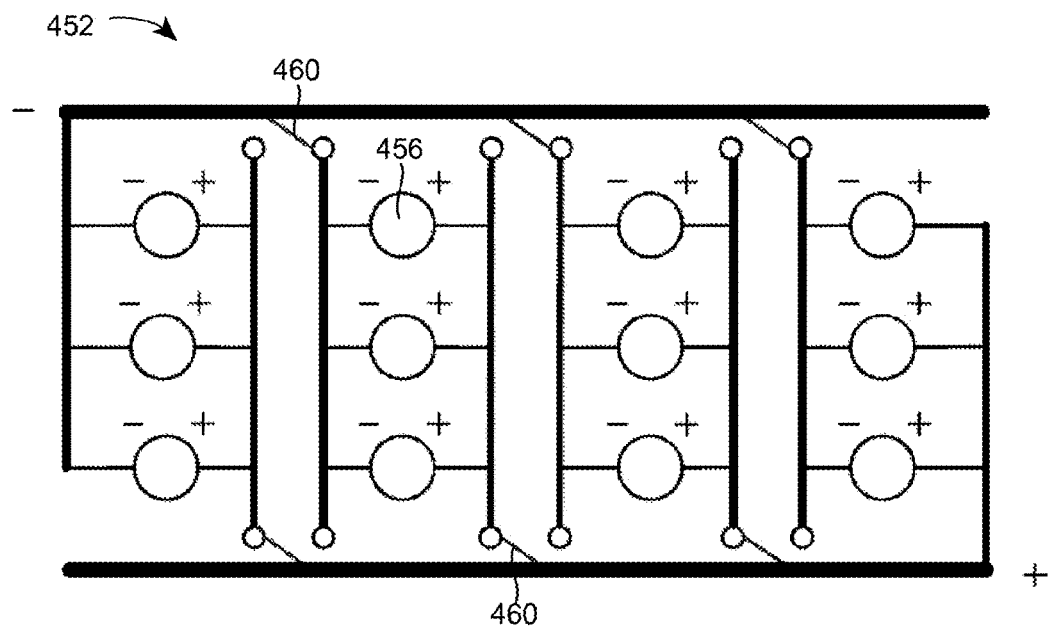
FIG. 15 is a schematic view of a parallel arrangement of biological reactors according to the present disclosure.

FIGS. 14 and 15 illustrate two different power management options that may be used with any of the reactors described above. In this regard, it will be recognized that each of the systems 450, 452 illustrated in FIGS. 14 and 15 may include a plurality of individual reactors 454, 456.

In FIG. 14, the individual reactors 454 are connected in series to match a fixed or constant voltage. The system 450 accommodates a variable current by providing a plurality of switches 458 to permit additional series chains of reactors 454 to be switched into the circuit to match variable current. In FIG. 15, the individual reactors 456 are connected in parallel to match a fixed or constant current. The system 452 accommodates a variable voltage by providing pairs of switches 460 to permit additional parallel planes of reactors 456 to be switched into the circuit to match variable voltage. It will be recognized that it may also be possible to address variable current and variable voltage applications with addressable switching so as to build dynamic parallel reactor planes and to adjust the lengths of series chains as needed.

EXEMPLARY EMBODIMENTS

The following enumerated paragraphs describe exemplary embodiments:

1. An isolated *Methanothermobacter* microorganism that exhibits a methane production efficiency that is at least or about 25 $CO_2$ molecules converted to methane per $CO_2$ molecule converted to cellular material.

2. The isolated *Methanothermobacter* microorganism of enumerated paragraph 1, wherein the microorganism expresses a 16S rRNA that has at least 90% sequence identity to the full length of the sequence of 16S rRNA of *Methanothermobacter thermautotrophicus* Delta H (SEQ ID NO: 1).

3. The isolated *Methanothermobacter* microorganism of enumerated paragraph 2, wherein the microorganism expresses a 16S rRNA that has at least 95% sequence identity to the full length of the sequence of 16S rRNA of *Methanothermobacter thermautotrophicus* Delta H (SEQ ID NO: 1).

4. The isolated *Methanothermobacter* microorganism of enumerated paragraph 3, wherein the microorganism expresses a 16S rRNA that has at least 98% sequence identity to the full length of the sequence of 16S rRNA of *Methanothermobacter thermautotrophicus* Delta H (SEQ ID NO: 1).

5. The isolated *Methanothermobacter* microorganism of any one of enumerated paragraphs 1 to 4 that exhibits a methane production efficiency that is at least or about 40 $CO_2$ molecules converted to methane per $CO_2$ molecule converted to cellular material.

6. The isolated *Methanothermobacter* microorganism of enumerated paragraph 5 that exhibits a methane production efficiency that is at least or about 50 $CO_2$ molecules converted to methane per $CO_2$ molecule converted to cellular material.

7. The isolated *Methanothermobacter* microorganism of enumerated paragraph 6 that exhibits a methane production efficiency that is at least or about 60 $CO_2$ molecules converted to methane per $CO_2$ molecule converted to cellular material.

8. The isolated *Methanothermobacter* microorganism of any one of enumerated paragraphs 1 to 7, wherein the methane production efficiency from $CO_2$ is maintained for at least 30 consecutive days (i.e., "maintained for" means that the microorganism exhibits this phenotype at least one time each day for the at least 30 consecutive days).

9. The isolated *Methanothermobacter* microorganism of any one of enumerated paragraphs 1 to 8, wherein the microorganism exhibits the methane production efficiency when no more than 25 molecules of hydrogen are supplied to the microorganism for every 6 molecules of methane produced, or no more than 200 molecules of hydrogen are supplied for every 49 molecules of methane produced.

10. The isolated *Methanothermobacter* microorganism of any one of enumerated paragraphs 1 to 9 that produces at least or about 96 molecules of methane per 100 molecules of carbon dioxide supplied to the microorganism.

11. The isolated *Methanothermobacter* microorganism of any one of enumerated paragraphs 1 to 10 that produces at least or about 17 grams of methane per gram of cellular material.

12. An isolated *Methanothermobacter* microorganism that produces at least or about 96 molecules of methane per 100 molecules of carbon dioxide supplied to the microorganism.

13. The isolated *Methanothermobacter* microorganism of enumerated paragraph 12, wherein the microorganism expresses a 16S rRNA that has at least 90% sequence identity to the full length of the sequence of 16S rRNA of *Methanothermobacter thermautotrophicus* Delta H (SEQ ID NO: 1).

14. The isolated *Methanothermobacter* microorganism of enumerated paragraph 13, wherein the microorganism expresses a 16S rRNA that has at least 95% sequence identity to the full length of the sequence of 16S rRNA of *Methanothermobacter thermautotrophicus* Delta H (SEQ ID NO: 1).

15. The isolated *Methanothermobacter* microorganism of enumerated paragraph 14, wherein the microorganism expresses a 16S rRNA that has at least 98% sequence identity to the full length of the sequence of 16S rRNA of *Methanothermobacter thermautotrophicus* Delta H (SEQ ID NO: 1).

16. The isolated *Methanothermobacter* microorganism of any one of enumerated paragraphs 12 to 15 that produces at least or about 97 molecules of methane per 100 molecules of carbon dioxide supplied to the microorganism.

17. The isolated *Methanothermobacter* microorganism of enumerated paragraph 16 that produces at least or about 98 molecules of methane per 100 molecules of carbon dioxide supplied to the microorganism.

18. The isolated *Methanothermobacter* microorganism of any one of enumerated paragraphs 12 to 17, wherein the microorganism produces at least or about 96 molecules of methane per 100 molecules of $CO_2$ supplied to the microorganism, when no more than 25 molecules of hydrogen are supplied to the microorganism for every 6 molecules of methane produced, or no more than 200 molecules of hydrogen are supplied for every 49 molecules of methane produced.

19. The isolated *Methanothermobacter* microorganism of any one of enumerated paragraphs 12 to 18 that exhibits a methane production efficiency that is at least or about 25 $CO_2$ molecules converted to methane per $CO_2$ molecule converted to cellular material.

20. The isolated *Methanothermobacter* microorganism of any one of enumerated paragraphs 12 to 19 that produces at least or about 17 grams of methane per gram from $CO_2$ of cellular material produced from $CO_2$.

21. An isolated *Methanothermobacter* microorganism that produces at least or about 17 grams of methane from $CO_2$ per gram of cellular material produced from $CO_2$.

22. The isolated *Methanothermobacter* microorganism of enumerated paragraph 21, wherein the microorganism expresses a 16S rRNA that has at least 90% sequence identity to the full length of the sequence of 16S rRNA of *Methanothermobacter thermautotrophicus* Delta H (SEQ ID NO: 1).

23. The isolated *Methanothermobacter* microorganism of enumerated paragraph 22, wherein the microorganism expresses a 16S rRNA that has at least 95% sequence identity to the full length of the sequence of 16S rRNA of *Methanothermobacter thermautotrophicus* Delta H (SEQ ID NO: 1).

24. The isolated *Methanothermobacter* microorganism of enumerated paragraph 23, wherein the microorganism expresses a 16S rRNA that has at least 98% sequence identity to the full length of the sequence of 16S rRNA of *Methanothermobacter thermautotrophicus* Delta H (SEQ ID NO: 1).

25. The isolated *Methanothermobacter* microorganism of any one of enumerated paragraphs 21 to 24 that produces at least or about 20 grams of methane from $CO_2$ per gram of cellular material produced from $CO_2$.

26. The isolated *Methanothermobacter* microorganism of enumerated paragraph 25 that produces at least or about 30 grams of methane from $CO_2$ per gram of cellular material produced from $CO_2$.

27. The isolated *Methanothermobacter* microorganism of enumerated paragraph 26 that produces at least or about 40 grams of methane from $CO_2$ per gram of cellular material produced from $CO_2$.

28. The isolated *Methanothermobacter* microorganism of any one of enumerated paragraphs 21 to 27, wherein the microorganism produces at least or about 17 grams of methane from $CO_2$ per gram of cellular material from $CO_2$ produced when no more than 25 molecules of hydrogen are supplied to the microorganism for every 6 molecules of methane produced, or no more than 200 molecules of hydrogen are supplied for every 49 molecules of methane produced.

29. The isolated *Methanothermobacter* microorganism of any one of enumerated paragraphs 21 to 28 that exhibits a methane production efficiency that is at least or about 25 $CO_2$ molecules converted to methane per $CO_2$ molecule converted to cellular material.

30. The isolated *Methanothermobacter* microorganism of any one of enumerated paragraphs 21 to 29 that produces at least or about 96 molecules of methane per 100 molecules of carbon dioxide supplied to the microorganism.

31. The isolated *Methanothermobacter* microorganism of any one of the preceding enumerated paragraphs that exhibits a doubling time of at least or about 72 hours in a stationary phase.

32. The isolated *Methanothermobacter* microorganism of enumerated paragraph 31 that exhibits a doubling time of at least or about 80 hours in a stationary phase.

33. The isolated *Methanothermobacter* microorganism of enumerated paragraph 32 that exhibits a doubling time of at least or about 90 hours in a stationary phase.

34. The isolated *Methanothermobacter* microorganism of enumerated paragraph 33 that exhibits a doubling time of at least or about 100 hours in a stationary phase.

35. The isolated *Methanothermobacter* microorganism of enumerated paragraph 34 that exhibits a doubling time of at least or about 200 hours in the stationary phase.

36. The *Methanothermobacter* microorganism of enumerated paragraph 35 that exhibits a doubling time of at least or about 1 month in a stationary phase.

37. The isolated *Methanothermobacter* microorganism of any one of enumerated paragraphs 31 to 36, wherein the doubling time is maintained for at least 7 consecutive days.

38. The isolated *Methanothermobacter* microorganism of enumerated paragraph 37, wherein the doubling time is maintained for at least 30 consecutive days.

39. The isolated *Methanothermobacter* microorganism of any one of enumerated paragraphs 31 to 38 that exhibits a doubling time of at least or about 72 hours in a stationary phase when provided with $CO_2$ gas at a rate of at least or about 34 VVD.

40. The isolated *Methanothermobacter* microorganism of any one of enumerated paragraphs 31 to 39 that exhibits a doubling time of at least or about 72 hours in a stationary phase when provided with $CO_2$ gas at a rate of at least or about 34 VVD and with reducing power sufficient to reduce at least 90% of the $CO_2$.

41. The isolated *Methanothermobacter* microorganism of enumerated paragraph 46, wherein the reducing power is $H_2$ gas supplied at a rate of at least 122 VVD.

42. The isolated *Methanothermobacter* microorganism of enumerated paragraph 46, wherein the reducing power is electrical current.

43. The isolated *Methanothermobacter* microorganism of any one of enumerated paragraphs 1 to 41 that returns to at least 80% of the methane productivity level in the operating state within 20 minutes of exposure to at least or about 3 minutes of either oxygen or carbon monoxide.

44. The isolated *Methanothermobacter* microorganism of enumerated paragraph 43, wherein the microorganism returns to at least 80% of the methane productivity level in the operating state within 10 minutes of exposure to at least or about 3 minutes of oxygen.

45. The isolated *Methanothermobacter* microorganism of any one of enumerated paragraphs 1 to 44 that exhibits a cell culture density of at least or about 6 mg dry mass of cells/ml culture in a stationary phase.

46. The isolated *Methanothermobacter* microorganism of enumerated paragraph 45 that exhibits a cell culture density of at least or about 6 mg dry mass of cells/ml culture in a stationary phase for at least or about 15 consecutive days.

47. The isolated *Methanothermobacter* microorganism of any one of enumerated paragraphs 1 to 46 that returns to at least 80% of the methane productivity in the operating state within 20 minutes of re-supplying $H_2$ gas or electricity, after being in a dormant state for at least 2 hours as induced by interrupting or ceasing hydrogen supply or electricity.

48. The isolated *Methanothermobacter* microorganism of any one of enumerated paragraphs 1 to 47, wherein the microorganism is autotrophic.

49. The isolated *Methanothermobacter* microorganism of enumerated paragraph 48 that is thermophilic or hyperthermophilic.

50. The isolated *Methanothermobacter* microorganism of any one of enumerated paragraphs 1 to 49 that is a microorganism of *Methanothermobacter thermautotrophicus* strain UC 120910, deposited on Dec. 21, 2010, with the American Type Culture Collection (ATCC) under ATCC® Patent Deposit Designation No. PTA-11561.

51. An isolated *Methanothermobacter* microorganism that exhibits a doubling time of at least or about 72 hours in a stationary phase.

52. The isolated *Methanothermobacter* microorganism of enumerated paragraph 51, wherein the microorganism expresses a 16S rRNA that has at least 90% sequence identity to the full length of the sequence of 16S rRNA of *Methanothermobacter thermautotrophicus* Delta H (SEQ ID NO: 1).

53. The isolated *Methanothermobacter* microorganism of enumerated paragraph 52, wherein the microorganism expresses a 16S rRNA that has at least 95% sequence identity to the full length of the sequence of 16S rRNA of *Methanothermobacter thermautotrophicus* Delta H (SEQ ID NO: 1).

54. The isolated *Methanothermobacter* microorganism of enumerated paragraph 53, wherein the microorganism expresses a 16S rRNA that has at least 98% sequence identity to the full length of the sequence of 16S rRNA of *Methanothermobacter thermautotrophicus* Delta H (SEQ ID NO: 1).

55. The isolated *Methanothermobacter* microorganism of any one of enumerated paragraphs 51 to 54 that exhibits a doubling time of at least or about 80 hours in a stationary phase.

56. The isolated *Methanothermobacter* microorganism of enumerated paragraph 55 that exhibits a doubling time of at least or about 90 hours in a stationary phase.

57. The isolated *Methanothermobacter* microorganism of enumerated paragraph 56 that exhibits a doubling time of at least or about 100 hours in a stationary phase.

58. The isolated *Methanothermobacter* microorganism of enumerated paragraph 57 that exhibits a doubling time of at least or about 200 hours in the stationary phase.

59. The *Methanothermobacter* microorganism of enumerated paragraph 58 that exhibits a doubling time of at least or about 1 month in a stationary phase.

60. The isolated *Methanothermobacter* microorganism of any one of enumerated paragraphs 51 to 59, wherein the doubling time is maintained for at least 7 consecutive days.

61. The isolated *Methanothermobacter* microorganism of 60, wherein the doubling time is maintained for at least 30 consecutive days.

62. The isolated *Methanothermobacter* microorganism of any one of enumerated paragraphs 51 to 61 that exhibits a doubling time of at least or about 72 hours in a stationary phase when provided with $CO_2$ gas at a rate of at least or about 34 VVD.

63. The isolated *Methanothermobacter* microorganism of any one of enumerated paragraphs 51 to 62 that exhibits a doubling time of at least or about 72 hours in a stationary phase when provided with $CO_2$ gas at a rate of at least or about 34 VVD and with reducing power sufficient to reduce at least 90% of the $CO_2$.

64. The isolated *Methanothermobacter* microorganism of enumerated paragraph 63, wherein the reducing power is $H_2$ gas supplied at a rate of at least 122 VVD.

65. The isolated *Methanothermobacter* microorganism of enumerated paragraph 63, wherein the reducing power is electrical current.

66. The isolated *Methanothermobacter* microorganism of any one of enumerated paragraphs 51 to 65 that exhibits a methane production efficiency that is at least or about 25 $CO_2$ molecules converted to methane per $CO_2$ molecule converted to cellular material.

67. The isolated *Methanothermobacter* microorganism of any one of enumerated paragraphs 51 to 66 that produces at least or about 96 molecules of methane per 100 molecules of carbon dioxide supplied to the microorganism.

68. The isolated *Methanothermobacter* microorganism of any one of enumerated paragraphs 51 to 67 that produces at least or about 17 grams of methane from $CO_2$, per gram of cellular material produced from $CO_2$.

69. The isolated *Methanothermobacter* microorganism of any one of enumerated paragraphs 51 to 68 that returns to at least 80% of the methane productivity level in the operating state within 20 minutes of exposure to at least or about 3 minutes of either oxygen or carbon monoxide.

70. The isolated *Methanothermobacter* microorganism of enumerated paragraph 69, wherein the microorganism returns to at least 80% of the methane productivity level in the operating state within 10 minutes of exposure to at least or about 3 minutes of oxygen.

71. The isolated *Methanothermobacter* microorganism of any one of enumerated paragraphs 51 to 70 that exhibits a cell culture density of at least or about 6 mg dry mass of cells/ml culture in a stationary phase.

72. The isolated *Methanothermobacter* microorganism of enumerated paragraph 71 that exhibits a cell culture density of at least or about 6 mg dry mass of cell s/ml culture in a stationary phase for at least or about 15 consecutive days.

73. The isolated *Methanothermobacter* microorganism of any one of enumerated paragraphs 51 to 72 that returns to at least 80% of the methane productivity in the operating state within 20 minutes of re-supplying $H_2$ gas or electricity, after being in a dormant state for at least 2 hours as induced by interrupting or ceasing hydrogen supply or electricity.

74. The isolated *Methanothermobacter* microorganism of any one of enumerated paragraphs 51 to 73, wherein the microorganism is autotrophic.

75. The isolated *Methanothermobacter* microorganism of enumerated paragraph 74 that is thermophilic or hyperthermophilic.

76. The isolated *Methanothermobacter* microorganism of any one of enumerated paragraphs 51 to 75 that is a microorganism of *Methanothermobacter thermautotrophicus* strain UC 120910, deposited on Dec. 21, 2010, with the American Type Culture Collection (ATCC®) under ATCC® Patent Deposit Designation No. PTA-11561.

77. An isolated *Methanothermobacter* microorganism that:
   a. exhibits a methane production efficiency that is at least or about 25 $CO_2$ molecules converted to methane per $CO_2$ molecule converted to cellular material; or
   b. survives in a stationary phase with a doubling time of at least or about 72 hours; or
   c. exhibits a cell culture density of at least or about 6 mg dry mass of cells/ml culture in a stationary phase; or
   d. returns to at least 80% of the methane productivity level in the operating state within 20 minutes, after an exposure of at least or about 3 minutes to oxygen or carbon monoxide.

78. The isolated *Methanothermobacter* microorganism of enumerated paragraph 77, wherein the microorganism expresses a 16S rRNA that has at least 90% sequence identity to the full length of the sequence of 16S rRNA of *Methanothermobacter thermautotrophicus* Delta H (SEQ ID NO: 1).

79. The isolated *Methanothermobacter* microorganism of enumerated paragraph 78, wherein the microorganism expresses a 16S rRNA that has at least 95% sequence identity to the full length of the sequence of 16S rRNA of *Methanothermobacter thermautotrophicus* Delta H (SEQ ID NO: 1).

80. The isolated *Methanothermobacter* microorganism of enumerated paragraph 79, wherein the microorganism expresses a 16S rRNA that has at least 98% sequence identity to the full length of the sequence of 16S rRNA of *Methanothermobacter thermautotrophicus* Delta H (SEQ ID NO: 1).

81. The isolated *Methanothermobacter* microorganism of any one of enumerated paragraphs 77 to 80 that (i) exhibits a methane production efficiency that is at least or about 25 $CO_2$ molecules converted to methane per $CO_2$ molecule converted to cellular material, optionally while exhibiting a doubling time of at least or about 72 hours, optionally, wherein the methane production efficiency from $CO_2$ is maintained for at least 30 days, or (ii) survives in a stationary phase with a doubling time of at least or about 72 hours, optionally for at least 30 days.

82. The isolated *Methanothermobacter* microorganism of any one of enumerated paragraphs 77 to 81 that (i) exhibits a cell culture density within a range of about 6 to about 8 mg dry mass of cells/ml culture in a stationary phase, or (ii) returns to at least 80% of the methane productivity level in the operating state within 20 minutes, after an exposure of at least or about 3 minutes to either oxygen or carbon monoxide.

83. The isolated *Methanothermobacter* microorganism of any one of enumerated paragraphs 77 to 82 that is thermophilic or hyperthermophilic, or (ii) returns to at least 80% of the methane productivity in the operating state within 20 minutes of re-supplying $H_2$ gas or electricity, after being in a dormant state for at least 2 hours as induced by interrupting or ceasing hydrogen supply or electricity.

84. The isolated *Methanothermobacter* microorganism of any one of enumerated paragraphs 77 to 83 that is a microorganism of *Methanothermobacter thermautotrophicus* strain UC 120910, deposited on Dec. 21, 2010, with the American Type Culture Collection (ATCC®) under ATCC® Patent Deposit Designation No. PTA-11561.

85. An isolated *Methanothermobacter* microorganism that is
(a) a microorganism of *Methanothermobacter thermautotrophicus* strain UC 120910, deposited on Dec. 21, 2010, with the American Type Culture Collection (ATCC®) under ATCC® Patent Deposit Designation No. PTA-11561,
(b) a variant of (a), or
(c) a progeny of (a),
wherein the variant or progeny retains the $CO_2$ conversion phenotypic characteristics of (a).

86. The isolated *Methanothermobacter* microorganism of enumerated paragraph 85, wherein the variant or progeny expresses a 16S rRNA that has at least 90% sequence identity to the full length of the sequence of 16S rRNA of *Methanothermobacter thermautotrophicus* Delta H (SEQ ID NO: 1).

87. The isolated *Methanothermobacter* microorganism of enumerated paragraph 86, wherein the variant or progeny expresses a 16S rRNA that has at least 95% sequence identity to the full length of the sequence of 16S rRNA of *Methanothermobacter thermautotrophicus* Delta H (SEQ ID NO: 1).

88. The isolated *Methanothermobacter* microorganism of enumerated paragraph 87, wherein the variant or progeny expresses a 16S rRNA that has at least 98% sequence identity to the full length of the sequence of 16S rRNA of *Methanothermobacter thermautotrophicus* Delta H (SEQ ID NO: 1).

89. The isolated *Methanothermobacter* microorganism of any one of enumerated paragraphs 77 to 88, wherein the variant or progeny exhibits a methane production efficiency that is at least or about 25 $CO_2$ molecules converted to methane per $CO_2$ molecule converted to cellular material.

90. The isolated *Methanothermobacter* microorganism of enumerated paragraph 89 that exhibits a methane production efficiency that is at least or about 40 $CO_2$ molecules converted to methane per $CO_2$ molecule converted to cellular material.

91. The isolated *Methanothermobacter* microorganism of enumerated paragraph 90 that exhibits a methane production efficiency that is at least or about 50 $CO_2$ molecules converted to methane per $CO_2$ molecule converted to cellular material.

92. The isolated *Methanothermobacter* microorganism of enumerated paragraph 91 that exhibits a methane production efficiency that is at least or about 60 $CO_2$ molecules converted to methane per $CO_2$ molecule converted to cellular material.

93. The isolated *Methanothermobacter* microorganism of any one of enumerated paragraphs 89 to 92, wherein the methane production efficiency from $CO_2$ is maintained for at least 30 consecutive days.

94. The isolated *Methanothermobacter* microorganism of any one of enumerated paragraphs 89 to 93, wherein the microorganism exhibits the methane production efficiency when no more than 25 molecules of hydrogen are supplied to the microorganism for every 6 molecules of methane produced, or no more than 200 molecules of hydrogen are supplied for every 49 molecules of methane produced.

95. The isolated *Methanothermobacter* microorganism of any one of enumerated paragraphs 77 to 94 that produces at least or about 96 molecules of methane per 100 molecules of carbon dioxide supplied to the microorganism.

96. The isolated *Methanothermobacter* microorganism of enumerated paragraph 95 that produces at least or about 97 molecules of methane per 100 molecules of carbon dioxide supplied to the microorganism.

97. The isolated *Methanothermobacter* microorganism of enumerated paragraph 96 that produces at least or about 98 molecules of methane per 100 molecules of carbon dioxide supplied to the microorganism.

98. The isolated *Methanothermobacter* microorganism of any one of enumerated paragraphs 95 to 97, wherein the microorganism produces at least or about 96 molecules of methane per 100 molecules of $CO_2$ supplied to the microorganism, when no more than 25 molecules of hydrogen are supplied to the microorganism for every 6 molecules of methane produced, or no more than 200 molecules of hydrogen are supplied for every 49 molecules of methane produced.

99. The isolated *Methanothermobacter* microorganism of any one of enumerated paragraphs 77 to 98 that produces at least or about 17 grams of methane from $CO_2$ per gram of cellular material produced from $CO_2$.

100. The isolated *Methanothermobacter* microorganism of enumerated paragraph 99 that produces at least or about 20 grams of methane from $CO_2$ per gram of cellular material produced from $CO_2$.

101. The isolated *Methanothermobacter* microorganism of enumerated paragraph 100 that produces at least or about 30 grams of methane from CO) per gram of cellular material produced from $CO_2$.

102. The isolated *Methanothermobacter* microorganism of enumerated paragraph 101 that produces at least or about 40 grams of methane from $CO_2$ per gram of cellular material produced from $CO_2$.

103. The isolated *Methanothermobacter* microorganism of any one of enumerated paragraphs 99 to 102, wherein the microorganism produces at least or about 17 grams of methane from $CO_2$ per gram of cellular material produced, when no more than 25 molecules of hydrogen are supplied to the microorganism for every 6 molecules of methane produced, or no more than 200 molecules of hydrogen are supplied for every 49 molecules of methane produced.

104. The isolated *Methanothermobacter* microorganism of any one of enumerated paragraphs 77 to 103 that exhibits a doubling time of at least or about 72 hours in a stationary phase.

105. The isolated *Methanothermobacter* microorganism of enumerated paragraph 104 that exhibits a doubling time of at least or about 80 hours in a stationary phase.

106. The isolated *Methanothermobacter* microorganism of enumerated paragraph 105 that exhibits a doubling time of at least or about 90 hours in a stationary phase.

107. The isolated *Methanothermobacter* microorganism of enumerated paragraph 106 that exhibits a doubling time of at least or about 100 hours in a stationary phase.

108. The isolated *Methanothermobacter* microorganism of enumerated paragraph 107 that exhibits a doubling time of at least or about 200 hours in the stationary phase.

109. The *Methanothermobacter* microorganism of enumerated paragraph 108 that exhibits a doubling time of at least or about 1 month in a stationary phase.

110. The isolated *Methanothermobacter* microorganism of any one of enumerated paragraphs 104 to 109, wherein the doubling time is maintained for at least 7 consecutive days.

111. The isolated *Methanothermobacter* microorganism of enumerated paragraph 110, wherein the doubling time is maintained for at least 30 consecutive days.

112. The isolated *Methanothermobacter* microorganism of any one of enumerated paragraphs 104 to 111 that exhibits a doubling time of at least or about 72 hours in a stationary phase when provided with $CO_2$ gas at a rate of at least or about 34 VVD.

113. The isolated *Methanothermobacter* microorganism of any one of enumerated paragraphs 104 to 112 that exhibits a doubling time of at least or about 72 hours in a stationary phase when provided with $CO_2$ gas at a rate of at least or about 34 VVD and with reducing power sufficient to reduce at least 90% of the $CO_2$.

114. The isolated *Methanothermobacter* microorganism of enumerated paragraph 113, wherein the reducing power is $H_2$ gas supplied at a rate of at least 122 VVD.

115. The isolated *Methanothermobacter* microorganism of enumerated paragraph 113, wherein the reducing power is electrical current.

116. The isolated *Methanothermobacter* microorganism of any one of enumerated paragraphs 77 to 115 that returns to at least 80% of the methane productivity level in the operating state within 20 minutes of exposure to at least or about 3 minutes of either oxygen or carbon monoxide.

117. The isolated *Methanothermobacter* microorganism of enumerated paragraph 116, wherein the microorganism returns to at least 80% of the methane productivity level in the operating state within 10 minutes of exposure to at least or about 3 minutes of oxygen.

118. The isolated *Methanothermobacter* microorganism of any one of enumerated paragraphs 77 to 117 that exhibits a cell culture density of at least or about 6 mg dry mass of cells/ml culture in a stationary phase.

119. The isolated *Methanothermobacter* microorganism of enumerated paragraph 118 that exhibits a cell culture density of at least or about 6 mg dry mass of cells/ml culture in a stationary phase for at least or about 15 consecutive days.

120. The isolated *Methanothermobacter* microorganism of any one of enumerated paragraphs 77 to 119 that returns to at least 80% of the methane productivity in the operating state within 20 minutes of re-supplying $H_2$ gas or electricity, after being in a dormant state for at least 2 hours as induced by interrupting or ceasing hydrogen supply or electricity.

121. The isolated *Methanothermobacter* microorganism of any one of enumerated paragraphs 77 to 120 wherein the microorganism is autotrophic.

122. The isolated *Methanothermobacter* microorganism of enumerated paragraph 121 that is thermophilic or hyperthermophilic.

123. The isolated *Methanothermobacter* microorganism of any one of enumerated paragraphs 85 to 122 that is a microorganism of *Methanothermobacter thermautotrophicus* strain UC 120910, deposited on Dec. 21, 2010, with the American Type Culture Collection (ATCC®) under ATCC® Patent Deposit Designation No. PTA-11561.

124. An isolated *Methanothermobacter* microorganism that is a progeny of *Methanothermobacter thermautotrophicus* strain UC 120910, deposited on Dec. 21, 2010, with the American Type Culture Collection (ATCC®) under ATCC® Patent Deposit Designation No. PTA-11561, wherein the progeny retains the $CO_2$ conversion phenotypic characteristics of said strain.

125. A substantially pure culture or monoculture comprising the microorganism of any one of enumerated paragraphs 1 to 124.

126. A system for converting electric power into methane, comprising a biological reactor having at least a cathode, an anode, a microorganism of any one of enumerated paragraphs 1 to 124, water, and carbon dioxide.

127. The system of enumerated paragraph 126, wherein the biological reactor comprises at least a first chamber comprising said cathode, said microorganism, and water, and a second chamber containing at least an anode, wherein the system further comprises a source of electricity coupled to the anode and the cathode, a supply of carbon dioxide coupled to the first chamber, and an outlet to receive methane from the first chamber.

128. A method of converting electricity into methane, comprising supplying electricity and carbon dioxide to the system of enumerated paragraph 126 or 127, the biological reactor having an operating state wherein the microorganism is maintained at a temperature greater than or about 60° C., and collecting methane from the first chamber.

129. A porous cathode comprising the isolated *Methanothermobacter* microorganism of any one of enumerated paragraphs 1 to 124.

130. A kit comprising an isolated *Methanothermobacter* microorganism of any one of enumerated paragraphs 1 to 124, a substantially pure culture or monoculture of enumerated paragraph 125, a system of enumerated paragraph 126 or 127, a porous cathode of enumerated paragraph 129, or a combination thereof, and instructions for care or for use.

131. The kit of enumerated paragraph 130, where the microorganism or culture or monoculture is cryopreserved.

132. The kit of enumerated paragraph 130 or 131, comprising an amount of the microorganism or culture or monoculture that is ready to use in a system for methane production.

133. A cell culture inoculum comprising at least or about 1.6 kg dry weight of the isolated *Methanothermobacter* microorganisms of any one of enumerated paragraphs 1 to 124.

134. A large-scale culture which is ready for use in methane production comprising at least or about 1000 L of a culture at a density of at least or about 6 g dry weight cell/L culture of the isolated *Methanothermobacter* microorganism of any one of enumerated paragraphs 1 to 124.

The following examples are provided for illustration, and by way of limitation.

EXAMPLES

Example 1

This example describes an exemplary method of maintaining a *Methanothermobacter* microorganism of the disclosure and an exemplary method of cryopreserving the microorganism.

The microorganisms of *Methanothermobacter thermautotrophicus* strain UC 120910 are maintained in Medium 1, disclosed herein, at 60° C. under anaerobic conditions comprising 80% hydrogen, 20% carbon dioxide in a New Brunswick BioFlo 110 Fermenter with a 1.3 L nominal total volume glass vessel. The culture vessel contains four full-height baffles, extending 6 mm from the wall. Double bladed, 6-blade Rushton Impellers (52 mm diameter) are placed inside the culture vessel and are maintained at a typical stirring speed of about 1000 RPM. The hydrogen sparger is a perforated tube (10 perforations of about 0.5 mm in diameter) placed in a circle just below the bottom impeller. The primary bubbles released from the sparger are relatively large and are substantially broken up by the action of the impeller.

The culture vessel is maintained at a constant 60° C. and at a liquid volume within a range of about 0.3 L to about 1 L (e.g., 0.7 L). Because water is a by-product of methanogensis, liquid is constantly being removed from the reactor. The microorganisms are maintained in the culture vessel within a measured biomass range of about 0.005 to about 0.011 g dry solid/mL water (0.5-1% dry mass per unit volume).

Alternatively, the microorganisms of *Methanothermobacter thermautotrophicus* strain UC 120910 are maintained in culture tubes or bottles comprising either Medium 1 or ATCC medium 2133:OSU967 at 60° C. under anaerobic conditions comprising a gas phase of 80% hydrogen, 20% carbon dioxide. As a further alternative, the microorganisms of *Methanothermobacter thermautotrophicus* strain UC 120910 are maintained on the surface of solidified Medium 1 or ATCC medium 2133:OSU967 at 60° C. under anaerobic conditions comprising a gas phase of 80% hydrogen, 20% carbon dioxide.

The microorganisms are cryopreserved by suspending microorganisms in a liquid growth medium containing 10% glycerol. The microorganism suspension is then placed into a −80° C. freezer. The cryopreserved organisms are returned to growth by inoculation into fresh liquid medium or onto solidified medium and incubation under anaerobic conditions at 60° C. as described above.

Example 2

This example describes two exemplary methods of using the microorganisms of the disclosure for producing methane.

Hydrogenotrophic Methanogensis

Microorganisms of *Methanothermobacter thermautotrophicus* strain UC 120910 are cultured in a New Brunswick BioFlo 110 Fermenter in Medium 1 as essentially described in Example 1. Methane and hydrogen ($H_2$) outflow rates from the batch culture are calculated as a function of the hydrogen and methane mass spectrometry signals (corrected for ionization probability) and the hydrogen inflow rate. The calculation assumes that all hydrogen that enters the batch culture is either converted to methane at a ratio of $4H_2:1CH_4$ or exits the culture as unreacted hydrogen. Under steady state conditions with doubling times of 50 hours or greater, the small proportion of hydrogen that is consumed in the growth of the organisms is neglected in the calculation.

Calculation of VVD methane productivity. The volumetric flow of hydrogen entering the culture is controlled by a gas mass-flow controller and provides a primary reference for determination of the rate of methane production. The ratio of masses detected by the mass spectrometer at mass 15 to that at mass 2 is determined for a range of methane to hydrogen ratios in standard gas mixtures generated by gas mass-flow controllers to obtain correction constants. The ratio of mass 15 to mass 2 in experimental gas streams is then multiplied by the correction constant to obtain the ratio of methane to hydrogen gas in the fermenter/reactor exit gas stream. By assuming that hydrogen in the input gas stream is converted to methane at a 4:1 molar ratio, the absolute rate of methane and hydrogen flow out of the reactor is calculated from the input hydrogen flow rate and the observed gas ratio in the exit flow. Methane productivity in units of VVD are calculated as the volume of methane in the exit flow per day divided by the liquid volume of the fermenter/reactor.

In an exemplary method, microorganisms of *Methanothermobacter thermautotrophicus* strain UC 120910 are cultured in a New Brunswick BioFlo 110 Fermenter in Medium 1 as essentially described in Example 1. Specifically, the Fermenter is maintained with impellers stirring at 1000 RPM and a culture volume of 400 mL and at a temperature of 60° C. Hydrogen gas is delivered to the system at a gas flow rate of 10 L/min $H_2$ and carbon dioxide is delivered at a gas flow rate of 2.5 L/min.

Electrobiological Methanogensis

Figure 16:
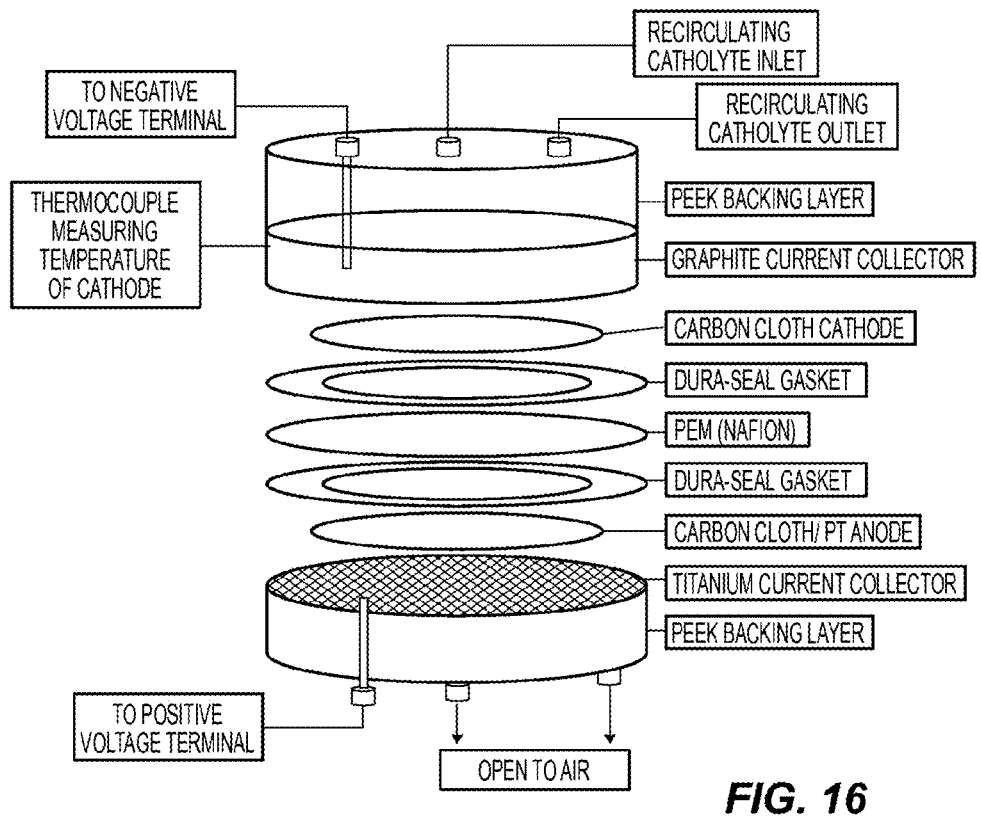
FIG. 16 is a schematic view of a biological reactor as used in Example 2.

An electrochemical cell was fabricated as shown in FIG. 16. The frame was made from polyether ether ketone (PEEK) with an anode and cathode compartment separated by Nafion 115. The anode compartment contained a titanium mesh backed by solid graphite as current collector and gas diffusion layer, an anode made of woven graphite cloth, with a carbon black coating, containing 0.5% platinum, on the anode on the side adjacent to the Nafion membrane. The cathode compartment contained a woven graphite cloth with no platinum and a solid graphite current collector.

The geometry of the electrochemical cell was cylindrical with catholyte solution inserted into the middle of the cathode and flowing radially to a fluid collection channel near the outer edge of the cathode. The catholyte solution comprised Medium 1 or Medium 1 with added NaCl to increase conductivity. No reduced carbon feedstocks are provided by the medium, thereby demonstrating the autotrophic nature of the microorganisms of *Methanothermobacter thermautotrophicus* strain UC 120910 when reducing power is provided by an electrode. The catholyte flow rate was approximately 1 ml/min and the active volume of the cathode was approximately 0.25 ml. Water supply to the anode is via diffusion across the membrane from the cathode and oxygen produced on the anode diffuses out of the cell through channels open to the air.

Figure 17:
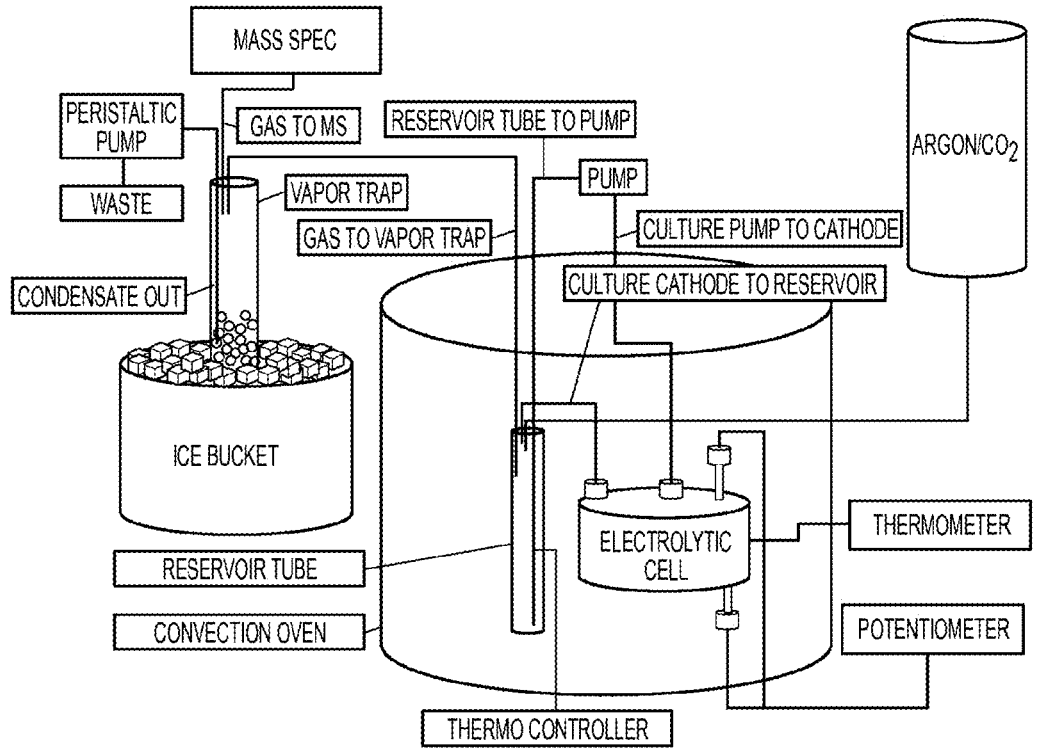
FIG. 17 is a schematic view of a testing system incorporating the biological reactor as used in Example 2.

The electrochemical cell and a culture of microorganisms of *Methanothermobacter thermautotrophicus* strain UC 120910 were held at a fixed temperature within a glass convection oven, while various electrical potentials were held across the cell as shown in FIG. 17. A supply of Argon and $CO_2$ carrier gas was used to keep the catholyte solution saturated with $CO_2$ and also to carry methane product quickly to a mass spectrometer for analysis. A chilled vapor trap was used to keep excess water from entering the mass spectrometer.

Figure 18:
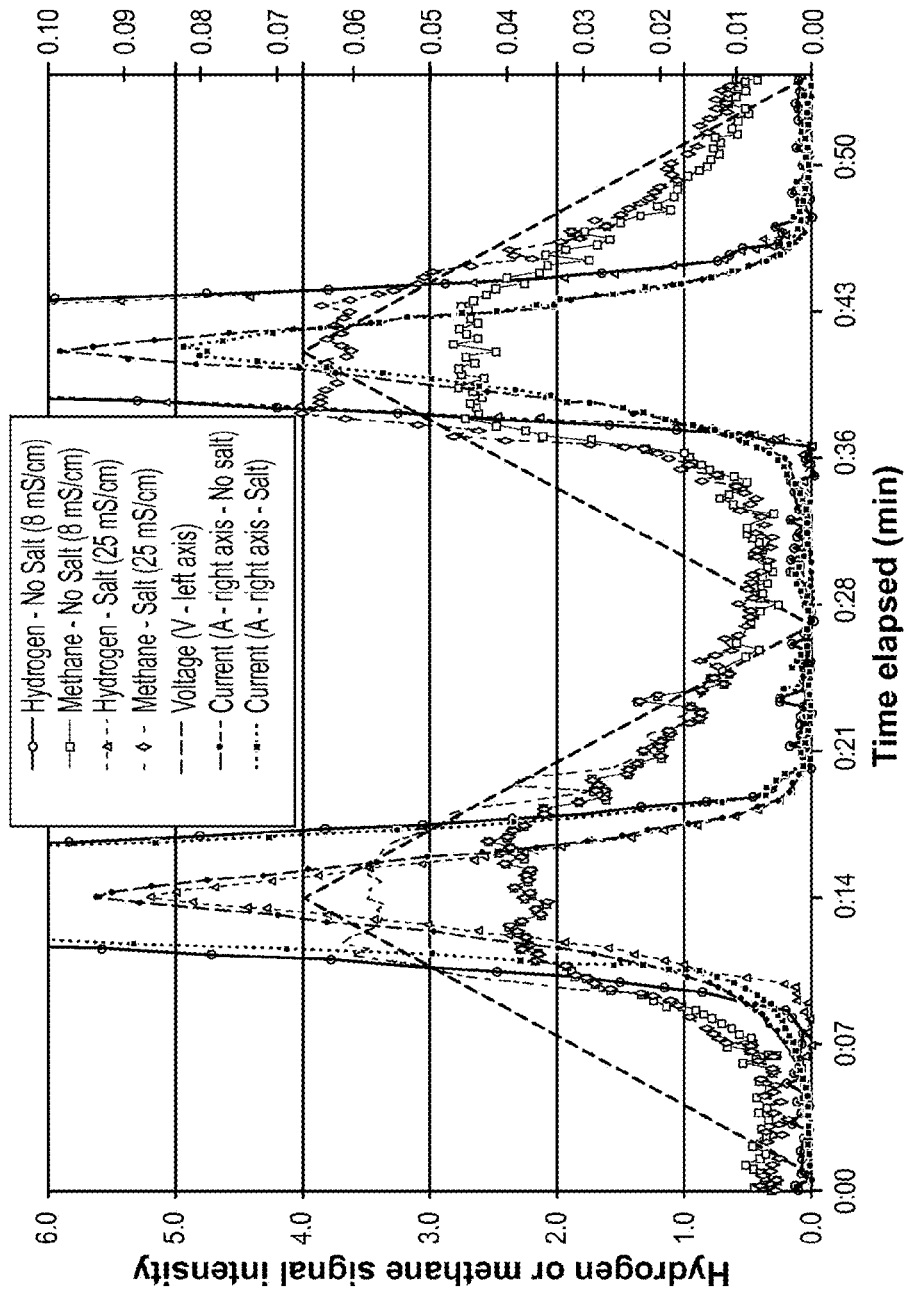
FIG. 18 is a graph of methane and hydrogen production over time with varying voltage applied across the anode and cathode of a biological reactor according to FIG. 16.
Figure 18A:
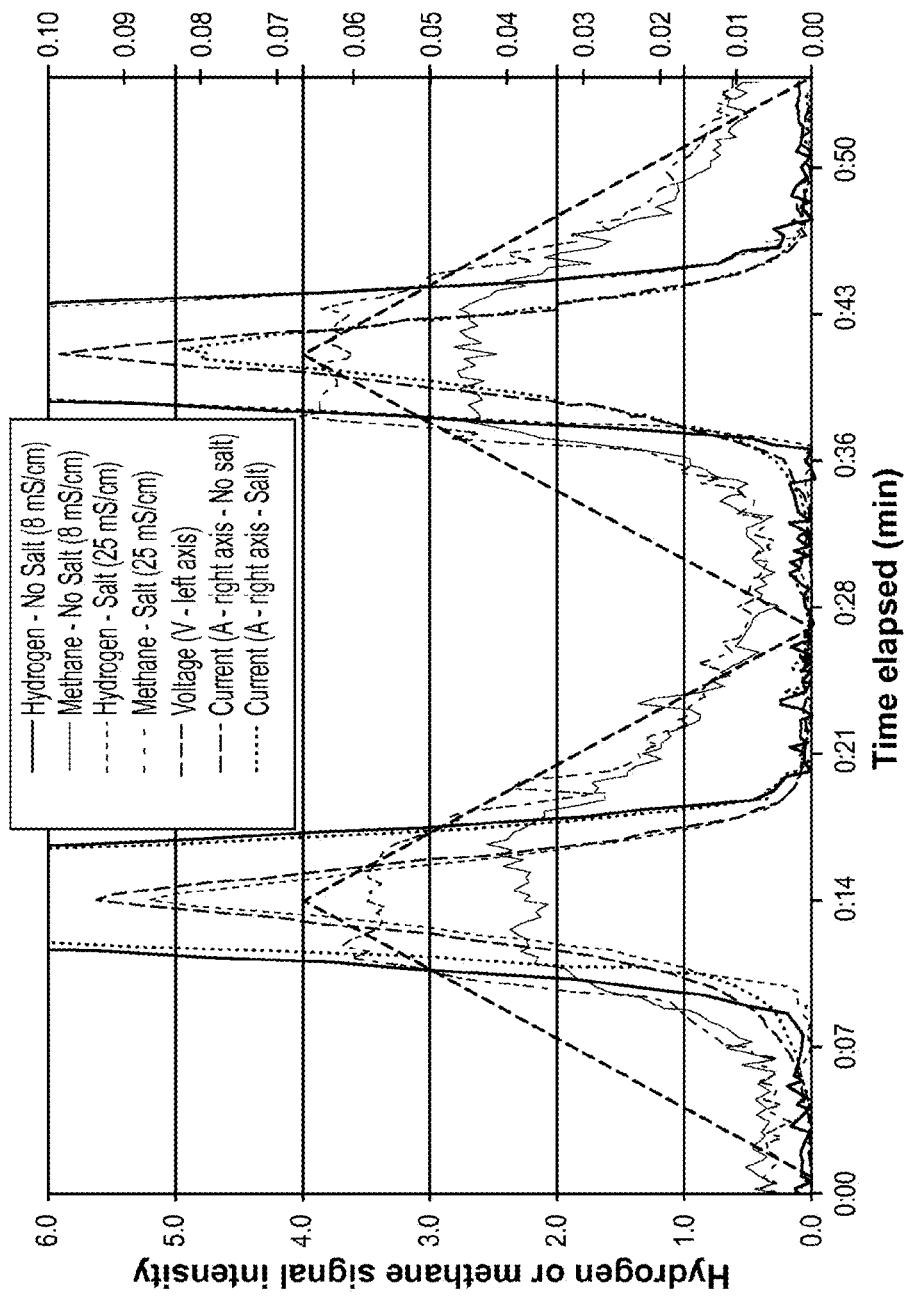
FIG. 18A depicts the same data as FIG. 18 but the data are displayed as smooth lines rather than individual data points.
Figure 19:
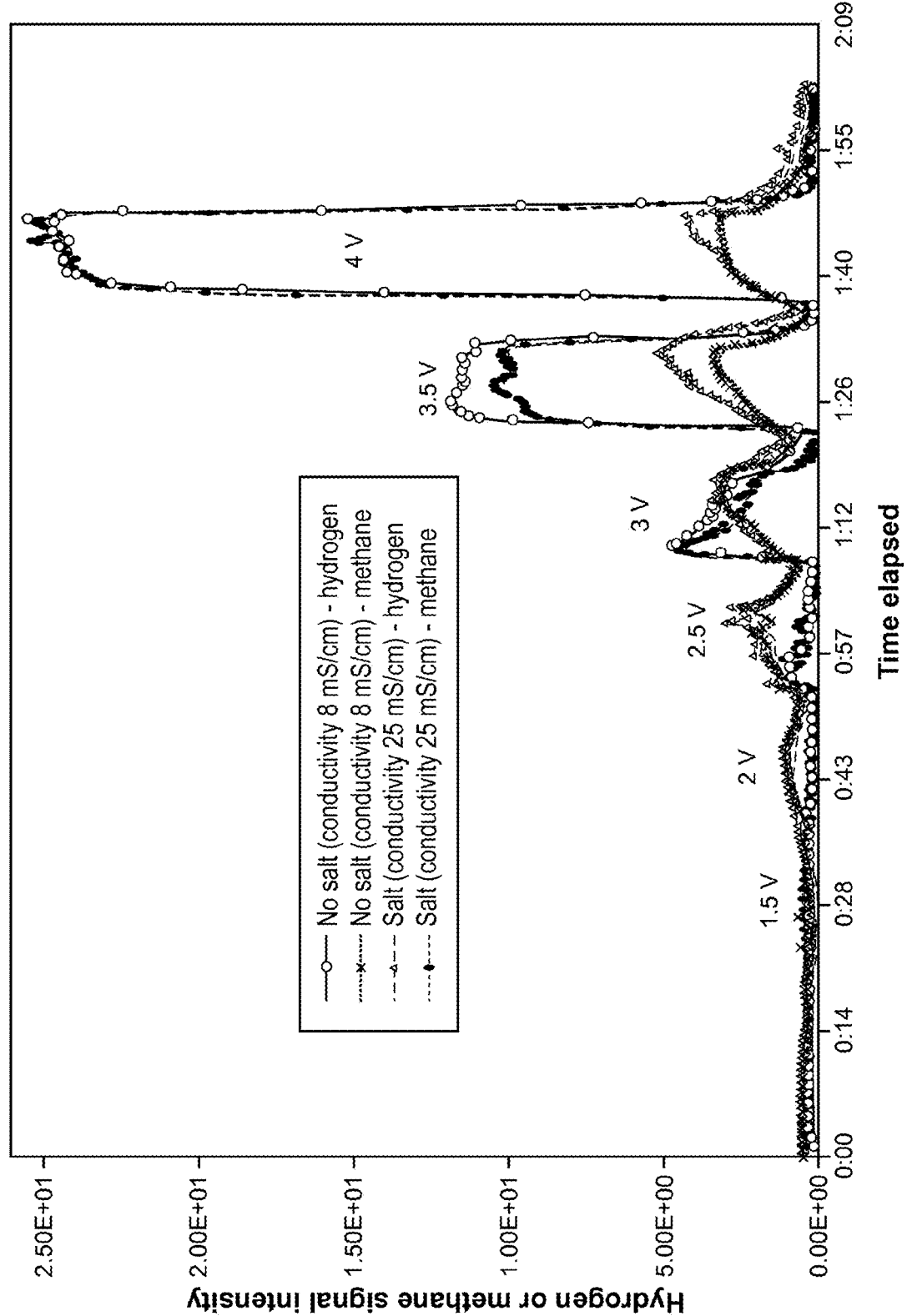
FIG. 19 is a graph of productivity over time with varying voltage applied across the anode and cathode of a biological reactor according to FIG. 16.
Figure 19A:
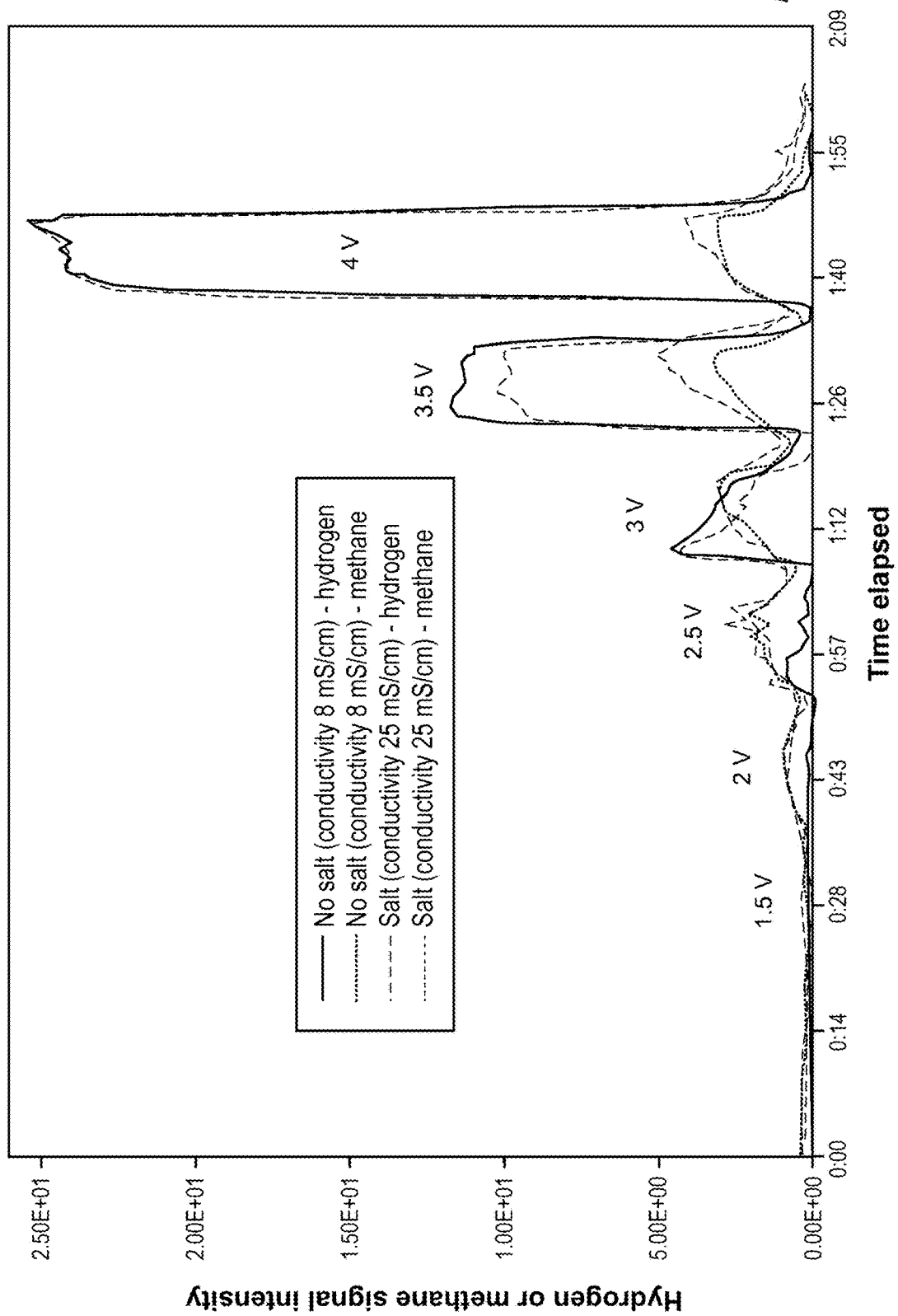
FIG. 19A depicts the same data as FIG. 19 but the data are displayed as smooth lines rather than individual data points.

FIGS. 18 and 19 show data collected at 60° C. with a catholyte culture of microorganisms of *Methanothermobacter thermautotrophicus* strain UC 120910 having a biomass density of 8.4 mg dry mass per mL culture. FIG. 18 shows the methane and hydrogen production in the cathode as a function of time as the full cell voltage is varied linearly. Methane production begins at lower voltages than hydrogen production. Sodium chloride is added to increase the catholyte conductivity from 8 mS/cm to 25 mS/cm.

FIG. 19 shows methane and hydrogen production as a function of time for full cell voltages held at the fixed values indicated. As shown in FIG. 19, the microorganisms produce methane nearly instantaneously upon the addition of power (voltage) and the maximum methane production level at each voltage level is reached within 10 minutes of voltage addition. As shown in FIG. 19, the microorganisms stop producing methane nearly instantaneously upon the removal of power (voltage) and the baseline methane production level at each voltage level is reached within 10 minutes of voltage removal.

Example 3

This example provides an exemplary comparative study of doubling time and carbon dioxide utilization efficiency among a microorganism of the disclosure and an unadapted precursor microorganism.

At the time of deposit of *Methanothermobacter thermautotrophicus* strain UC 120910, the dilution rate (reciprocal of the doubling time) of the continuous culture in the fermenter was determined by measuring the rate of culture fluid removal from the fermenter by the system that maintains a constant liquid volume in the chamber. The results of this analysis demonstrated that the culture had a doubling time of 110.8 hours. Samples from this culture were also used directly as catholyte (plus living methanogenesis catalyst) in the experiments presented in FIGS. 18 and 19.

The sample of the continuous culture in the fermenter described above was also analyzed to determine carbon dioxide utilization efficiency as expressed by the ratio of (the number of carbon dioxide molecules converted to methane) to (the number of carbon dioxide molecules converted to cellular materials). Specifically, the dry mass of cells in a given volume was determined by drying pelleted cells to constant weight and found to be 8.4 g/L of culture. Based upon the determined doubling time, the biomass increases at a rate of 0.076 g/L/hour to maintain this steady-state biomass concentration. This molar content of carbon in the biomass was estimated using the empirical formula for cell composition provided by Schill et al., Biotech Bioeng 51(6): 645-658 (1996): $CH_{1.68}O_{0.39}N_{0.24}$, to obtain the moles of biomass carbon produced per unit time. The moles of methane produced in the same time was determined as described in Example 2. Following these procedures, it was determined that the yield of methane per molecule of carbon gained in biomass, $Y_{P/X}$, was 66.9 molecules of methane produced for every one molecule of carbon dioxide converted to cellular material. This result is also expressed as 98.5% of the fixed carbon being converted to methane and only 1.5% of the fixed carbon being diverted to biomass.

The microorganism of *Methanothermobacter thermautotrophicus* strain UC 120910 is an adapted strain of DMSZ 3590, which is described in Schill et al., (1996), supra. According to Schill et al., the unadapted strain of DMSZ 3590 exhibited methane production rates as high as about 270 volumes of methane at standard temperature and pressure per volume of culture per day (VVD). At each of the tested rates, the doubling times were shown to be between 3 and 10 hours. This active growth phase is useful when biomass is the desired product. For the purposes of producing methane, any production of additional biomass is an unwanted byproduct. The highest $Y_{P/X}$ documented by Schill et al. (see Table IV) was 19.6, or about 5% of fixed carbon being diverted to biomass.

Based on the data reported in Schill et al. and the data reported herein, the efficiency of carbon dioxide conversion to methane of the microorganisms of *Methanothermobacter thermautotrophicus* strain UC 120910 are superior to those of DSMZ 3590, since only 1.5% of the carbon dioxide is converted into cellular material or maintenance of the culture, in contrast to the ~5% of the supplied carbon dioxide converted into biomass and cellular maintenance by the microorganisms of Schill et al. Without being bound to a particular theory, the superior methane productivity of *Methanothermobacter thermautotrophicus* UC 120910 may be due to the fact that the microorganisms of this strain exhibit a remarkably low doubling time.

Example 4

This example describes an exemplary method of testing resilience to contaminants.

Recovery from Oxygen Exposure

Methanogenic organisms are regarded as extremely strict anaerobes. Oxygen is known as an inhibitor of the enzyme catalysts of both hydrogen uptake and methanogenesis. A low oxidation-reduction potential (ORP) in the growth medium is regarded as important to methanogenesis.

In some embodiments, the *Methanothermobacter* microorganism of the disclosure is resilient to oxygen exposure, as the microorganism demonstrates a methane productivity level after oxygen exposure which is substantially the same as the methane productivity level exhibited before oxygen exposure.

Resilience to oxygen exposure may be analyzed by measuring the methane productivity before, during, and after oxygen exposure for various time periods. Specifically, resilience may be measured by maintaining the microorganism as essentially set forth in Example 1 and measuring the methane productivity level as essentially described in Example 2.

The culture vessel is exposed to 100% air for 10 minutes, 90 minutes, or 15 hours at a flow rate of 500 cc/min. Ambient air comprises approximately (by molar content/volume) 78% nitrogen, 21% oxygen, 1% argon, 0.04% carbon dioxide, trace amounts of other gases, and a variable amount (average around 1%) of water vapor.

During exposure to 100% air, methanogenesis is believed to be stopped and the ORP of the culture medium rises. The air used in the experiment also displaces $CO_2$ dissolved in the medium, causing the pH to rise. Following the 10 minute exposure to 100% air, gas flows of $H_2$ and $CO_2$ were restored (100 cc/min $H_2$, 25 cc/min $CO_2$).

In a first experiment, 1.5 ml of a 2.5% solution of sulfide ($Na_2SH_2O$) is added within 4 minutes of terminating air feed and restoring the $H_2/CO_2$ gas feed. Sulfide is widely used to control the ORP of the cultures, control that is regarded as essential. In another experiment, no sulfide was added.

The presence of the hydrogen in the gas phase is sufficient to reduce the ORP of the culture to enable methanogenesis, no additional control of the ORP of the culture is required. The lack of necessity of sulfide is of note in that methanogenic cultures are typically maintained at 10,000 ppm hydrogen sulfide in the gas phase. Such high levels of sulfide are not tolerated in certain industrial process, for instance, natural gas pipeline tariffs in the United States set maximum levels of hydrogen sulfide content of natural gas ranging from 4-16 ppm, depending upon the pipeline system.

Recovery from Carbon Monoxide Exposure

Carbon monoxide (CO) is another known inhibitor of enzymes involved in both hydrogen uptake and methanogenesis. CO is a potential contaminant of $CO_2$ and hydrogen streams derived from gasification of coal or biomass resources. The effect CO on methane formation by methanogen cultures is examined. Resilience to CO exposure may be analyzed by measuring the methane productivity before, during, and after oxygen exposure for various time periods. Specifically, resilience to carbon monoxide may be measured by maintaining the microorganism as essentially set forth in Example 1 and measuring the methane productivity level as essentially described in Example 2.

The pH of the culture is maintained constant by keeping CO) at 20% of the gas mix and changing only the composition of the other 80% of the gas. The culture is exposed to a mixture of 8% CO and 72% hydrogen at a flow rate of 100 cc/min and $CO_2$ at 25 cc/min for a period of 1.7 hours. Then the culture is restored to a flow of 80% hydrogen at a flow rate of 100 cc/min and $CO_2$ at 25 cc/min.

The culture is optionally subsequently exposed to a mixture of 16% CO and 64% hydrogen at a flow rate of 100 cc/min and $CO_2$ at 25 cc/min for a period of 1 hour. The culture is then restored to a flow of 80% hydrogen at a flow rate of 100 cc/min and $CO_2$ at 25 cc/min.

The culture is optionally exposed to a mixture of 40% CO and 40% hydrogen at a flow rate of 100 cc/min and $CO_2$ at 25 cc/min for a period of 20 minutes. The culture is then restored to a flow of 80% hydrogen at a flow rate of 100 cc/min and $CO_2$ at 25 cc/min.

The culture is optionally exposed to a mixture of 60% CO and 20% hydrogen at a flow rate of 100 cc/min and $CO_2$ at 25 cc/min.

During each exposure, methane production is measured as essentially described in Example 2.

Example 5

This example demonstrates that the *Methanothermobacter* microorganism of the disclosure demonstrates an excess of specific catalytic capacity when grown under steady-state, nearly stationary conditions in a continuous culture fermentor.

The specific catalytic activity of methanogenic microorganisms can be expressed as the ratio of moles of methane formed per hour to moles of carbon in the microbial biomass. Under some conditions, one of the necessary substrates may be limiting the reaction, in which case the specific catalytic capacity may exceed the measured specific catalytic activity. Thus, an increase in the limiting substrate would lead to an increase in the observed specific catalytic activity. Under other conditions, the observed specific catalytic activity may be saturated with substrate, in which case an increase in substrate concentration would not yield an increase in specific catalytic activity. Under substrate saturating conditions, the observed specific catalytic activity would equal the specific catalytic capacity.

For strain *Methanothermobacter thermautotrophicus* UC 120910 growing at steady state as described in Example 1 with a hydrogen feed rate of 0.2 L/min, the specific catalytic activity for methane production, $q_P$, was observed to be 0.37 moles methane produced per mole biomass carbon per hour. When the hydrogen feed rate was doubled to 0.4 L/min, $q_P$ doubled as well to 0.72 moles methane produced per mole biomass carbon per hour. Thus, the steady-state culture of *Methanothermobacter thermautotrophicus* UC 120910 contains specific catalytic capacity that is in excess of the specific catalytic activity that supports its growth. In other experiments with hydrogen feed rates of up to 5 L/min, specific catalytic activity of up to 4 moles methane per mole biomass carbon have been observed without signs of saturation of the rate. Thus, the specific catalytic activity of the strain is at least 10 fold greater than observed during steady-state growth with doubling times in the range of 100 hours.

Example 6

It has long been known that methanogenic Archaea are "extreme" anaerobes, whose cultivation requires considerable care to eliminate oxygen (Balch, W. E. and R. S. Wolfe, New approach to the cultivation of methanogenic bacteria: 2-mercaptoethanesulfonic acid (HS-CoM)-dependent growth of *Methanobacterium ruminantium* in a pressurized atmosphere. Appl Environ Microbiol, 1976. 32(6): p. 781-91; and Mukhopadhyay, B., E. F. Johnson, and R. S. Wolfe, Reactor-scale cultivation of the hyperthermophilic methanarchaeon *Methanococcus jannaschii* to high cell densities. Appl Environ Microbiol, 1999. 65(11): p. 5059-65). Thermophilic autotrophic methanogenic species are among the most oxygen-sensitive (See Kiener, A. and T. Leisinger, *Oxygen Sensitivity of Methanogenic Bacteria*. Systematic and Applied Microbiology, 1983. 4(3): p. 305-312). In spite of the other significant practical advantages of thermophilic autotrophic methanogens for commercial bio-catalyzed processes, extreme oxygen sensitivity emerges as a potential barrier to their use in large-scale cultivation.

In this example, we show that a pulse of oxygen (air) exposure of a high-density stirred-tank culture of *Methanothermobacter thermautotrophicus* adapted strain UC 120910 (>2 g cellular dry weight/liter) only transiently inhibits methane formation and that the oxygen is actively consumed by the culture. The results of this example also demonstrate that *Methanothermobacter thermautotrophicus* strain UC 120910 is capable of maintaining productivity above 95% conversion efficiency for extended periods, even in the presence of interruptions of hydrogen supply General culture growth conditions. Cultures were grown in a continuously stirred tank reactor (Eppendorf/New Brunswick BioFlo 110, 1.3 L microbiological chamber with full-height baffles) at 60° C., containing 600 ml medium and stirred at 1000 RPM. The medium contained 120 mM $NH_4Cl$, 10 mM NaCl, 10 mM $KH_2PO_4$, 1.21 mM nitrilotriacetate, 1 mM $MgCL_2$-$6H_2O$, 0.2 mM $FeCl_2$-$4H_2O$, 0.2 mM L-cysteine, 0.005 mM $NiCL_2$-$6H_2O$, 0.0025 mM $CoCl_2$-$6H_2O$, 0.0025 mM $Na_2MoO_4$-$2H_2O$, 0.01 mM $Na_2WO_4$, and 0.001 mM $Na_2SeO_3$. A solution of 0.5M $Na_2S$-$9H_2O$ was added to the culture at a continuous rate of 0.0035 ml/min. The pH of the medium was maintained at 6.85 via the automatic addition of a 2M $NH_4OH$ solution. The volume of medium in the culture vessel was maintained constant on a continuous basis at 600 ml by level sensor and a peristaltic pump that removed excess volume. To maintain constant mineral composition of the medium in the face of dilution by metabolic water generated during the methanogenesis process, one volume of liquid removed from the reactor is replaced via a parallel peristaltic pump delivering 0.04 volumes of a "25×" mineral mixture (250 mM NaCl, 250 mM $KH_2PO_4$, 30.25 mM nitrilotriacetate, 25 mM $MgCL_2$-$6H_2O$, 5 mM $FeCl_2$-$4H_2O$, 5 mM L-cysteine, 0.125 mM $NiCL_2$-$6H_2O$, 0.0625 mM $CoCl_2$-$6H_2O$, 0.0625 mM $Na_2MoO_4$-$2H_2O$, 0.25 mM $Na_2WO_4$, and 0.025 mM $Na_2SeO_3$). The culture was continually sparged at ambient pressure with a 4:1 mixture of $H_2$:$CO_2$ generated dynamically with mass flow controllers. The $H_2$ was Ultra Pure grade tank gas and the $CO_2$ was Bone Dry grade tank gas. No precautions were taken to remove any trace oxygen that might be present in the tank gases.

Figure 20:
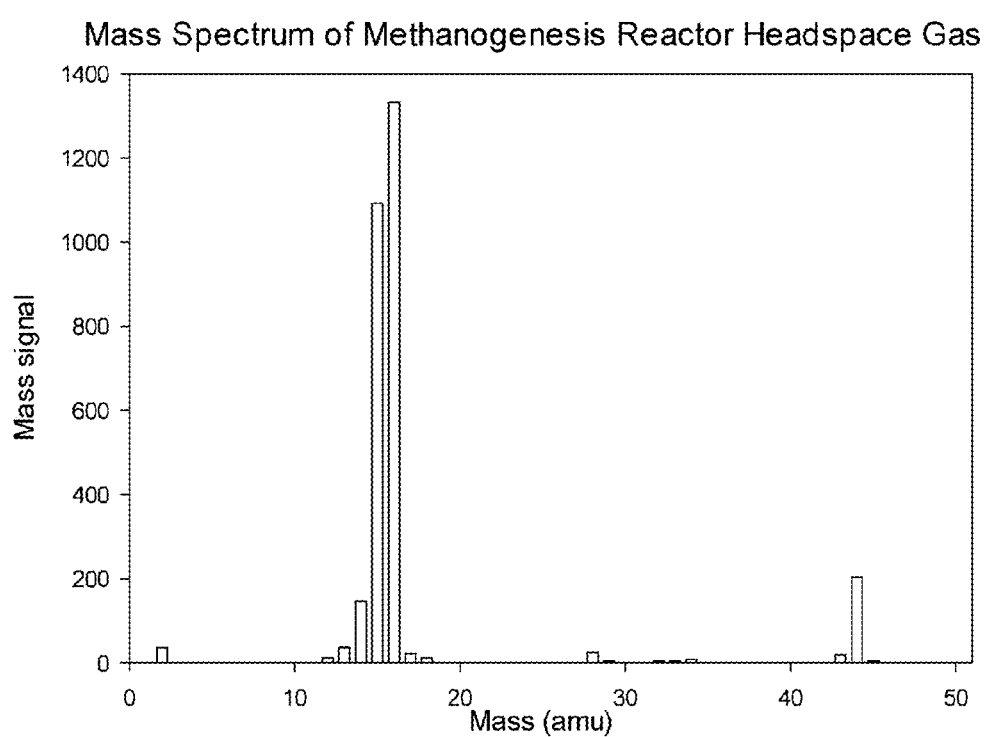
FIG. 20 is a graph of the mass spectrum of methanogenesis reactor headspace gas.

Gas analysis method. Off-gases exiting the reactor were passed through a condenser maintained at 4° C. and the condensed water returned directly to the reactor. The gas then passed through a tee junction attached to the inlet capillary of a MKS Instruments Spectra Products Cirrus quadrupole mass spectrometer (MS) programmed to continually monitor the gas composition in the range of 1 to 50 atomic mass units (amu). High sensitivity scans are repeated at a rate of approximately 3 per minute. A typical scan is shown in FIG. 20. The peak at mass 2 is exclusively from the primary hydrogen ion. The peak at mass 16 includes not only the primary ion from methane, but also fragmentation products (oxygen atoms) from water vapor and from $CO_2$. The fragmentation ion at mass 15 is exclusively from methane and is used in estimating the content of methane relative to hydrogen in the off gas. Based upon the ionization and fragmentation probabilities of hydrogen and methane gas, the relative response of the system to hydrogen (at mass 2) and methane (at mass 15) was determined to be 0.625. That is, an equimolar mixture of hydrogen and methane gave a peak at mass 2 that was 0.625 times the height of the peak at mass 15. Given the known input of hydrogen, the molar ratio of hydrogen to methane in the off gas calculated from the mass 2 and mass 15 data as described above, and the assumption that hydrogen is essentially quantitatively consumed in the methanogenesis reaction at the stoichiometric ratio of 4 hydrogen per methane produced, the conversion efficiency of the reactor can be calculated. Similar composition data can be obtained by gas chromatography of the off-gas.

Determination of cell density. Duplicate samples of 1 ml were removed from the reactor and the cells pelleted in pre-weighed microfuge tubes at 14000×g for 5 min in a micro centrifuge. The liquid was aspirated, taking care not to disturb the pellets. The tubes were then placed at 60° C. for two days and then weighed to determine the net dry weight of cells.

Steady-state productivity of *Methanothermobacter thermautotrophicus* strain UC 120910. The individual MS scan data shown in FIG. 20 is from a 107 day continuous methanogenesis culture with *Methanothermobacter thermautotrophicus* strain UC 120910 sparged under the specified growth conditions with a mixture of 0.2 NL/min $H_2$ and 0.05 NL/min CO) (see FIG. 22 described below). The dry weight cell density during this period was in the range of 8-12 g/L culture. From the individual mass spectrometer record shown in FIG. 20, it can be estimated by the calculation method specified above that the ratio of methane to hydrogen on a molar basis is 18.43, corresponding to a hydrogen-to-methane conversion efficiency of 0.987 and a methane production rate of 0.22 mol per L culture per hour. Under the stated operating conditions, the total dilution rate of the culture from all sources (metabolic water, pH adjustment, $Na_2S$ addition, mineral solution replacement) is 0.0097 $h^{-1}$, corresponding to a doubling time of 103 h. In one doubling time the culture generates ~10 g dry weight cell mass, corresponding to biomass accumulation at a rate of 0.0035 mol biomass $C-L^{-1}h^{-1}$, using the ratio of biomass C to dry cell mass determined by Duboc et al [5]. Thus, the carbon (hydrogen) diverted to biomass production by *Methanothermobacter thermautotrophicus* strain UC 120910 under the specified conditions is <1.6% (<0.8%) relative to that involved in methane production.

Air exposure method. To provide transient exposure of the culture to oxygen, a 60 ml sample of air was injected into the gas inlet stream over a period of 10 seconds, without interrupting the flow of the hydrogen:$CO_2$ mixture.

Figure 21:
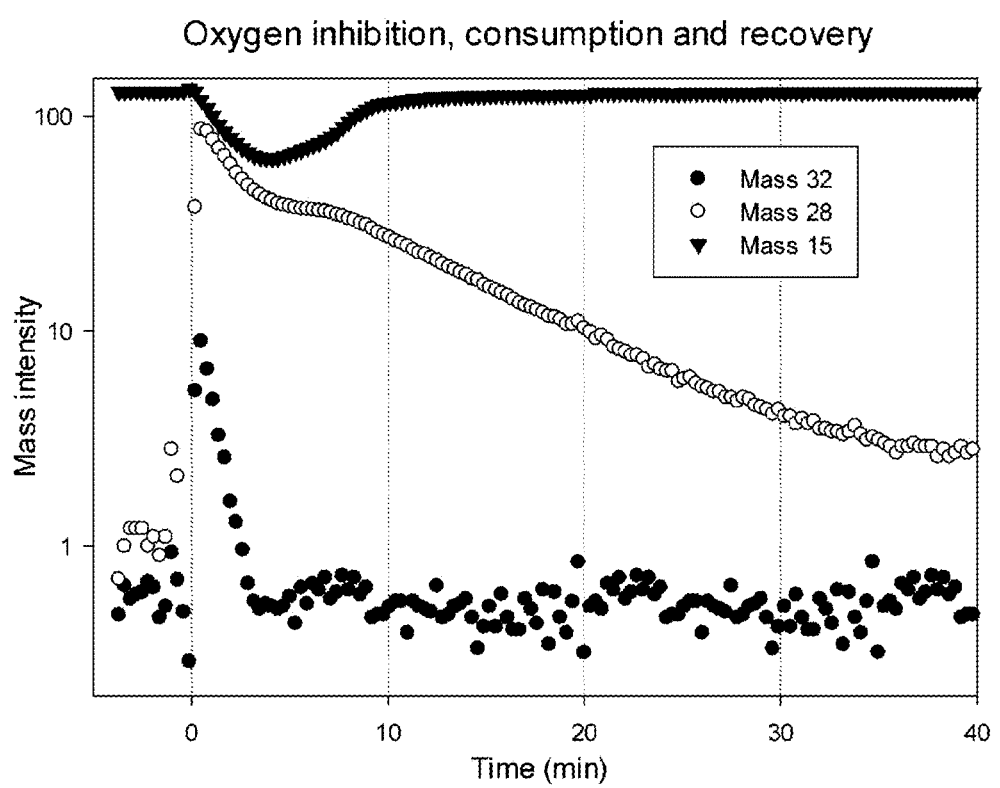
FIG. 21 is a graph depicting the effects of the injection air into a mature culture at high density (>2 g cellular dry mass/L) on oxygen inhibition, consumption and recovery.

A typical result obtained by injecting air as described above into a mature culture at high density (>2 g cellular dry mass/L) is shown in FIG. 21. A mature culture is one in which the methane production efficiency is at steady-state; not changing significantly on a daily basis. The intensity of the specified masses is shown in the figure on a log scale. The total hydrogen+$CO_2$ mixture flow rate was 250 ml/min. 60 ml air was injected at time=0. In this case, a transient decrease in methane production (mass 15 trace) is seen following the introduction of air. In examining the decline in gases introduced in the air, it is clear that oxygen (mass 32 trace) declines much more quickly (depleted within 3 min) than the inert gas nitrogen (mass 28 trace), which requires ~50 min to be completely depleted from the culture. The dense culture is clearly able to actively remove oxygen from the reactor in what appears to be a first-order process. Once the oxygen is consumed by the culture, methane production increases again, returning to >80% of the level prior to air exposure within 10 min. It is plausible that the rate of oxygen removal in the dense culture is sufficient to keep the concentration in the medium below a toxic level.

Figure 22:
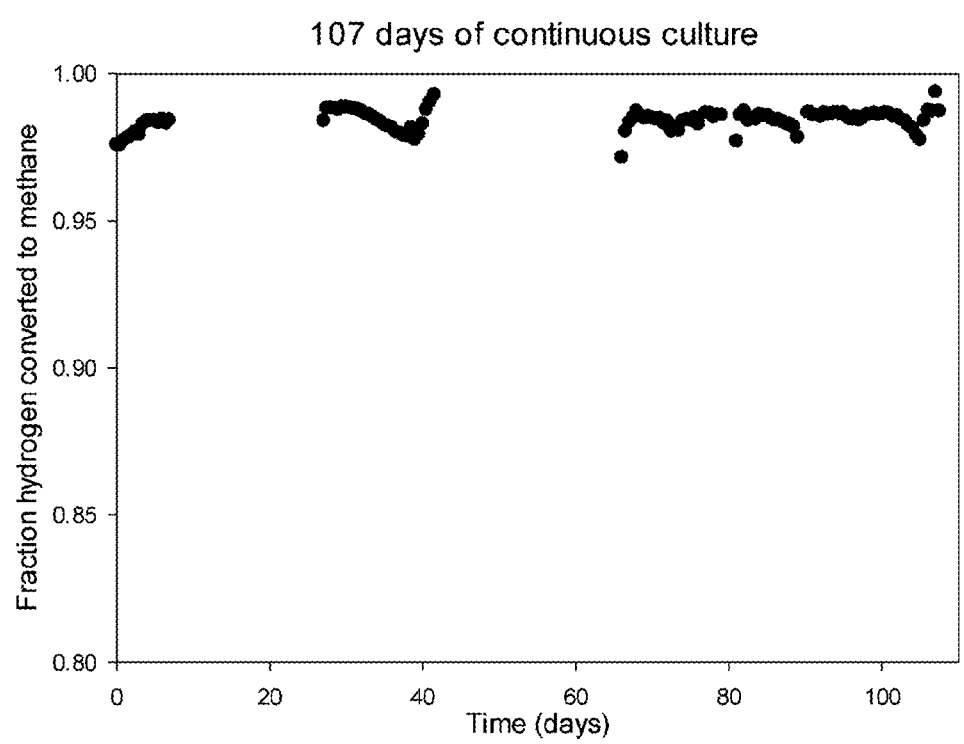
FIG. 22 is a graph of the estimated hydrogen-to-methane conversion efficiency for the entire period of a 107 day steady-state culture.

Stable long term performance of *Methanothermobacter thermautotrophicus* strain UC 120910. FIG. 22 shows the estimated hydrogen-to-methane conversion efficiency for the entire period of the 107 day steady-state culture from which the data shown in this example have been extracted. There are two gaps in the record (from days 7-27 and 41-66) during which the hydrogen and $CO_2$ gas feed was discontinued and the culture was allowed to cool to room temperature. In both cases, full conversion efficiency returned following resumption of gassing with 4:1$H_2$:$CH_4$, total gassing rate of 250 Nml/min, and as soon as the culture temperature reached the operating temperature of 60° C. The results demonstrate that *Methanothermobacter thermautotrophicus* strain UC 120910 is capable of maintaining productivity above 95% conversion efficiency for extended periods, even in the presence of interruptions of hydrogen supply.

Example 7

Two significant costs in the production of methane from carbon dioxide are the supply of reducing power in the form of either hydrogen gas or electrical power and the supply of nutrients to the microorganisms for maintenance and growth. Every percentage point improvement in the efficiency of use of the supply gases or in the decrease in requirement for the nutrients can make a significant positive impact on the ability of a renewable source of energy, such as that described in the present invention, to compete with inexpensive fossil fuels. As shown below, the present invention provides a microorganism which exhibits a significant reduction in the required reducing power and in the required nutrients.

Specifically, the required reducing power for production of methane can be observed through the carbon demands of the microorganism because the required reducing power is directly proportional to the required carbon dioxide. In the case of hydrogen gas, 4 moles of hydrogen gas are required for each mole of carbon dioxide supplied to the microorganisms. In the case of direct electrical power, 8 moles of electrons are required for each mole of carbon dioxide supplied to the microorganisms. The microorganism of the present invention demonstrates a need of between $\frac{1}{3}^{rd}$ and $\frac{1}{4}^{th}$ of the required carbon for maintenance and growth of biomass. Hence the amount of reducing power in the form of either hydrogen gas or direct electrical power which is wasted by the microorganisms for maintenance and growth of biomass is decreased by a factor of 3 to 4.

Figure 24:
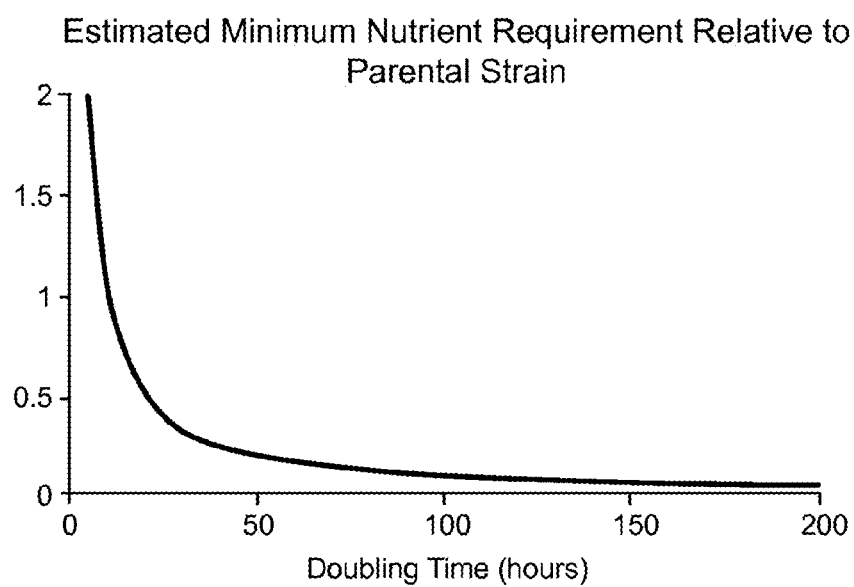
FIG. 24 is a graph depicting an exemplary relationship between the estimated nutrient requirement relative to a parental strain.

Additionally, for two strains of methanogenic microorganisms in steady-state culture under identical gas supply rates, the strain with a longer doubling time exhibited a proportionally decreased nutrient feed rate. Such an example relationship is shown in FIG. 24. The microorganism of the present invention demonstrates culture doubling times which exceed 10 times the longest time demonstrated in the literature for the parental strain.

Figure 23:
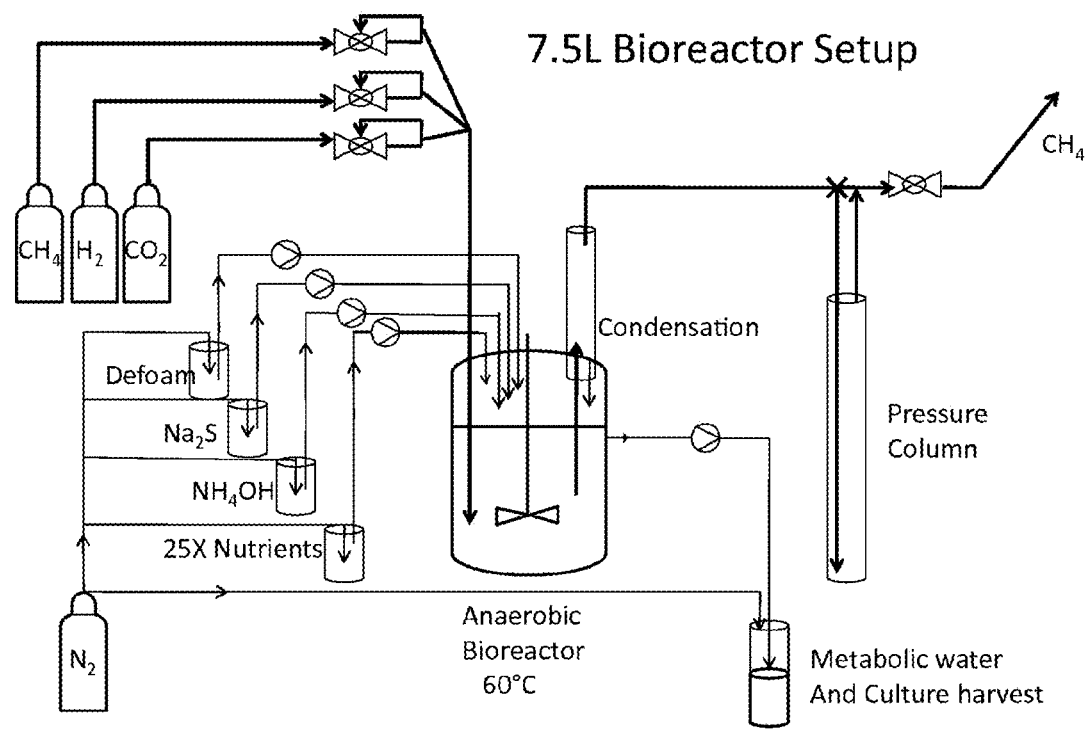
FIG. 23 is a schematic view of a 7.5 liter bioreactor setup according to the present disclosure.

An aliquot of a culture of *Methanothermobacter thermautotrophicus* strain UC 120910, deposited on Dec. 21, 2010, with the American Type Culture Collection (ATCC) under ATCC® Patent Deposit Designation No. PTA-11561, was inoculated, grown, and maintained in a 7.5 L continuously stirred bioreactor. A schematic of the setup is shown in FIG. 23.

Media was prepared and culture was inoculated according to the following procedure. General nutrients were prepared anaerobically to have the following concentrations and referred to as 25× nutrients: $KH_2PO_4$ 250 mM, NaCl 250 mM, $Na_3$ nitrilotriacetate 20 mM, nitrilotriacetate 10 mM, resazurin 0.05 mM, $NiCl_2$-$6H_2O$ 0.125 mM, $CoCl_2$-$6H_2O$ 0.0625 mM, $Na_2MoO_4$-$2H_2O$ 0.0625 mM, L-cysteine 12.5 mM, $FeSO_4$—$H_2O$ 5 mM, $MgCl_2$-$6H_2O$ 25 mM, $Na_2WO_4$ 0.25 mM, $Na_2SeO_3$ 0.025 mM.

Three liters of deoxygenated water were placed in a clean and sterile BioFlow 110 fermentor with 7.5 L vessel from New Brunswick Scientific and heated to 60° C. Probes for temperature, pH, and ORP (oxygen reduction potential) were calibrated as required and installed. 160 mL of 25× nutrients were added followed by 200 mL of 2.4M $NH_4Cl$ and 12 mL of 1.0M $Na_2CO_3$. The gas supply was turned on at the desired rate, such as a low rate of 0.20 SLPM of $H_2$ gas and 0.05 SLPM of $CO_2$ gas. The gases are sparged in from the bottom. Agitation was started using 3 equally spaced Rushton impellers and 40 mL of 0.5M $Na_2S$-$9H_2O$ was added. The pH was adjusted to 6.85 and additional deoxygenated water was added to bring the total fluid level to 4.0 L. Finally, all supply lines were connected as shown in FIG. 1 and the culture was inoculated with 40 mL of inoculum, preferably having an inoculum density (as measured by dry weight) of at least 8 mg/mL.

Figure 25:
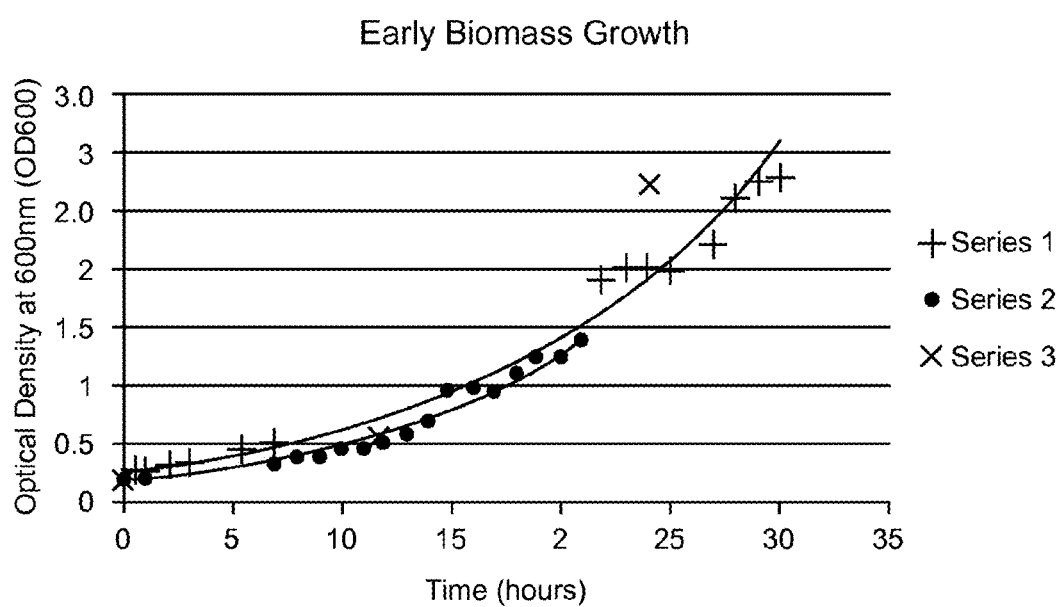
FIG. 25 is a graph depicting the early growth of the (linearized) optical density as measured at 600 nm for three separate cultures resulting from inoculation by an aliquot of strain UC120910.

After inoculation, $NH_4OH$ was added to maintain the pH at approximately 6.85 and once growth began the 0.5M $Na_2S$-$9H_2O$ was added at between 3.54/min and 10.5 μL/min. Anti-foam was added as needed and the culture was maintained at constant fluid height of approximately 4.0 L by slowly removing culture as necessary. As culture was removed, 25× nutrients were added to maintain approximately constant nutrient concentrations. As the culture grew and density increased, the conversion rate of hydrogen and carbon dioxide gas to methane increased. See FIG. 25 for an example of the early growth of the (linearized) optical density as measured at 600 nm for three separate cultures resulting from inoculation by an aliquot of strain UC120910. All three growth curves fit an exponential. The exponential curve is shown for two of the three cultures for which significantly more data were collected at early times.

Figure 26:
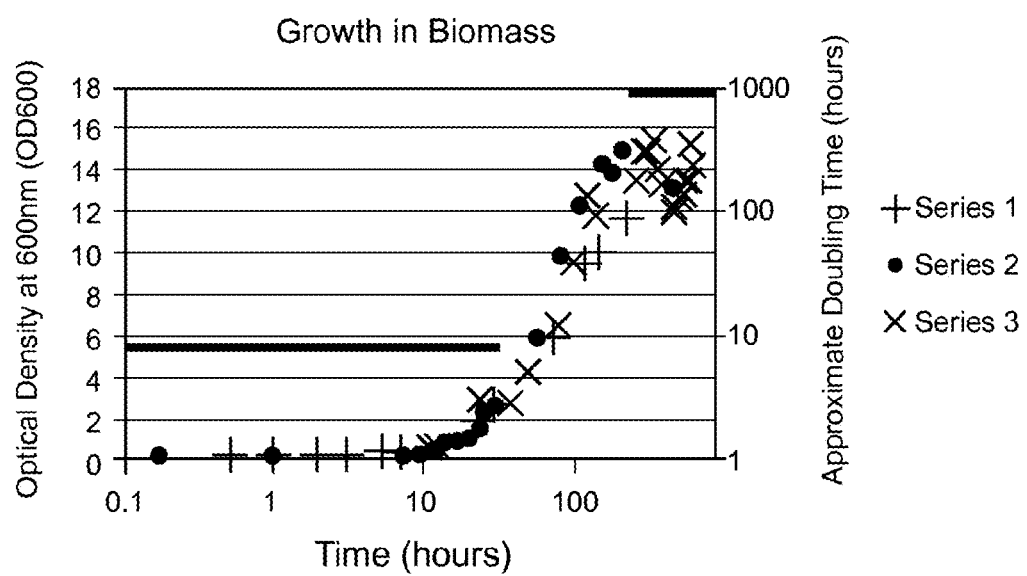
FIG. 26 is a graph depicting the late time growth characteristics of one of the cultures out to 627 hours.

FIG. 26 shows the late time growth of one of the cultures out to 627 hours. The exponential fit is not appropriate after about 30 hours and the density of the culture reaches a plateau by approximately 150 hours. At the early times during the exponential growth described above, the culture doubling time can be measured by the and for all three cultures it is about 8 hours as shown by the bold horizontal line and the right axis. At the late times, during steady-state culture the doubling time is much longer and in this particular case, it was approximately 990 hours as shown by the bold horizontal line and the right axis.

Culture density is measured by spinning down and drying a sample to measure the dry weight. Alternatively, a relative culture density may be measured with a linearized optical density at 600 nm by diluting the sample, measuring the optical density, and then multiplying the optical density by the dilution factor. The rate of conversion of hydrogen and carbon dioxide gases into methane gas may be determined through principally four means. First, the rate of gas flow in may be compared to the rate of dry gas flow out. At 100% conversion, 5 moles of hydrogen and carbon dioxide gases are converted to 1 mole of methane. In practice, more than 1 mole of gas flows out due to conversion rates which are observed to be between 45% and 98%. A soap bubble meter is used for the highest precision measurements of gas flow rates of mixed gases. Second, the rate of production of water provides a measure of methane production because 2 moles of water are produced for every mole of methane. Total fluids added and removed are tracked daily, or more often, in order to determine time averaged gas conversion rates via this water production measurement. Third, samples of input and output gases have occasionally been collected with Summa canisters and delivered to a third party analytical lab for analysis via standard gas chromatography techniques. Fourth, mass spectrometry data provides a highly responsive measure of gas conversion rates which may be quantified by normalizing the signals at each mass peak based on the detector sensitivity and the ionization probabilities as described elsewhere in this application. Multiple techniques are frequently used simultaneously and generally prove to be mutually consistent.

Through measurements of methane production, biomass density, and water production, the carbon efficiency of the microorganisms can be determined. Specifically, the ratio of grams of methane produced per gram of biomass can be calculated directly. Additionally, the ratio of carbon atoms going into methane to carbon atoms going into biomass may be calculated to understand the faradic efficiency of these microorganisms as catalysts for recycling carbon dioxide into methane. From using the approximate elemental composition of an example *Methanothermobacter* of $CH_{1.68}O_{0.39}N_{0.24}$ (Schill et al., above), one may calculate this ratio. Alternatively, this may be expressed as a ratio of molecules of methane produced per molecule of carbon dioxide supplied to the microorganisms in solution.

Example 8

Figure 27:
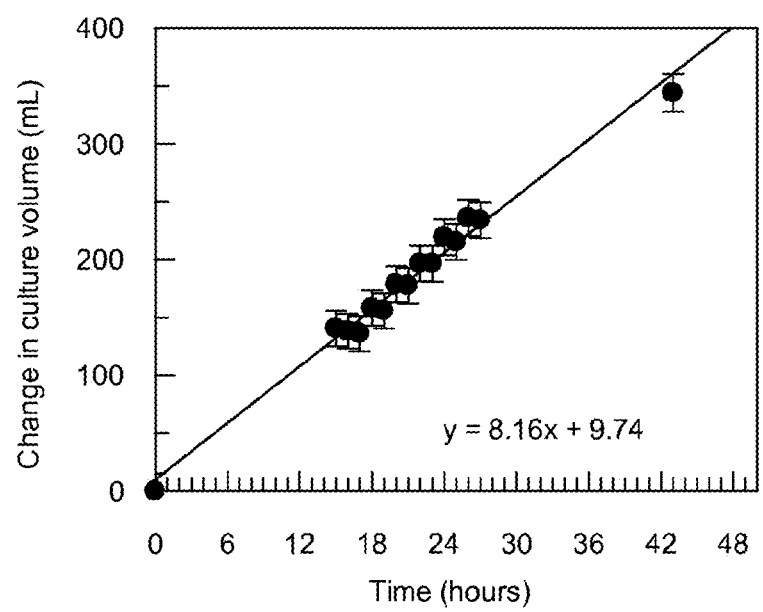
FIG. 27 is a graph depicting water production of a 4.0 L culture of strain UC 120910 measured over 43 hours.

An aliquot of a culture of *Methanothermobacter thermautotrophicus* strain UC 120910, deposited on Dec. 21, 2010, with the American Type Culture Collection (ATCC) under ATCC® Patent Deposit Designation No. PTA-11561, was grown as described above in Example 7. The 4.0 L culture was allowed to reach steady-state conditions with hydrogen gas supplied at 0.40 SLPM and carbon dioxide supplied at ¼$^{th}$ of that rate, which resulted in a culture with a dry weight density of 10.9 mg/mL. The water production was measured over 43 hours and is shown in FIG. 27. Average water production was 8.16 mL/hour. This corresponds to 3.8 mmol/hr of carbon going to biomass or about 70 carbon atoms released as methane for each carbon atom being diverted to biomass when the culture is operating in these steady-state conditions. Equivalently, there were 98.6 molecules of methane released for each 100.0 molecules of carbon dioxide supplied to the microorganisms. And, equivalently, there are 40 grams of methane produced for each gram of biomass produced. Under these conditions the doubling time of the culture was approximately 490 hours while the carbon dioxide feed rate was 36 VVD and the hydrogen feed rate was 144 VVD.

According to Schill et al., above, the parental strain of *Methanothermobacter thermautotrophicus* (DSM 3590) after reaching its highest density and achieving nearly steady-state conditions typically diverted about 1 in 16 to 1 in 19 of the carbon atoms to biomass with the remainder going to methane while the gas supply was between 230 VVD and 1150 VVD of hydrogen and between 58 VVD and 288 VVD of carbon dioxide. Under these conditions the doubling time of this culture of the parental strain is reported to be approximately 10 hours.

Next, the gas supply to the culture was terminated, all nutrient supply was turned off, and all lines into and out of the reactor were closed off. Agitation was turned off and the culture was allowed to cool off to room temperature. The culture was allowed to remain dormant without gas or other chemical supply for more than 4 weeks. Upon re-initiation of the gas supply, and upon heating the vessel, the culture began converting hydrogen and carbon dioxide into methane again. The conversion rate exceeded 80% of the input gases by the time the temperature of the culture reached 60° C.

Following reactivation of this culture as described above, the culture was utilized for various measurements of the gas conversion performance of the system and for various measurements of the robustness of the culture. The culture was maintained for more than 150 days with intermittent starts and stops. The methane productivity of the culture was generally consistent throughout the 150 days.

Example 9

Figure 28:
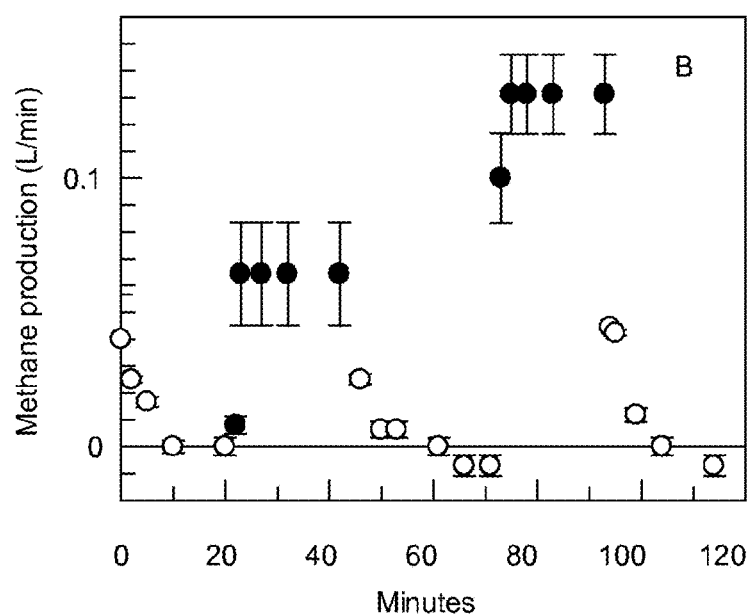
FIG. 28 is a graph depicting the methane production of a culture of strain UC 120910 while the hydrogen and carbon dioxide are fed in (closed circles) and while the hydrogen and carbon dioxide supply is cut off (open circles)

An aliquot of a culture of *Methanothermobacter thermautotrophicus* strain UC 120910, deposited on Dec. 21, 2010, with the American Type Culture Collection (ATCC) under ATCC® Patent Deposit Designation No. PTA-11561, was grown as described above in Example 7. The culture was exposed to hydrogen and carbon dioxide gases in a 4:1 ratio. The hydrogen and carbon dioxide were cycled on and off while a continuous flow of methane through the reactor was used to maintain a flow of gas out even when no hydrogen or carbon dioxide was fed in. FIG. 28 shows the methane production of the culture while the hydrogen and carbon dioxide are fed in (closed circles) and while the hydrogen and carbon dioxide supply is cut off (open circles). Methane productivity continues even after the hydrogen and carbon dioxide supply is cut off due to residual gases in the reactor. Methane productivity measurements in FIG. 28 are made through use of a soap bubble meter to observe the gas flow rates out of the reactor. Clearly, the productivity of the system begins within the time resolution of the measuring apparatus even after the supply of hydrogen and carbon dioxide was cutoff for more than 20 or more than 30 minutes.

Example 10

Figure 29:
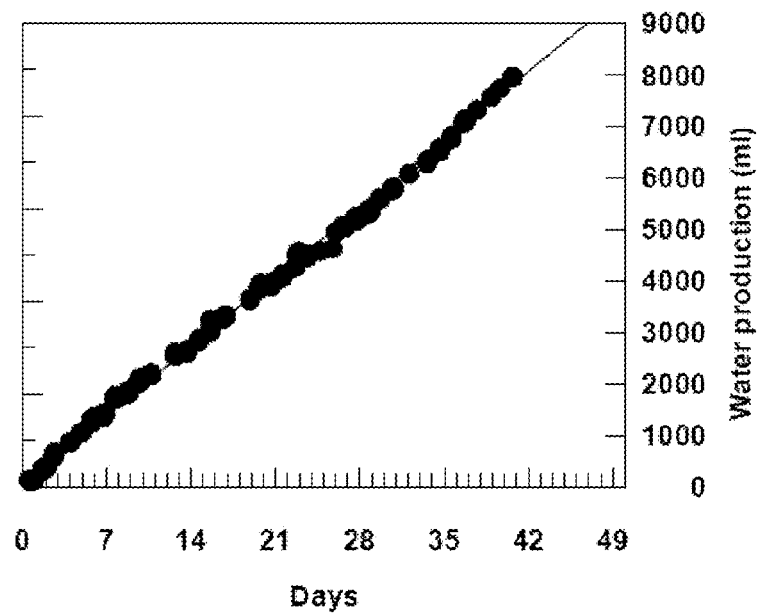
FIG. 29 is a graph depicting the water production over 40 days of a culture of strain UC 120910 maintained at a fluid volume of 3.0 L under approximately 3 psig of pressure and provided hydrogen gas at a rate of 0.48 SLPM (230 VVD), carbon dioxide at a rate of 0.12 SLPM (58 VVD), and pH held between 6.83 and 6.85.
Figure 30:
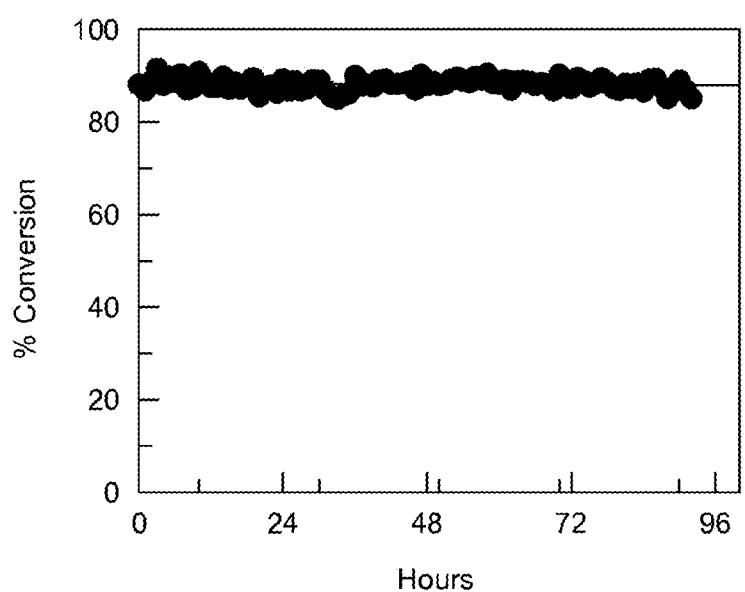
FIG. 30 is a graph depicting the nearly continuous measurement of the gas flow rates of the culture described in FIG. 29.

An aliquot of a culture of *Methanothermobacter thermautotrophicus* strain UC 120910, deposited on Dec. 21, 2010, with the American Type Culture Collection (ATCC) under ATCC® Patent Deposit Designation No. PTA-11561, was grown as described above in Example 7. This culture was maintained at a fluid volume of 3.0 L under approximately 3 psig of pressure and provided hydrogen gas at a rate of 0.48 SLPM (230 VVD) and carbon dioxide at a rate of 0.12 SLPM (58 VVD). The pH was held between 6.83 and 6.85. Performance of the system was shown to be stable and steady for 40 days as demonstrated by the water production data shown in FIG. 29. For the last 90 hours of this data collection, a nearly continuous measurement of the gas flow rates was made and is shown in FIG. 30. The best fit line to the conversion data indicates 86% conversion and zero change in the conversion rate over more than 90 hours. At this specified gas delivery rate and gas conversion rate, the culture is producing 0.10 SLPM of methane (equivalently 50 VVD of methane production). Throughout this time period, the culture maintained a dry weight density of 15.3 mg/mL and released approximately 60 molecules of methane as waste byproduct for each carbon atom added to biomass. Equivalently, there were 98.3 molecules of methane released for each 100.0 molecules of carbon dioxide supplied to the microorganisms. And, equivalently, there are 36 grams of methane produced for each gram of biomass produced. The culture doubling time was 380 hours under these conditions throughout this 40 day data collection period.

Example 11

An aliquot of a culture of *Methanothermobacter thermautotrophicus* strain UC 120910, deposited on Dec. 21, 2010, with the American Type Culture Collection (ATCC) under ATCC® Patent Deposit Designation No. PTA-11561, was grown as described above in Example 7. The culture was grown to a stable density using a stoichiometric mix of $H_2$ and $CO_2$ at 0.20 L/min $H_2$ and 0.05 L/min $CO_2$. The culture was then temporarily shut down and transported to the site of an anaerobic digester producing biogas. The biogas was unfiltered and contained dominantly $CO_2$ (30% by volume) and methane (68% by volume). It was also known to contain water vapor and hydrogen sulfide. The biogas input rate was controlled by a digital peristaltic pump designed to give a constant gas flow.

The reactor was restarted at the biogas site but using the original $H_2$ and $CO_2$ feed rates supplied by tanks of gas. The reactor was monitored until the following morning to ensure that the culture and conversion efficiency were stable following the move. The following morning a sample of the input biogas was collected for analysis then the $CO_2$ feed was turned off and replaced with a biogas feed (with H2 feed remaining constant). Two hours later a sample of the reactor output gas was collected for analysis. For the following 192 hours (8 days) gas input rates were held constant while reactor conditions were recorded.

The feed rate for the biogas was chosen in a manner that the $CO_2$ would be in excess. The peristaltic pump ran at 0.240 L/min and the actual output was recorded daily (average daily observed output was 0.239 L/min). This results in a gas delivery rate of 34 VVD of $CO_2$ and 96 VVD of $H_2$.

Figure 31:
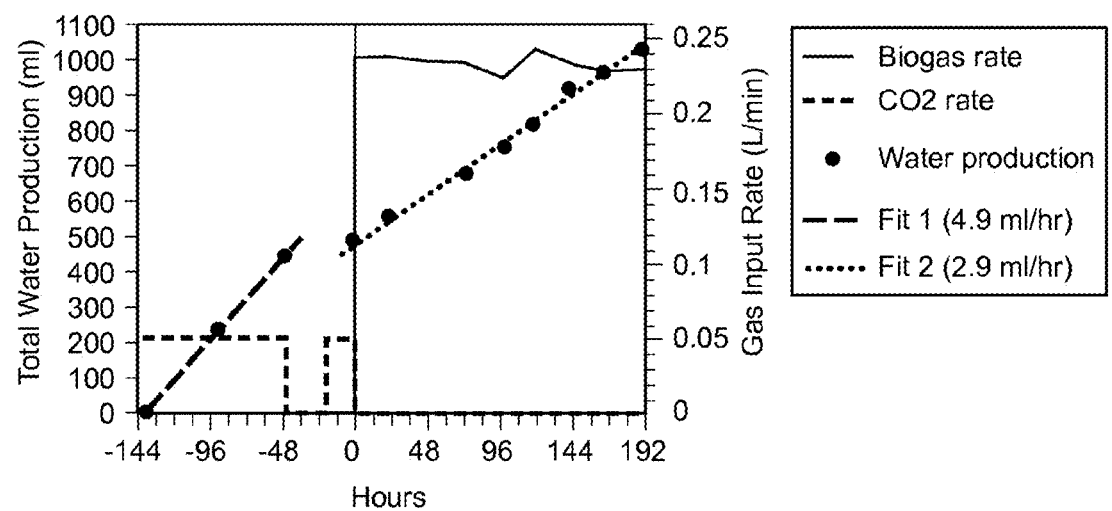
FIG. 31 is a graph depicting the daily water production of strain UC 120910 while operating with biogas and $H_2$ gas feeds after it was grown to a stable density using a stoichiometric mix of $H_2$ and $CO_2$ at 0.20 L/min $H_2$ and 0.05 L/min $CO_2$, temporarily shut down and transported to the site of an anaerobic digester producing biogas.

Daily water production was recorded before and during the trial and is shown in FIG. 31. Prior to the move when the reactor was fed $CO_2$ from tank gas, the water production was 4.9 ml/hour while after the move and while running on biogas the water production was 2.9 ml/hour. Part of this drop in rate was due to decreased residence times of the gases in the reactor (with our chosen rate for biogas the residence time is approximately one half of that when pure $CO_2$ is used). Thus the decreased water production was expected.

Figure 32:
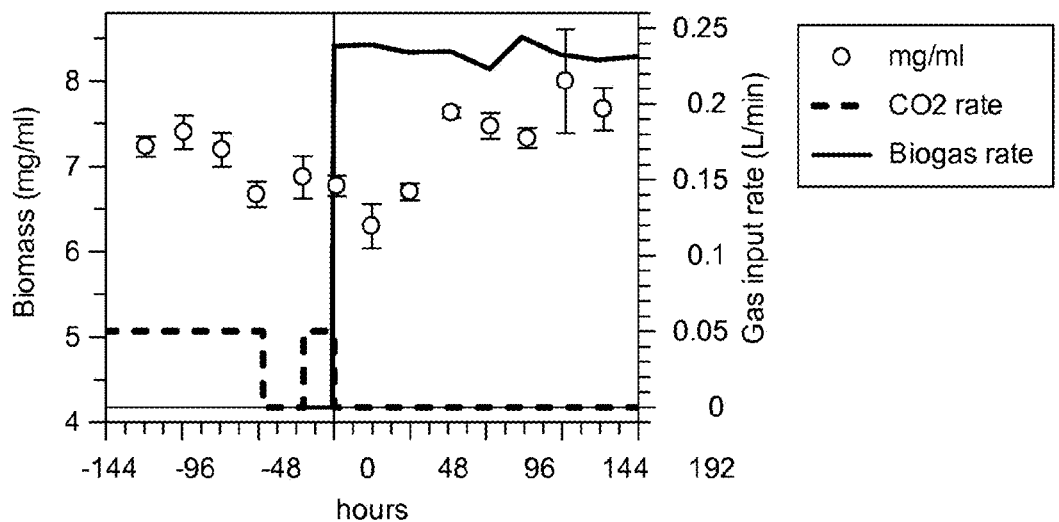
FIG. 32 is a graph depicting the dry weight of the cultures described in FIG. 31 over time.
Figure 33:
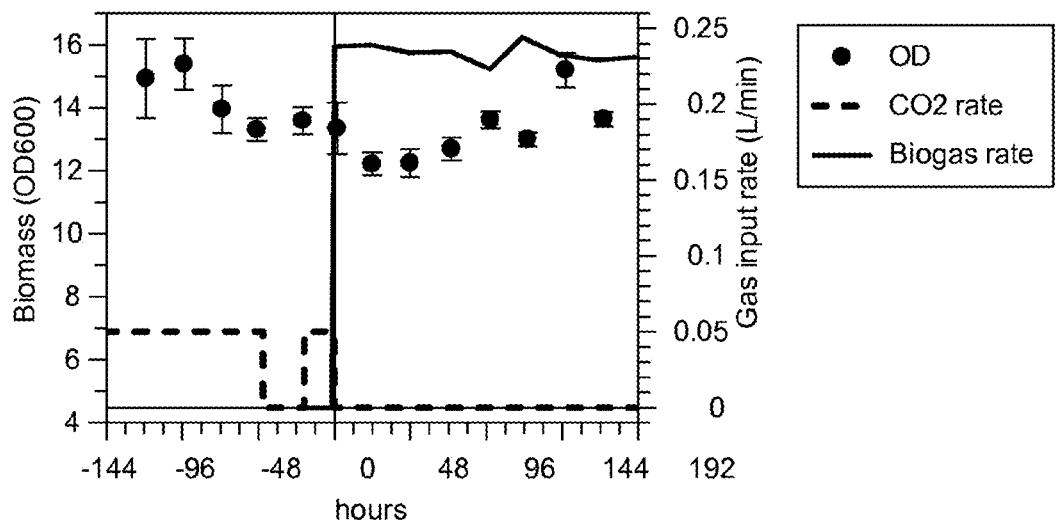
FIG. 33 is a graph depicting the optical density of the cultures described in FIG. 31 over time.

Biomass production was recorded throughout the trial and both optical density and dry weight are shown in FIGS. 33 and 32, respectively. Throughout the trial on biogas, the culture increased in biomass by roughly 17% as measured by dry weight and by roughly 7% as measured by optical density. Using the methodology described above, the ratio of carbon to biomass can be calculated. Approximately 52 carbon atoms are used for $CH_4$ production for each single carbon atom going to biomass production. Equivalently, there were 98.1 molecules of methane released for each 100.0 molecules of carbon dioxide supplied to the microorganisms. And, equivalently, there are 20 grams of methane produced for each gram of biomass produced. Throughout the trial on biogas, the doubling time of the culture was approximately 990 hours.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed:

1. A method of culturing methanogenic microorganisms of *Methanothermobacter thermautotrophicus* strain UC 120910, deposited on Dec. 21, 2010, with the American Type Culture Collection (ATCC®) under ATCC® Patent Deposit Designation No. PTA-11561, comprising the step of culturing said microorganisms, including progeny thereof, in culture medium that supports the growth and/or survival of methanogenic microorganisms, wherein the progeny resulted from reproduction or multiplication of a microorganism of *Methanothermobacter thermautotrophicus* strain UC 120910 and wherein the progeny comprise a 16s RNA that is at least 90% identical to the full length sequence of SEQ ID NO: 1.

2. The method of claim 1 comprising supplying sodium, potassium, magnesium, iron, chloride, nickel, cobalt, selenium, sulfur sources, phosphorus sources, and/or nitrogen sources to the culture medium.

3. The method of claim 2 comprising supplying sulfide to the culture medium.

4. The method of claim 3 comprising supplying a nitrogen source to the culture medium.

5. The method of claim 4 comprising supplying phosphate to the culture medium.

6. The method of claim 5 comprising supplying NaCl to the culture medium.

7. The method of claim 2 comprising (a) supplying hydrogen and carbon dioxide to the culture medium and (b) recovering methane produced by the methanogenic microorganisms.

8. The method of claim 1 wherein the method comprises culturing the methanogenic microorganisms in an active growth phase.

9. The method of claim 1 wherein the method comprises culturing the methanogenic microorganisms in a near-stationary or stationary growth phase.

10. A method of culturing methanogenic microorganisms of *Methanothermobacter thermautotrophicus* strain UC 120910, deposited on Dec. 21, 2010, with the American Type Culture Collection (ATCC®) under ATCC® Patent Deposit Designation No. PTA-11561, comprising the step of (a) culturing said microorganisms, including progeny thereof, in a near-stationary growth phase, (b) supplying hydrogen and carbon dioxide to said microorganisms, and (c) recovering methane produced by the methanogenic microorganisms, wherein the progeny resulted from reproduction or multiplication of a microorganism of *Methanothermobacter thermautotrophicus* strain UC 120910 and wherein the progeny comprise a 16s RNA that is at least 90% identical to the full length sequence of SEQ ID NO: 1, and wherein the culturing results in a methane production efficiency that is at least 25 $CO_2$ molecules converted to methane per $CO_2$ molecule converted to cellular material, or wherein the culturing results in conversion of at least 96 molecules of methane per 100 molecules of carbon dioxide supplied to the microorganism, or wherein the culturing results in recovery of at least 17 grams of methane per gram of biomass produced.

11. The method of claim 10, wherein the culturing results in a ratio of the number of $CO_2$ molecules converted to methane by the microorganisms to the number of $CO_2$ molecule converted to cellular material by the microorganisms of about 8:1 to about 20:1.

12. A method of culturing methanogenic microorganisms of *Methanothermobacter thermautotrophicus* strain UC 120910, deposited on Dec. 21, 2010, with the American Type Culture Collection (ATCC®) under ATCC® Patent Deposit Designation No. PTA-11561, comprising the step of culturing said microorganisms, including progeny thereof, in culture medium that supports the growth and/or survival of methanogenic microorganisms, wherein the progeny resulted from reproduction or multiplication of a microorganism of *Methanothermobacter thermautotrophicus* strain UC 120910, and wherein the progeny produces at least 96 molecules of methane per 100 molecules of carbon dioxide supplied to the microorganism.

13. The method of claim 12 comprising supplying sodium, potassium, magnesium, iron, chloride, nickel, cobalt, selenium, sulfur sources, phosphorus sources, and/or nitrogen sources to the culture medium.

14. The method of claim 12 comprising supplying sulfide to the culture medium.

15. The method of claim 12 comprising supplying a nitrogen source to the culture medium.

16. The method of claim 12 comprising supplying phosphate to the culture medium.

17. The method of claim 12 comprising supplying NaCl to the culture medium.

18. The method of claim 12 comprising (a) supplying hydrogen and carbon dioxide to the culture medium and (b) recovering methane produced by the methanogenic microorganisms.

19. The method of claim 12 wherein the method comprises culturing the methanogenic microorganisms in an active growth phase.

20. The method of claim 12 wherein the method comprises culturing the methanogenic microorganisms in a near-stationary or stationary growth phase.

\* \* \* \* \*

```
                          SEQUENCE LISTING

<160> NUMBER OF SEQ ID NOS: 1

<210> SEQ ID NO 1
<211> LENGTH: 1334
<212> TYPE: DNA
<213> ORGANISM: Methanothermobacter thermautotrophicus
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (1309)..(1309)
<223> OTHER INFORMATION: n is a, c, g, or t
<220> FEATURE:
<221> NAME/KEY: misc_feature
<222> LOCATION: (1334)..(1334)
<223> OTHER INFORMATION: n is a, c, g, or t
<300> PUBLICATION INFORMATION:
<308> DATABASE ACCESSION NUMBER: GenBank / X68720.1
<309> DATABASE ENTRY DATE: 2003-06-06
<313> RELEVANT RESIDUES IN SEQ ID NO: (1)..(1334)

<400> SEQUENCE: 1
tggataacct gcccttggga ccgggataac cccgggaaac tggggataaa cccggatagg     60
tgatgctgcc tggaatggtt cttcaccgaa acaccttcgg gtgcccaagg atgggtctgc    120
ggccgattag gttgttggta gggtaacggc ctaccaagcc gatcatcggt acgggttgtg    180
agagcaagag cccggagatg gaacctgaga caaggttcca ggccctacgg ggcgcagcag    240
gcgcgaaacc tccgcaatgc acgcaagtgc gacngggaa ccccaagtgc cactcttaac    300
ggggtggctt ttcagaagtg taaaaagctt ctggaataag ggctgggcaa gaccggtgcc    360
agccgccgcg gtaacaccgg cagctcaagt ggtagccgct tttattgggc ctaaagcgtc    420
```

-continued

```
cgtagccggt ctgataagtc tctggtgaaa tcccacagct taactgtggg aattgctgga    480
gatactatca tgactcgagg tcgggagagg ctggaggtac tcccagggta ggggtgaaat    540
cctgtaatcc tgggaggacc acctgtngcg aangcgtcca gctggaacga acctgacngt    600
gagggacgaa agccaggggc gcgaaccgga ttagataccc gggtagtcct ggccgtaaac    660
gatgtggact tggtgttggg atggcttcga gctgcccag tgccgaaggg aagctgttaa     720
gtccaccgcc tgggaagtac ggccgcaagg ctgaaactta aaggaattgg cgggggagca    780
ccacaacgcg tggagcctgc ggtttaattg gattcaacgc cggacatctc accaggggcg    840
acagcagtat gatggccagg ttgatgacct tgcctgacga gctgagagga ggtgcatggc    900
cgccgtcagc tcgtaccgtg aggcgtcctg ttaagtcagg caacgagcga gacccacgcc    960
cttagttacc agcggaaccc ttatgggttg ccgggcacac taaggggacc gccagtgata   1020
aactggagga aggagtggac gacggtaggt ccgtatgccc cgaatcccct gggcaacacg   1080
cgggctacaa tggcctggac aatgggttcc gacaccgaaa ggtggaggta atcccctaaa   1140
ccaggtcgta gttcggatcg agggctgtaa cccgccctcg tgaagctgga atgcgtagta   1200
atcgcgtgtc actatcgcgc ggtgaatacg tccctgctcc ttgcacacac cgcccgtcac   1260
gccacccaaa aagggcttgg atgaggccac aacattctgt tgtggtcgna tctgggttct   1320
ttgaggaggg cgan                                                     1334
```